(12) United States Patent
Wilson et al.

(10) Patent No.: US 12,428,653 B2
(45) Date of Patent: *Sep. 30, 2025

(54) GENE THERAPY FOR CEROID LIPOFUSCINOSES

(71) Applicant: The Trustees of the University of Pennsylvania, Philadelphia, PA (US)

(72) Inventors: James M. Wilson, Philadelphia, PA (US); Nathan Katz, Stamford, CT (US); Christian Hinderer, Baltimore, MD (US); Juliette Hordeaux, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/148,077

(22) Filed: Dec. 29, 2022

(65) Prior Publication Data

US 2023/0383312 A1 Nov. 30, 2023

Related U.S. Application Data

(63) Continuation of application No. 16/611,512, filed as application No. PCT/US2018/032278 on May 11, 2018, now Pat. No. 11,591,614.

(60) Provisional application No. 62/652,006, filed on Apr. 3, 2018, provisional application No. 62/599,816, filed on Dec. 18, 2017, provisional application No. 62/504,817, filed on May 11, 2017.

(51) Int. Cl.
| | | |
|---|---|---|
| *C12N 15/86* | (2006.01) | |
| *A61K 48/00* | (2006.01) | |
| *C12N 9/48* | (2006.01) | |
| *A61K 9/00* | (2006.01) | |

(52) U.S. Cl.
CPC .......... *C12N 15/86* (2013.01); *A61K 48/0075* (2013.01); *C12N 9/485* (2013.01); *A61K 9/0019* (2013.01); *C12N 2710/16143* (2013.01); *C12N 2750/14143* (2013.01); *C12Y 304/14009* (2013.01)

(58) Field of Classification Search
None
See application file for complete search history.

(56) References Cited

U.S. PATENT DOCUMENTS

| | | |
|---|---|---|
| 5,139,941 A | 8/1992 | Muzyczka et al. |
| 5,478,745 A | 12/1995 | Samulski et al. |
| 5,741,683 A | 4/1998 | Zhou et al. |
| 6,057,152 A | 5/2000 | Samulski et al. |
| 6,204,059 B1 | 3/2001 | Samulski et al. |
| 6,268,213 B1 | 7/2001 | Samulski et al. |
| 6,491,907 B1 | 12/2002 | Rabinowitz et al. |
| 6,596,535 B1 | 7/2003 | Carter et al. |
| 6,660,514 B1 | 12/2003 | Zolotukhin et al. |
| 6,951,753 B2 | 10/2005 | Shenk et al. |
| 7,094,604 B2 | 8/2006 | Snyder et al. |
| 7,125,717 B2 | 10/2006 | Carter et al. |
| 7,172,893 B2 | 2/2007 | Rabinowitz et al. |
| 7,201,898 B2 | 4/2007 | Monahan et al. |
| 7,229,823 B2 | 6/2007 | Samulski et al. |
| 7,282,199 B2 | 10/2007 | Gao et al. |
| 7,439,065 B2 | 10/2008 | Ferrari et al. |
| 7,456,683 B2 | 11/2008 | Takano et al. |
| 7,588,772 B2 | 9/2009 | Kay et al. |
| 7,629,322 B2 | 12/2009 | Kleinschmidt et al. |
| 7,790,449 B2 | 9/2010 | Gao et al. |
| 7,906,111 B2 | 3/2011 | Wilson et al. |
| 7,985,565 B2 | 7/2011 | Mayer et al. |
| 8,008,005 B2 | 8/2011 | Belshaw et al. |
| 8,734,809 B2 | 5/2014 | Gao et al. |
| 8,927,514 B2 | 1/2015 | Chatterjee et al. |
| 9,849,195 B2 | 12/2017 | Davidson et al. |
| 10,265,417 B2 | 4/2019 | Wilson et al. |
| 10,391,184 B2 | 8/2019 | Davidson et al. |
| 2006/0136184 A1 | 6/2006 | Gustafsson et al. |
| 2013/0310443 A1* | 11/2013 | Srivastava .............. A61P 35/00 435/320.1 |
| 2014/0032186 A1 | 1/2014 | Gustafsson et al. |
| 2014/0107189 A1 | 4/2014 | Bancel et al. |
| 2015/0344911 A1 | 12/2015 | Chatterjee et al. |
| 2016/0038613 A1* | 2/2016 | Kaspar ............... A61K 48/0075 435/235.1 |
| 2016/0166709 A1 | 6/2016 | Davidson et al. |

FOREIGN PATENT DOCUMENTS

| | | |
|---|---|---|
| WO | WO 2003/042397 | 5/2003 |
| WO | WO 2005/033321 | 4/2005 |
| WO | WO 2006/110689 | 10/2006 |

(Continued)

OTHER PUBLICATIONS

GenBank Accession AAS99264, capsid protein VP1 [Adeno-associated virus 9], 2004.*

Bucher et al., Intracisternal Delivery Of AAV9 Results In Oligodendrocyte And Motor Neuron Transduction In The Whole Central Nervous System Of Cats, Gene Therapy, vol. 21(5) :522-8, May 2014.

Buning et al., Recent developments in adeno-associated virus vector technology, The Journal of Gene Medicine, vol. 10(7):717-33, Jul. 2008.

(Continued)

*Primary Examiner* — Benjamin P Blumel
(74) *Attorney, Agent, or Firm* — Howson & Howson LLP

(57) ABSTRACT

Provided herein are methods and compositions for treatment of Batten disease. Such compositions include a recombinant adeno-associated virus (rAAV), said rAAV comprising an AAV capsid, and a vector genome packaged therein, said vector genome comprising (a) an AAV inverted terminal repeat (ITR) sequence; (b) a promoter; (c) a CLN2 coding sequence encoding a human TPP1; (d) an AAV 3' ITR.

47 Claims, 25 Drawing Sheets

Specification includes a Sequence Listing.

(56) References Cited

FOREIGN PATENT DOCUMENTS

| WO | WO 2010/053572 | 5/2010 |
|----|----------------|--------|
| WO | WO 2010/071832 | 6/2010 |
| WO | WO 2011/126808 | 10/2011 |
| WO | WO 2012/158757 | 11/2012 |
| WO | WO 2012/170930 | 12/2012 |
| WO | WO 2013/049493 | 4/2013 |
| WO | WO 2013/151672 | 10/2013 |
| WO | WO 2013/182683 | 12/2013 |
| WO | WO 2015/012924 | 1/2015 |
| WO | WO 2015/013148 | 1/2015 |
| WO | WO 2015/164723 | 10/2015 |
| WO | WO 2016/049230 | 3/2016 |
| WO | WO 2017/070678 | 4/2017 |
| WO | WO 2017/136500 | 8/2017 |
| WO | WO 2017/160360 | 9/2017 |
| WO | WO 2018/160582 | 9/2018 |

OTHER PUBLICATIONS

Buss et al., Characterization of AAV-mediated dorsal root ganglionopathy, Molecular Therapy: Methods & Clinical Development, vol. 24(p. 342-354), Mar. 10, 2022.

Buss et al. [Abstract] AAV9.hCLN2 (RGX-181) improves survival and neuropathology in TPP1m1j mice, a model for CLN2 Batten disease, ESGCT 27th Annual Congress, Barcelona, Spain, Oct. 22-25, 2019.

Daber et al., A novel molecular switch, Journal of Molecular Biology, vol. 371(4):661-70, Aug. 2009.

David et al., Recombinant adeno-associated virus-mediated in utero gene transfer gives therapeutic transgene expression in the sheep, Human Gene Therapy, vol. 22(4):419-26, Apr. 2011.

Davidoff et al., Sex significantly influences transduction of murine liver by recombinant adeno-associated viral vectors through an androgen-dependent pathway, Blood, vol. 102(2):480-8, Jul. 2003.

Damdindorji et al., A comparative analysis of constitutive promoters located in adeno-associated viral vectors, PLoS One, vol. 9(8):e106471, Aug. 2014.

Diehl et al., A good practice guide to the administration of substances and removal of blood, including routes and volumes, Journal of Applied Physiology, vol. 21(1):15-23, Jan.-Feb. 2001.

Dirren et al., Intracerebroventricular injection Of adeno-associated Virus 6 And 9 vectors for cell type-specific transgene expression in the spinal cord, Human Gene Therapy, vol. 25(2):109-20, Feb. 2014.

Federici et al., Robust Spinal Motor Neuron Transduction Following Intrathecal Delivery Of AAV9 In Pigs, Gene Therapy, vol. 19(8):852-9, Aug. 2012.

Fisher et al., Transduction with recombinant adeno-associated virus for gene therapy is limited by leading-strand synthesis, Journal of Virology, vol. 70(1):520-532, Jan. 1996.

Fietz et al., Diagnosis of neuronal ceroid lipofuscinosis type 2 (CLN2 disease): Expert recommendations for early detection and laboratory diagnosis, Molecular Genetics and Metabolism, vol. 119(1-2):160-7, Sep. 2016.

Foust et al., Rescue of the spinal muscular atrophy phenotype in a mouse model by early postnatal delivery of SMN, Nature Biotechnology, vol. 28(3):271-4, Mar. 2010.

Gao et al., Clades of Adeno-Associated Viruses are Widely Disseminated in Human Tissues, Journal of Virology, vol. 78(12):6381-8, Jun. 2004.

Giles et al., Deamidation of Amino Acids on the Surface of Adeno-Associated Virus Capsids Leads to Charge Heterogeneity and Altered Vector Function, Mol Ther. Dec. 5, 2018;26(12):2848-2862.

Goebel, H., The neuronal ceroid-lipofuscinoses, Journal of Child Neurology, vol. 10(6):424-37, Nov. 1995.

Graham et al., Characteristics of a human cell line transformed by DNA from human adenovirus type 5, Journal of General Virology, vol. 36(1):59-74, Jul. 1977.

Gray et al., Global CNS gene delivery and evasion of anti-AAV-neutralizing antibodies by intrathecal AAV administration in non-human primates, Gene Therapy, vol. 2094):450-9, Apr. 2013.

Gordeeva et al., Improved PCR-based gene synthesis method and its application to the Citrobacter freundii phytase gene codon modification, Journal Microbiological Methods, vol. 81(2)147-52, May 2010.

Grieger et al., Adeno-associated virus as a gene therapy vector: vector development, production and clinical applications, Advances in Biochemical Engineering/Biotechnology, vol. 99:119-45, Oct. 2005.

Haskell et al., Viral-mediated delivery of the late-infant neuronal ceroid lipofuscinosis gene, TPP-I to the mouse central nervous system, Gene Therapy, vol. 10(1):34-42, Jan. 2003.

Haurigot et al., Whole Body Correction of Mucopolysaccharidosis IIIA By Intracerebrospinal Fluid Gene Therapy, Journal Clinical Investigation, vol. 123(8):3254-3271, Aug. 2013.

Hinderer et al., Delivery of an adeno-associated virus vector into cerebrospinal fluid attenuates central nervous system disease in Mucopolysaccharidosis Type II mice, Human Gene Therapy, vol. 27(22):906-915, Nov. 2016.

Hinderer et al., Neonatal tolerance induction enables accurate evaluation of gene therapy for MPS I in a canine model, Molecular Genetics and Metabolism, vol. 119(1-2):124-130, Sep. 2016.

Hinderer et al., Evaluation of intrathecal routes of administration for adeno-associated viral vectors in large animals, Human Gene Therapy, vol. 29(1):15-24, Jan. 2018.

Hinderer et al., Intrathecal Gene Therapy Corrects CNS Pathology In A Feline Model Of Mucopolysaccharidosis I, Molecular Therapy, vol. 22(12):2018-27, Dec. 2014.

Hinderer et al., Severe Toxicity in Nonhuman Primates and Piglets Following High-Dose Intravenous Administration of an Adeno-Associated Virus Vector Expressing Human SMN, Mar. 2018;29(3):285-298.

Hinderer et al., Widespread Gene Transfer In The Central Nervous System Of Cynomolgus Macaques Following Delivery Of AAV9 Into The Cisterna Magna, Molecular Therapy—Methods & Clinical Development, vol. 1:14051, Dec. 2014.

Hordeaux et al., Toxicology study of intra-cisterna magna adeno-associated virus 9 expressing human alpha-L-iduronidase in Rhesus Macaques, Molecular Therapy, vol. 10:79-88, Jul. 2018.

Katz et al. Enzyme replacement therapy attenuates disease progression in a canine model of late-infantile neuronal ceroid lipofuscinosis (CLN2 disease), Journal Of Neuroscience Research, vol. 92(11):1591-1598, Nov. 2014.

Katz et al., AAV Gene Transfer Delays Disease Onset in a TTP1-Deficient Canine Model of the Late Infantile Form of Batten Disease, Science Translational Medicine, vol. 7(313):313ra180, Nov. 2015.

Katz et al., Extraneuronal Pathology in a Canine Model of CLN2 Neuronal Ceroid Lipofuscinosis after Intracerebroventricular Gene Therapy that Delays Neurological Disease Progression, Gene Therapy, vol. 24(4): 215-223, Apr. 2017.

Kielar et al., Successive neuron loss in the thalamus and cortex in a mouse model of infantile neuronal ceroid lipofuscinosis, Neurobiology of Disease, vol. 25(1):150-162, Jan. 2007.

Kida et al., Cellular pathology and pathogenic aspects of neuronal ceroid lipofuscinoses. Batten Disease: Diagnosis, Treatment, And Research, Advances in Genetics, vol. 45:35-68, 2001.

Liu et al., Structural organization and sequence of CLN2, the defective gene in classical late infantile neuronal ceroid lipofuscinosis, Genomics, vol. 50(2):206-12, Jun. 1998.

Lock et al., Absolute determination of single-stranded and self-complementary adeno-associated viral vector genome titers by droplet digital PCR, Human Gene Therapy Methods, vol. 25(2):115-25, Apr. 2014.

Macauley et al., Cerebellar pathology and motor deficits in the palmitoyl protein thioesterase 1-deficient mouse, Experimental Neurology, vol. 217(1):124-135, May 2009.

Mccarty et al., Self-complementary recombinant adeno-associated virus (scAAV) vectors promote efficient transduction independently of DNA synthesis, Gene Therapy, vol. 8(16):1248-54, Aug. 2001.

(56) References Cited

OTHER PUBLICATIONS

Mclaughlin et al., Adeno-associated virus general transduction vectors: analysis of proviral structures., Journal of Virology, vol. 62(6):1963-1973, Jun. 1988.
Mignon et al., Antibiotic-free selection in biotherapeutics: now and forever, Pathogens, vol. 4(2):157-181, Jun. 2015.
Nathwani et al., Enhancing transduction of the liver by adeno-associated viral vectors, Gene Therapy, vol. 16(1): 60-69, Jan. 2009.
NCBI Reference Sequence: NM_000391.3, *Homo sapiens* tripeptidyl peptidase 1 (TPP1), mRNA, Apr. 29, 2017.
NCBI Reference Sequence: NP_000382.3, tripeptidyl-peptidase 1 preproprotein [*Homo sapiens*], Apr. 29, 2017.
Nickel et al., Natural history of CLN2 disease: Quantitative assessment of disease characteristics and rate of progression, Neuropediatrics, vol. 47 :Fv04-3, Apr. 2016.
UniProtKB-O14773 (TPP1_Human), accessed Oct. 22, 2016.
Mizukami et al., A Protocol for AAV vector production and purification, Division of Genetic Therapeutics, Center for Molecular Medicine, 1998.
Paneda et al., Effect of adeno-associated virus serotype and genomic structure on liver transduction and biodistribution in mice of both genders. Human Gene Therapy, vol. 20(8):908-917, Aug. 2009.
Passini et al., AAV2- and AAV5-mediated CNS delivery of human CLN2 reduces lysosomal storage in a mouse model of late infant neuronal ceroid lipofuscinosis, Abstract, Molecular Therapy, vol. 1(1):S166, May 2005.
Passini, M., Intracranial delivery of CLN2 reduces brain pathology in a mouse model of classical late infant neuronal ceroid lipofuscinosis, Journal of Neuroscience, vol. 26(5):1334-1342, Feb. 2006.
Passini et al., Translational fidelity of intrathecal delivery of self-complementary AAV9-survival motor neuron 1 for spinal muscular aropy, Human Gene Therapy, vol. 25(7):619-630, Jul. 2014.
Pontikis et al., Late onset neurodegeneration in the Cln3−/− mouse model of juvenile neuronal ceroid lipofuscinosis is preceded by low level glial activation, Brain Research, vol. 1023(2):231-242, Oct. 2004.
Schulz et al., NCL diseases—clinical perspectives, Biochemistry Et Biophysica Acta (BBA)—Molecular Basis Of Disease, vol. 1832(11):1801-1806, Nov. 2013.
Schulz et al., Study of intraventricular Cerliponase Alfa for CLN2 disease, New England Journal of Medicine, vol. 378(80):1898-1907, Apr. 2018.
Sleat et al., Association of mutations in a lysosomal protein with classical late-infantile neuronal ceroid lipofuscinosis, Science, vol. 277(5333):1802-1805, Sep. 1997.
Sleat et al., Mutational Analysis of the Defective Protease in Classic Late-Infant Neuronal Ceroid Lipofuscinosis, a Neurodegenerative Lysosomal Storage Disorder, The American Journal of Human Genetics, vol. 64(6):1511-1523, Jun. 1999.
Sleat et al., Analysis of large-scale whole exome sequencing data to determine the prevalence of genetically-distinct forms of neuronal ceroid lipofuscinosis, Gene, vol. 593(2):284-291, Nov. 2016.
Sleat et al., A Mouse Model Of Classical Late-Infantile Neuronal Ceroid Lipofuscinosis Based On Targeted Disruption Of The CLN2 Gene Results In A Loss Of Tripeptidyl-Peptidase I Activity And Progressive Neurodegeneration, Journal of Neuroscience, vol. 24(41):9117-9126, Oct. 2004.
Snyder et al., Comparison Of Adeno-Associated Viral Vector Serotypes For Spinal Cord And Motor Neuron Gene Delivery. Human Gene Therapy, vol. 22(9):1129-1135, Sep. 2011.
Sochor et al., An Autogenously Regulated Expression System for Gene Therapeutic Ocular Applications, Scientific Reports, vol. 24(5):17105, Nov. 2015.
Sohar et al., Enzyme-based diagnosis of classical late infantile neuronal ceroid lipofuscinosis: comparison of tripeptidyl peptidase I and pepstatin-insensitive protease assays, Clinical Chemistry, vol. 46(7):1005-1008, Jul. 2000.
Sohar et al., Biochemical Characterization of a Lysosomal Protease Deficient in Classical Late Infant Neuronal Ceroid Lipofuscinosis (LINCL) and Development of an Enzyme-Based Assay for Diagnosis and Exclusion of LINCL in Human Specimens and Animal Models, Journal Of Neurochemistry, vol. 73(2):700-711, Aug. 1999.
Sofronescu, Cerebrospinal Fluid Analysis, MedScape, Aug. 9, 2015.
Sondhi et al., Enhanced Survival of the LINCL Mouse Following CLN2 Gene Transfer Using the rh.10 Rhesus Macaque-derived Adeno-associated Virus Vector, Molecular Therapy, vol. 15(3):481-491, Mar. 2007.
Sondhi et al., Survival advantage of neonatal CNS gene transfer for late infant neuronal ceroid lipofuscinosis, Experimental Neurology, vol. 213(1):18-27, Sep. 2008.
Sondhi et al., Long-Term Expression and Safety of AAVrh.10hCLN2 to the Brain of Rats and Nonhuman Primates for the Treatment of Late Infantile Neuronal Ceroid Lipofuscinosis, Human Gene Therapy Methods, vol. 23(5):324-335, Oct. 2012.
Sondhi et al., Slowing late infantile Batten disease by direct brain parenchymal administration of a rh.10 adeno-associated virus expressing CLN2, Science Translational Medicine, vol. 12, eabb5413, Dec. 2020.
Su et al., In Vitro and In Vitro mRNA Delivery using Lipid-Enveloped pH-Responsive Polymer Nanoparticles, Molecular Pharmaceutics, vol. 8(3):774-87, Jun. 2011.
Thelen et al., Disruption of the autophagy-lysosome pathway is involved in neuropathology of the nclf mouse model of neuronal ceroid lipofuscinosis, PLoS One, vol. 7(4): e35493, 2012.
Thompson et al., A Comprehensive Comparison of Multiple Sequence Alignments, Nucleic Acids Research, vol. 27(13):2682-2690, 1999.
Warrier et al., Genetic basis and phenotypic correlations of the neuronal ceroid lipofuscinoses, Biochimica et Biophysica Acta, vol. 1832(11):1827-30, Nov. 2013.
Williams et al., Management Strategies for CLN2 Disease, Pediatric Neurology, vol. 69:102-112, Apr. 2017.
Wlodawer et al., A model of tripeptidyl-peptidase I (CLN2), a ubiquitous and highly conserved member of the sedolisin family of serine-carboxyl peptidases, BMC Structure Biology, vol. 3 :8, Nov. 2003.
Worgall et al, Treatment of Late Infant Neuronal Ceroid Lipofuscinosis by CNS Administration of a Serotype 2 Adeno-Associated Virus Expressing CLN2 cDNA, Human Gene Therapy, vol. 19(5):463-474, May 2008.
Worgall et al., Neurological deterioration in late infantile neuronal ceroid lipofuscinosis, Neurology, vol. 69(6):521-35, Aug. 2007.
Wyrwich et al., An Adapted Clinical Measurement Tool for the Key symptoms of CLN2 Disease, Journal of Inborn Errors of Metabolism & Screening, vol. 6:1-7, Jul. 2018.
Xiong, PCR-based accurate synthesis of long DNA sequences, Nature Protocols, vol. 1(7):791-7, Jul. 2006.
Young, Two-step total gene synthesis method, Nucleic Acids Research, vol. 32(7):e59, Apr. 2004.
Yu et al., Recent patents on oligonucleotide synthesis and gene synthesis, Recent Advances in DNA & Gene Sequences, vol. 6(1):10-21, Apr. 2012.
Zhang et al., Adenovirus-adeno-associated virus hybrid for large-scale recombinant adeno-associated virus production, Human Gene Therapy, vol. 20(9):922-9, Sep. 2009.
Zhong et al., Two common mutations in the CLN2 gene underlie late infantile neuronal ceroid lipofuscinosis, Clinical Genetics, vol. 54(3):234-238, Sep. 1998.
Weill Medical College of Cornell University. AAVRh.10 Administered to Children With Late Infantile Neuronal Ceroid Lipofuscinosis. ClinicalTrials.gov Identifier: NCT01414985. First Posted: Aug. 11, 2011. (accessed Dec. 23, 2022).
Weill Medical College of Cornell University. Safety Study of a Gene Transfer Vector (Rh.10) for Children With Late Infantile Neuronal Ceroid Lipofuscinosis (LINCL). ClinicalTrials.gov Identifier: NCT01161576. First Posted: Jul. 13, 2010. (accessed Dec. 23, 2022).
Weill Medical College of Cornell University, Safety Study of a Gene Transfer Vector for Children With Late Infantile Neuronal Ceroid Lipofuscinosis, ClinicalTrials.gov Identifier: NCT00151216. First Posted: Sep. 8, 2005. (accessed Dec. 23, 2022).
International Search Report and Written Opinion for International Patent Application No. PCT/US2018/32278, mailed Jul. 27, 2018.

(56) References Cited

OTHER PUBLICATIONS

Extended Search Report in European Patent Application No. 18798476.0, dated May 17, 2021.
Office Action in Japanese Patent Application No. 2019-562418, dated Mar. 3, 2022, with English translation provided by local agent.
Office Action in Japanese Patent Application No. 2019-562418, dated Sep. 28, 2022, with English translation provided by local agent.
Office Action in Israeli Patent Application No. 270422, dated Dec. 14, 2022.
Office Action in Korean Patent Application No. 10-2019-7036041, dated Feb. 10, 2023.

* cited by examiner

| FIG 4B | WT M | WT F | KO M | KO F | KO+3e9 M | KO+3e9 F | KO+3e11 M | KO+3e11 F |
|---|---|---|---|---|---|---|---|---|
| Median survival (w.) | Undefined | Undefined | 15 | 24 | 16 | 19 | Undefined | Undefined |

FIG. 13A

```
CLUSTAL O(1.2.4) multiple sequence alignment - 78.56% identity

TPP1_native     atgggactccaagcctgcctcctagggctcttgccctcatcctctctggcaaatgcagt     60
TPP1_co         atgggactgcaggcctgtctgctgggactgttcgccctgatcctgagcggcaagtgcagc     60
                ******** ** ***** ** ** ** ** ** ***** *****   ***** *****

TPP1_native     tacagcccggagcccgaccagcggaggacgctgccccaggctgggtgtccctgggccgt     120
TPP1_co         tacagcccgagcccgaccagagaagaacactgcctccaggctgggtgtccctgggcaga    120
                ******** ************ *  **  ***** ****************** *

TPP1_native     gcggaccctgaggaagagctgagtctcacctttgccctgagacagcagaatgtggaaaga    180
TPP1_co         gctgaccctgaagaggaactgagcctgaccttcgccctgcggcagcagaacgtggaaaga    180
                ** ******** ** ** ***** ** ***** ****** * ******** *********

TPP1_native     ctctcggagctggtgcaggctgtgtcggatcccagctctcctcaatacggaaaataccctg    240
TPP1_co         ctgagcgagctggtgcaggccgtgtccgatcctagcagccctcagtacggcaagtacctg    240
                **   *************** ***** ***** *  *  ***  ***** ** ******

TPP1_native     accctagagaatgtggctgatctggtgaggccatcccccactgaccctccacacggtgcaa    300
TPP1_co         accctggaaaacgtggccgacctcgtgcggcctagccctctgacactgcacaccgtgcag    300
                ***** ** ** ***** ** ** *** *** ***  *** ** ***** ** ***** *****

TPP1_native     aaatggctcttggcagccggagcccagaagtgccattctgtgatcacacaggactttctg    360
TPP1_co         aagtggctgctggctgccggcgctcagaaatgccactccgtgatcacccaggactttctg    360
                ** *****  **** ** *****  ** ***** ** ** ** ********* **************

TPP1_native     acttgctggctgagcatccgacaagcagagctgctgctgcctgggggctgagtttcatcac    420
TPP1_co         acctgttggctgagcatccggcaggccgaactgctgctgcctggggccgagtttcaccac    420
                ** ** *************  ** ** ** ******** ******** ******** ***

TPP1_native     tatgtgggaggacctacggaaacccatgttgtaaggtccccacatccctaccagcttcca    480
TPP1_co         tatgtgggcggacccaccgagacacatgtcgtgcgcagcccacaccttaccagctgcca    480
                ********  ****  ** ** ** ***** ** **  *  ****** *  ****** ***

TPP1_native     caggccttggcccccatgtggactttgtgggggggactgcaccgtttcccccaacatca    540
TPP1_co         caggctctggccctcacgtggactttgtgggaggcctgcacagattccccccaaccagc    540
                *****   ******* **  **********   * ** ****** * *  *** *** *

TPP1_native     tccctgaggcaacgtcctgagccgcaggtgacagggactgtaggcctgcatctggggta    600
TPP1_co         agcctgagacagaggcctgagccacaagtgaccggcacagtgggcctgcatctgggcgtg    600
                  ****** **  * ******** ** ***** **  ** ************ **

TPP1_native     accccctctgtgatccgtaagcgatacaacttgacctcacaagacgtgggctctggcacc    660
TPP1_co         acacctagcgtgatccggaagcggtacaacctgaccagccaggatgtgggcagcggcacc    660
                ** **   ******** ***** ******* ****  ** ** ** ***** ** ******

TPP1_native     agcaataacagccaagcctgtgcccagttcctggagcagtatttccatgactcagacctg    720
TPP1_co         agcaacaatagccaggcctgcgcccagttcctggaacagtacttccacgacagcgatctg    720
                ***** ** ***** ***** ************** ***** ***** ***  ** ***

TPP1_native     gctcagttcatgcgcctcttcggtggcaactttgcacatcaggcatcagtagcccgtgtg    780
TPP1_co         gcccagttcatgcggctgttcggcggcaacttcgcacatcaggctagcgtggccagagtc    780
                ** ***********  ** ***** *******  ***  ********  ** *** * **

TPP1_native     gttggacaacagggccggggccgggccgggattgaggccagtctagatgtgcagtacctg    840
TPP1_co         gtgggccagcagggaagaggcagagccggaattgaggcctccctggacgtgcagtacctg    840
                ** **  ** ***** * *  * * ****** ******    ** ** ************

TPP1_native     atgagtgctggtgccaacatctccacctgggtctacagtagccctggccggcatgaggga    900
TPP1_co         atgagcgctggcgccaacatcagcacctgggtgtacagcagccccggcagacacgagggc    900
                ***** *****  ******** ********** ***** *****  *** ** **  ***

TPP1_native     caggagcccttcctgcagtggctcatgctgctcagtaatgagtcagccctgccacatgtg    960
TPP1_co         caggaacctttcctgcagtggctgatgctgctgagcaacgagagcgccctgcctcatgtg    960
                *****  ** *** ********** ******** **  ** *** ******** ******
```

FIG. 13B

```
TPP1_native    catactgtgagctatggagatgatgaggactccctcagcagcgcctacatccagcgggtc    1020
TPP1_co        cacacagtgtcctacggcgacgacgaggacagcctgagcagcgcctacatccagagagtg    1020
               ** ** ***  *** ** ** ** ******  *** ******************  * **

TPP1_native    aacactgagctcatgaaggctgccgctcggggtctcaccctgctcttcgcctcaggtgac    1080
TPP1_co        aacaccgagctgatgaaggccgctgccaggggactgaccctgctgtttgcctctggcgat    1080
               ***** ***** ******** ***** * **** ** ******** ** ***** ** **

TPP1_native    agtggggccgggtgttggtctgtctctggaagacaccagttccgccctaccttccctgcc    1140
TPP1_co        agcggagccggctgttggagtgtgtcaggccggcaccagttcagacccaccttcctgcc    1140
               ** ** ***** ******    *** ** **  * ********* * ** ***** ******

TPP1_native    tccagccctatgtcaccacagtgggaggcacatccttccaggaacctttcctcatcaca    1200
TPP1_co        agctcccctacgtgacaaccgtgggcggcacctcctttcaggaaccccttcctgatcacc    1200
                 *  ***** ** ** ** ***** ***** ***** ******* ** ***** *****

TPP1_native    aatgaaattgttgactatatcagtggtggtggcttcagcaatgtgttcccacggccttca    1260
TPP1_co        aacgagatcgtggactacatcagcggcggaggcttcagcaacgtgttccccagacccagc    1260
               ** ** ** ***** ** ***** **  * *********** ******** *   ***

TPP1_native    taccaggaggaagctgtaacgaagttcctgagctctagcccccacctgccaccatccagt    1320
TPP1_co        taccaggaagaggccgtgaccaagttcctgtcctccagccctcatctgccccccagctcc    1320
               ********  **  ** ** ** ********    ***** *** ***  ******

TPP1_native    tacttcaatgccagtggccgtgcctaccagatgtggctgcactttctgatggctactgg    1380
TPP1_co        tacttcaacgccagcggcagagcctacccagatgtggccgctctgtccgacggctactgg    1380
               ********  ***** ***  *  ********  ** ** ** **  * **********

TPP1_native    gtggtcagcaacagagtgcccattccatgggtgtccggaacctcggcctctactccagtg    1440
TPP1_co        gtggtgtccaacagagtgcccatcccttgggtgtccggcacaagcgccagcaccccctgtg    1440
               *****   *************** **  ********* *         *** ** ** ***

TPP1_native    tttgggggatcctatccttgatcaatgagcacaggatccttagtggccgccccctctt    1500
TPP1_co        tttggcggcatcctgtccctgatcaacgagcacagaatcctgtccggcagacccccccctg    1500
               ***** **  ***** *** ******  ******** *****   *** *** ******

TPP1_native    ggctttctcaacccaaggctctaccagcagcatggggcaggactctttgatgtaacccgt    1560
TPP1_co        ggcttcctgaaccctagactgtaccagcagcacggcgctggcctgttcgatgtgaccaga    1560
               ***** ** *****  *     ********** ** **  ** **** **** ** *

TPP1_native    ggctgccatgagtcctgtctggatgaagaggtagagggccagggttctgctctggtcct    1620
TPP1_co        ggctgccacgagagctgcctggacgaggaagtggaggccagggcttctgttctggccct    1620
               ********  ***  *** ***** ** ** ** **   ***  ****** ***** ***

TPP1_native    ggctgggatcctgtaacaggctggggaacacccaacttccagctttgctgaagactcta    1680
TPP1_co        ggctgggatcctgtgaccggatggggcaccctaacttccccgcctgctgaaaacactg    1680
               **************  **  *****  ** ** ******* * *  ******  ** **

TPP1_native    ctcaaccctgac    1693
TPP1_co        ctgaaccctgat    1693
               ** *********
```

FIG 17
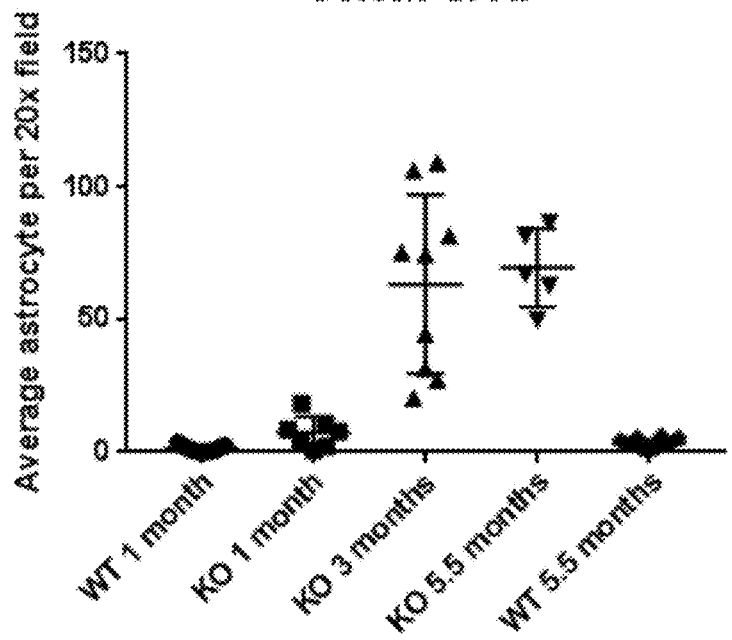
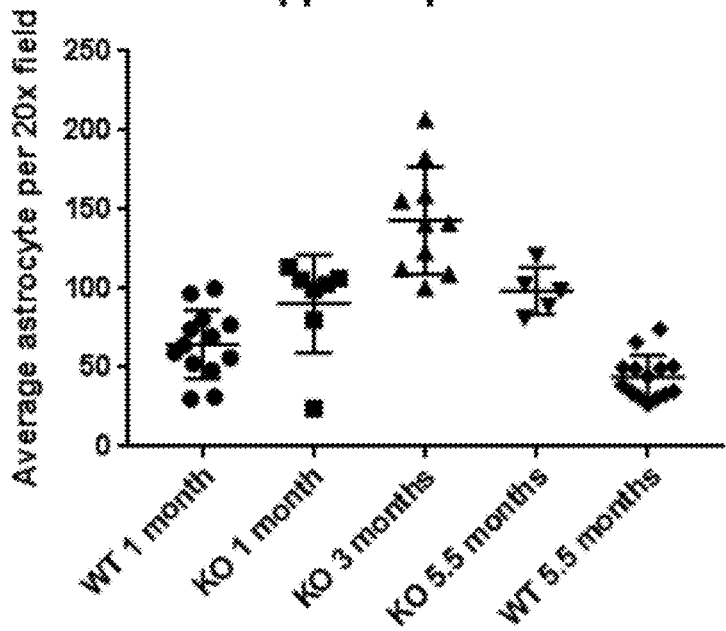

| KO PBS | KO AAV9 | WT PBS |

GENE THERAPY FOR CEROID LIPOFUSCINOSES

CROSS-REFERENCE TO RELATED APPLICATIONS

This is a continuation of U.S. patent application Ser. No. 16/611,512 filed Nov. 7, 2019, which is a national stage application under 35 USC 371 of PCT/US2018/032278, filed May 11, 2018, which claims the benefit under 35 USC 119(e) of U.S. Provisional Patent Application No. 62/504,817, filed May 11, 2017, U.S. Provisional Patent Application No. 62/599,816, filed Dec. 18, 2017, and U.S. Provisional Patent Application No. 62/652,006, filed Apr. 3, 2018. Each of these applications is hereby incorporated by reference in its entirety.

INCORPORATION-BY-REFERENCE OF MATERIAL SUBMITTED IN ELECTRONIC FORM

Applicant hereby incorporates by reference the Sequence Listing material filed in electronic form herewith. This file is labeled "UPN-17-8151.US.C1_Seq".

BACKGROUND OF THE INVENTION

The neuronal ceroid lipofuscinoses (NCLs) are a group of rare and inherited neurodegenerative disorders. They are considered the most common of the neurogenetic storage diseases, with the accumulation of autofluorescent lipopigments resembling ceroid and lipofuscin seen in patients. NCLs are associated with variable, yet progressive, symptoms, including abnormally increased muscle tone or spasm, blindness or vision problems, dementia, lack of muscle coordination, intellectual disability, movement disorder, seizures and unsteady walk. The frequency of this disease is approximately 1 per 12,500 individuals. There are three main types of NCL: adult (Kufs or Parry disease); juvenile and late infantile (Jansky-Bielschowsky disease). The neuronal ceroid lipofuscinoses (NCLs) originally were defined by their age of onset and clinical symptoms (as noted herein). However, they have since been reclassified on the basis of newer molecular findings, which have provided evidence of far more overlap for the different genetic variants than had previously been suggested by the clinical phenotypes.

At least twenty genes have been identified in association with NCL. NCL patients with CLN2 mutations are deficient in a pepstatin-insensitive lysosomal peptidase called tripeptidyl peptidase 1 (TTP1). TTP1 removes tripeptides from the N-terminal of polypeptides. Mutations have been reported in all 13 exons of the CLN2 gene. Some mutations result in a more protracted course. Although onset is usually in late infancy, later onset has been described. More than 58 mutations have been described in CLN2.

CLN2 disease, a form of Batten disease, is a rare lysosomal storage disorder (LSD) with an estimated incidence of 0.07-0.51 per 100,000 live births (Augestad et al., 2006; Claussen et al., 1992; Mole et al., 2013; National Batten Disease Registry; Poupetova et al., 2010; Santorelli et al., 2013; Teixeira et al., 2003). CLN2 disease is a fatal autosomal recessive neurodegenerative LSD caused by mutations in the CLN2 gene, located on chromosome 11q15 and encoding for the soluble lysosomal enzyme tripeptidyl-peptidase-1 (TPP1). Mutations in the CLN2 gene, and subsequent deficiency in TPP1 enzymatic activity, result in lysosomal accumulation of storage material and neurodegeneration of the brain and retina (Liu et al., 1998; Wlodawer et al., 2003). CLN2 disease is characterized by early onset at 2-4 years of age with initial features usually including recurrent seizures (epilepsy) and difficulty coordinating movements (ataxia). The disease also results in the loss of previously acquired skills (developmental regression). Epilepsy is often refractory to medical therapy, and the general decay of psychomotor functions is rapid and uniform between the third and fifth birthday (Schulz et al., 2013) before premature death by mid-childhood (Nickel M et al., 2016; Worgall et al., 2007).

Enzyme replacement therapy (ERT) with recombinant TPP1 (Brineura® cerliponase alfa, BioMarin Pharmaceuticals) was recently approved in the United States (US) and European Union (EU) for the treatment of CLN2 disease and is administered as a biweekly infusion into the lateral ventricles via a permanently implanted device. The clinical benefit of Brineura® was designated to be limited to stabilization of motor function by the FDA, while the European Medicines Agency (EMA) determined that there was a positive impact on language skills as well (Brineura®, FDA Summary Basis of Approval; Brineura® European Public Assessment Report [EPAR]; Schulz et al., 2016). Brineura® requires specialized expertise for the implantation of a port directly into the brain and must be administered during a 4-hour infusion every two weeks in a healthcare setting by a trained professional knowledgeable in intracerebroventricular (ICV) administration. Repeat infusions are necessary in part due to the short CSF and lysosomal half-lives of Brineura® which are estimated to be 7 hours and 11.5 days, respectively (Brineura®, EPAR). Thus, there remains a significant unmet need for new therapies that can provide durable and long-term TPP1 enzymatic activity in the central nervous system (CNS) of patients with CLN2 disease, without the high patient burden and morbidities associated with repeat administration of ERT. Therefore, compositions useful for delivering and expressing TPP1 in subjects in need for treating CLN2 disease are needed. A one-time administration of recombinant adeno-associated virus (rAAV) expressing canine TPP1 (rAAV2.caTPP1) was shown to result in high expression of TPP1 predominantly in ependymal cells and secretion of the enzyme into the cerebrospinal fluid leading to clinical benefit. See Katz et al, Sci Transl Med. 2015 Nov. 11; 7(313): 313ra180; and KATZ, et al, Gene therapy 2017 February 24(4): 215-223, which are incorporated herein by reference. However AAV2 does not penetrate the brain parenchyma and does not target neurons, thus limiting the expected benefits compared to what can be achieved with novel neurotropic AAVs.

SUMMARY OF THE INVENTION

Provided herein in one aspect, is a codon optimized, engineered nucleic acid sequence of SEQ ID NO: 3 encoding human tripeptidyl peptidase1 (TPP1).

In another aspect, provided herein is an expression cassette comprising the codon optimized CLN2 nucleic acid sequence SEQ ID NO: 3 encoding human TPP1. In one embodiment, the codon optimized human CLN2, is at least 70% identical to the native human coding sequence of SEQ ID NO: 2. The alignment of SEQ ID NO: 2 (native) and SEQ ID NO: 3 (codon optimized) is provided in FIGS. 15A-15B.

In another aspect, a recombinant adeno-associated virus (rAAV) is provided. In one embodiment, the rAAV includes an AAV capsid, and a vector genome packaged therein, said vector genome comprising: (a) an AAV 5' inverted terminal repeat (ITR) sequence; (b) a promoter; (c) a CLN2 coding sequence encoding a human TPP1; and (d) an AAV 3' ITR.

In one aspect, a composition is provided which includes any of the rAAV as described herein and a pharmaceutical acceptable carrier or excipient. In one embodiment, the composition is suitable for intracerebroventricular (ICV) or intrathecal (IT) delivery.

In yet another aspect, an aqueous suspension suitable for administration to subject having Batten disease is provided. In one embodiment, the suspension includes an aqueous suspending liquid and about $7.5 \times 10^{12}$ GC ($7.5 \times 10^9$ GC/gram of brain) to about $1 \times 10^{15}$ GC ($1 \times 10^{12}$ GC/gram of brain) or viral particles of a recombinant adeno-associated virus (rAAV) useful as a therapeutic for Batten, said rAAV having an AAV capsid, and having packaged therein a vector genome comprising: (a) an AAV 5' inverted terminal repeat (ITR) sequence; (b) a promoter; (c) a CLN2 coding sequence encoding a human TPP1; and (d) an AAV 3' ITR.

In another aspect, a method of treating a subject having Batten with a rAAV as described herein is provided.

Other aspects and embodiments will be readily apparent based on the information described herein.

BRIEF DESCRIPTION OF THE DRAWINGS

FIG. 4B provides the median survival calculated based on the data shown in FIG. 4A.

FIGS. 13A and 13B provide the alignment of SEQ ID NO: 2 (native) and SEQ ID NO: 3 (codon optimized) of the TPP1 sequences.

FIG. 17 shows progressive astrocytosis observed in the cortex and hippocampus of Tpp1m1j mice, as early as 1-month of age (pre-symptomatic). Results (GFAP score) are average number of astrocyte per 20× power field. *** unpaired Mann Whitney test.

FIG. 18A: At 11 weeks post-injection, motor coordination assay suggests correction of the phenotype for high-dose animals, but not for low-dose or untreated TPP11m1J control animals. Motor coordination is correlated to the latency to fall, recorded during a 180 seconds trial on a rocking Rotarod (10 rpm, change direction every rotation). FIG. 18B: At 20 weeks post-injection, motor learning assay performed on surviving animals showed no difference between WT controls and high-dose animals. Motor learning is correlated to the latency to fall, recorded on an accelerating Rotarod, 3 successive days (5 to 40 rpm in 300 sec). Dose levels depicted in figure are based on total/GC per animal and equivalent to 7.5×109 and 7.5×1011 GC/g brain mass. P-value by unpaired Mann Whitney test.

FIG. 19: WT and high-dose animals (there were no surviving low-dose animals for analysis).

FIG. 20: Increased TPP1 enzymatic activity following administration of AAV9.CB7.TPP1. In high-dose animals, TPP1 enzymatic activity was increased to supraphysiological levels in the cerebrum, cerebellum, and liver at 30 weeks post-injection. M=male; F=female; WT=wild-type littermate.

FIG. 22A shows survival, grouped by gender and treatment. FIG. 22B shows survival with genders combined.

DETAILED DESCRIPTION OF THE INVENTION

Figure 1A:
FIG. 1A is a schematic representation of the AAV.CB7.CI.hTPP1co.RBG vector genome. ITR represents an AAV2 inverted terminal repeat. CB7 represents a chicken beta actin promoter with cytomegalovirus enhancer. RBG PolyA represents a rabbit beta globin polyadenylation signal.

The methods and compositions described herein involve compositions and methods for delivering a CLN2 nucleic acid sequence encoding human tripeptidyl peptidase 1 (TPP1) protein to subjects in need thereof for the treatment of NCL. In one embodiment, such compositions involve codon optimization of the CLN2 coding sequence, such as that shown in SEQ ID NO: 3. It is desirable to increase the efficacy of the product, and thus, increase safety, since a lower dose of reagent may be used. Also encompassed herein are compositions which include the native CLN2 coding sequences, as shown in SEQ ID NO: 2.

The TPP1 gene, also known as CLN2, encodes Tripeptidyl-peptidase 1, a lysosomal serine protease with tripeptidyl-peptidase I activity. It is also thought to act as a non-specific lysosomal peptidase which generates tripeptides from the breakdown products produced by lysosomal proteinases and requires substrates with an unsubstituted N-terminus. As used herein, the terms "TPP1", "CLN2", and "Tripeptidyl-peptidase 1" are used interchangeably when referring to the coding sequence. The native nucleic acid sequence encoding human Tripeptidyl-peptidase 1 is reported at NCBI Reference Sequence NM_000391.3 and reproduced here in SEQ ID NO: 2. Two isoforms of human Tripeptidyl-peptidase 1 has been reported as UniProtKB/Swiss-Prot Accessions O14773-1 and O14773-2 (reproduced here as SEQ ID NOs: 1 and 4). Mutations in the CLN2 gene are associated with late-infantile NCL (LINCL) disease.

Described herein is an exemplary AAV.hTPP1co vector, which is sometimes referred to herein as AAV9.CB7.hCLN2. The use of these terms is interchangeable. In addition, where, in one embodiment, the AAV9.CB7.hCLN2 vector is referred to, alternate embodiments are contemplated utilizing the components as described herein.

In certain embodiments of this invention, a subject has neuronal ceroid lipofuscinosis (NCL), for which the components, compositions and methods of this invention are designed to treat. As used herein, the term "subject" as used herein means a mammalian animal, including a human, a veterinary or farm animal, a domestic animal or pet, and animals normally used for clinical research. In one embodiment, the subject of these methods and compositions is a human. Still other suitable subjects include, without limitation, murine, rat, canine, feline, porcine, bovine, ovine, non-human primate and others. As used herein, the term "subject" is used interchangeably with "patient".

The neuronal ceroid-lipofuscinoses (NCLs) are a group of inherited, neurodegenerative, lysosomal storage disorders characterized by progressive intellectual and motor deterioration, seizures, and early death. Visual loss is a feature of most forms. Clinical phenotypes have been characterized traditionally according to the age of onset and order of appearance of clinical features into infantile, late-infantile, juvenile, adult, and Northern epilepsy (also known as progressive epilepsy with mental retardation [EPMR]). There is however genetic and allelic heterogeneity; a proposed new nomenclature and classification system has been developed to take into account both the responsible gene and the age at disease onset; for example, CLN2 disease, classic late infantile. The first symptoms typically appear between age two and four years, usually starting with epilepsy, followed by regression of developmental milestones, myoclonic ataxia, and pyramidal signs. Visual impairment typically appears at age four to six years and rapidly progresses to light/dark awareness only. Life expectancy ranges from age six years to early teenage. As used herein, the term "Batten disease" is used to refer to a CLN2 disease, which is used interchangeably with "NCL".

In one aspect, a codon optimized, engineered nucleic acid sequence encoding human (h) TPP1 is provided. In certain embodiments, an engineered human (h) TPP1 cDNA is provided herein (as SEQ ID NO: 3), which was designed to maximize translation as compared to the native TPP1 sequence (SEQ ID NO: 2). Preferably, the codon optimized TPP1 coding sequence has less than about 80% identity, preferably about 75% identity or less to the full-length native TPP1 coding sequence (SEQ ID NO: 2). In one embodiment, the codon optimized TPP1 coding sequence has about 74% identity with the native TPP1 coding sequence of SEQ ID NO: 2. In one embodiment, the codon optimized TPP1 coding sequence is characterized by improved translation rate as compared to native TPP1 following AAV-mediated delivery (e.g., rAAV). In one embodiment, the codon optimized TPP1 coding sequence shares less than about 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61% or less identity to the full length native TPP1 coding sequence of SEQ ID NO: 2. In one embodiment, the codon optimized nucleic acid sequence is a variant of SEQ ID NO: 3. In another embodiment, the codon optimized nucleic acid sequence a sequence sharing about 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61% or greater identity with SEQ ID NO: 3. In one embodiment, the codon optimized nucleic acid sequence is SEQ ID NO: 3. In another embodiment, the nucleic acid sequence is codon optimized for expression in humans. In other embodiments, a different TPP1 coding sequence is selected.

The term "percent (%) identity", "sequence identity", "percent sequence identity", or "percent identical" in the context of nucleic acid sequences refers to the residues in the two sequences which are the same when aligned for correspondence. The length of sequence identity comparison may be over the full-length of the genome, the full-length of a gene coding sequence, or a fragment of at least about 500 to 5000 nucleotides, is desired. However, identity among smaller fragments, e.g. of at least about nine nucleotides, usually at least about 20 to 24 nucleotides, at least about 28 to 32 nucleotides, at least about 36 or more nucleotides, may also be desired.

Percent identity may be readily determined for amino acid sequences over the full-length of a protein, polypeptide, about 32 amino acids, about 330 amino acids, or a peptide fragment thereof or the corresponding nucleic acid sequence coding sequences. A suitable amino acid fragment may be at least about 8 amino acids in length, and may be up to about 700 amino acids. Generally, when referring to "identity", "homology", or "similarity" between two different sequences, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence.

Identity may be determined by preparing an alignment of the sequences and through the use of a variety of algorithms and/or computer programs known in the art or commercially available [e.g., BLAST, ExPASy; ClustalO; FASTA; using, e.g., Needleman-Wunsch algorithm, Smith-Waterman algorithm]. Alignments are performed using any of a variety of publicly or commercially available Multiple Sequence Alignment Programs. Sequence alignment programs are available for amino acid sequences, e.g., the "Clustal Omega", "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27(13):2682-2690 (1999).

Multiple sequence alignment programs are also available for nucleic acid sequences. Examples of such programs include, "Clustal Omega", "Clustal W", "CAP Sequence Assembly", "BLAST", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fasta™, a program in GCG Version 6.1. Fasta™ provides alignments and percent sequence identity of the regions of the best overlap between the query and search sequences. For instance, percent sequence identity between nucleic acid sequences can be determined using Fasta™ with its default parameters (a word size of 6 and the NOPAM factor for the scoring matrix) as provided in GCG Version 6.1, herein incorporated by reference.

Codon-optimized coding regions can be designed by various different methods. This optimization may be performed using methods which are available on-line (e.g., GeneArt), published methods, or a company which provides codon optimizing services, e.g., DNA2.0 (Menlo Park, CA). One codon optimizing method is described, e.g., in US International Patent Publication No. WO 2015/012924, which is incorporated by reference herein in its entirety. See also, e.g., US Patent Publication No. 2014/0032186 and US Patent Publication No. 2006/0136184. Suitably, the entire length of the open reading frame (ORF) for the product is modified. However, in some embodiments, only a fragment of the ORF may be altered. By using one of these methods, one can apply the frequencies to any given polypeptide sequence, and produce a nucleic acid fragment of a codon-optimized coding region which encodes the polypeptide.

A number of options are available for performing the actual changes to the codons or for synthesizing the codon-optimized coding regions designed as described herein. Such modifications or synthesis can be performed using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides are designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

By "engineered" is meant that the nucleic acid sequences encoding the TPP1 protein described herein are assembled and placed into any suitable genetic element, e.g., naked DNA, phage, transposon, cosmid, episome, etc., which transfers the TPP1 sequences carried thereon to a host cell, e.g., for generating non-viral delivery systems (e.g., RNA-based systems, naked DNA, or the like) or for generating viral vectors in a packaging host cell and/or for delivery to a host cells in a subject. In one embodiment, the genetic element is a plasmid. The methods used to make such engineered constructs are known to those with skill in nucleic acid manipulation and include genetic engineering, recombinant engineering, and synthetic techniques. See, e.g., Green and Sambrook, Molecular Cloning: A Laboratory Manual, Cold Spring Harbor Press, Cold Spring Harbor, NY (2012).

As used herein, the term "host cell" may refer to the packaging cell line in which a recombinant AAV is produced from a production plasmid. In the alternative, the term "host cell" may refer to any target cell in which expression of the coding sequence is desired. Thus, a "host cell," refers to a prokaryotic or eukaryotic cell that contains exogenous or heterologous DNA that has been introduced into the cell by any means, e.g., electroporation, calcium phosphate precipitation, microinjection, transformation, viral infection, transfection, liposome delivery, membrane fusion techniques, high velocity DNA-coated pellets, viral infection and protoplast fusion. In certain embodiments herein, the term "host cell" refers to the cells employed to generate and package the viral vector or recombinant virus. In other embodiments herein, the term "host cell" refers to cultures of CNS cells of various mammalian species for in vitro assessment of the compositions described herein. Still in other embodiments, the term "host cell" is intended to reference the brain cells of the subject being treated in vivo for Batten disease. Such host cells include epithelial cells of the CNS including ependyma, the epithelial lining of the brain ventricular system. Other host cells include neurons, astrocytes, oligoedendrocytes, and microglia.

As used herein, the term "treatment" or "treating" is defined encompassing administering to a subject one or more compounds or compositions described herein for the purposes of amelioration of one or more symptoms of Batten disease. "Treatment" can thus include one or more of reducing onset or progression of neuronal ceroid lipofuscinosis (NCL), preventing disease, reducing the severity of the disease symptoms, or retarding their progression, including the progression of blindness, removing the disease symptoms, delaying onset of disease or monitoring progression of disease or efficacy of therapy in a given subject.

In one embodiment, the nucleic acid sequence encoding TPP1 further comprises a nucleic acid encoding a tag polypeptide covalently linked thereto. The tag polypeptide may be selected from known "epitope tags" including, without limitation, a myc tag polypeptide, a glutathione-S-transferase tag polypeptide, a green fluorescent protein tag polypeptide, a myc-pyruvate kinase tag polypeptide, a His6 tag polypeptide, an influenza virus hemagglutinin tag polypeptide, a flag tag polypeptide, and a maltose binding protein tag polypeptide.

In another aspect, an expression cassette comprising a nucleic acid sequence that encodes TPP1 is provided. In one embodiment, the sequence is a codon optimized sequence. In another embodiment, the codon optimized nucleic acid sequence is SEQ ID NO: 3 encoding human TPP1.

As used herein, an "expression cassette" refers to a nucleic acid molecule which comprises the coding sequences for TPP1 protein, promoter, and may include other regulatory sequences therefor, which cassette may be packaged into the capsid of a viral vector (e.g., a viral particle). Typically, such an expression cassette for generating a viral vector contains the CLN2 sequences described herein flanked by packaging signals of the viral genome and other expression control sequences such as those described herein. For example, for an AAV viral vector, the packaging signals are the 5' inverted terminal repeat (ITR) and the 3' ITR. When packaged into the AAV capsid, the ITRs in conjunction with the expression cassette may be referred to herein as the "recombinant AAV (rAAV) genome" or "vector genome". In one embodiment, an expression cassette comprises a codon optimized nucleic acid sequence that encodes TPP1 protein. In one embodiment, the cassette provides the codon optimized CLN2 operatively associated with expression control sequences that direct expression of the codon optimized nucleic acid sequence that encodes TPP1 in a host cell.

In another embodiment, an expression cassette for use in an AAV vector is provided. In that embodiment, the AAV expression cassette includes at least one AAV inverted terminal repeat (ITR) sequence. In another embodiment, the expression cassette comprises 5' ITR sequences and 3' ITR sequences. In one embodiment, the 5' and 3' ITRs flank the codon optimized nucleic acid sequence that encodes TPP1, optionally with additional sequences which direct expression of the codon optimized nucleic acid sequence that encodes TPP1 in a host cell. Thus, as described herein, a AAV expression cassette is meant to describe an expression cassette as described above flanked on its 5' end by a 5'AAV inverted terminal repeat sequence (ITR) and on its 3' end by a 3' AAV ITR. Thus, this rAAV genome contains the minimal sequences required to package the expression cassette into an AAV viral particle, i.e., the AAV 5' and 3' ITRs. The AAV ITRs may be obtained from the ITR sequences of any AAV, such as described herein. These ITRs may be of the same AAV origin as the capsid employed in the resulting recombinant AAV, or of a different AAV origin (to produce an AAV pseudotype). In one embodiment, the ITR sequences from AAV2, or the deleted version thereof (ΔITR), are used for convenience and to accelerate regulatory approval. However, ITRs from other AAV sources may be selected. Where the source of the ITRs is from AAV2 and the AAV capsid is from another AAV source, the resulting vector may be termed pseudotyped. Typically, the AAV vector genome comprises an AAV 5' ITR, the TPP1 coding sequences and any regulatory sequences, and an AAV 3' ITR. However, other configurations of these elements may be suitable. A shortened version of the 5' ITR, termed ΔITR, has been described in which the D-sequence and terminal resolution site (trs) are deleted. In other embodiments, the full-length AAV 5' and 3' ITRs are used. Each rAAV genome can be then introduced into a production plasmid.

As used herein, the term "regulatory sequences", "transcriptional control sequence" or "expression control sequence" refers to DNA sequences, such as initiator sequences, enhancer sequences, and promoter sequences, which induce, repress, or otherwise control the transcription of protein encoding nucleic acid sequences to which they are operably linked.

As used herein, the term "operably linked" or "operatively associated" refers to both expression control sequences that are contiguous with the nucleic acid sequence encoding the TPP1 and/or expression control sequences that act in trans or at a distance to control the transcription and expression thereof.

In one aspect, a vector comprising any of the expression cassettes described herein is provided. As described herein, such vectors can be plasmids of variety of origins and are useful in certain embodiments for the generation of recombinant replication defective viruses as described further herein.

A "vector" as used herein is a nucleic acid molecule into which an exogenous or heterologous or engineered nucleic acid transgene may be inserted which can then be introduced into an appropriate host cell. Vectors preferably have one or more origin of replication, and one or more site into which the recombinant DNA can be inserted. Vectors often have means by which cells with vectors can be selected from those without, e.g., they encode drug resistance genes. Common vectors include plasmids, viral genomes, and (primarily in yeast and bacteria) "artificial chromosomes." Certain plasmids are described herein.

In one embodiment, the vector is a non-viral plasmid that comprises an expression cassette described thereof, e.g., "naked DNA", "naked plasmid DNA", RNA, and mRNA; coupled with various compositions and nano particles, including, e.g., micelles, liposomes, cationic lipid-nucleic acid compositions, poly-glycan compositions and other polymers, lipid and/or cholesterol-based-nucleic acid conjugates, and other constructs such as are described herein. See, e.g., X. Su et al, Mol. Pharmaceutics, 2011, 8 (3), pp 774-787; web publication: Mar. 21, 2011; WO2013/182683, WO 2010/053572 and WO 2012/170930, all of which are incorporated herein by reference. Such non-viral TPP1 vector may be administered by the routes described herein. The viral vectors, or non-viral vectors, can be formulated with a physiologically acceptable carrier for use in gene transfer and gene therapy applications.

In another embodiment, the vector is a viral vector that comprises an expression cassette described therein. "Virus vectors" are defined as replication defective viruses containing the exogenous or heterologous CLN2 nucleic acid transgene. In one embodiment, an expression cassette as described herein may be engineered onto a plasmid which is used for drug delivery or for production of a viral vector. Suitable viral vectors are preferably replication defective and selected from amongst those which target brain cells. Viral vectors may include any virus suitable for gene therapy, including but not limited to adenovirus; herpes virus; lentivirus; retrovirus; parvovirus, etc. However, for ease of understanding, the adeno-associated virus is referenced herein as an exemplary virus vector.

A "replication-defective virus" or "viral vector" refers to a synthetic or recombinant viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"-containing only the transgene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

In another embodiment, a recombinant adeno-associated virus (rAAV) vector is provided. The rAAV compromises an AAV capsid, and a vector genome packaged therein. The vector genome comprises, in one embodiment: (a) an AAV 5' inverted terminal repeat (ITR) sequence; (b) a promoter; (c) a coding sequence encoding a human TPP1; and (d) an AAV 3' ITR. In another embodiment, the vector genome is the expression cassette described herein. In one embodiment, the CLN2 sequence encodes a full length TPP1 protein. In one embodiment, the TPP1 sequence is the protein sequence of SEQ ID NO: 1. In another embodiment, the coding sequence is SEQ ID NO: 3 or a variant thereof.

Adeno-associated virus (AAV), a member of the Parvovirus family, is a small nonenveloped, icosahedral virus with single-stranded linear DNA genomes of 4.7 kilobases (kb) to 6 kb. Among known AAV serotypes are AAV1, AAV2, AAV3, AAV4, AAV5, AAV6, AAV7, AAV8, AAV9 and others. The ITRs or other AAV components may be readily isolated or engineered using techniques available to those of skill in the art from an AAV. Such AAV may be isolated, engineered, or obtained from academic, commercial, or public sources (e.g., the American Type Culture Collection, Manassas, VA). Alternatively, the AAV sequences may be engineered through synthetic or other suitable means by reference to published sequences such as are available in the literature or in databases such as, e.g., GenBank, PubMed, or the like. AAV viruses may be engineered by conventional molecular biology techniques, making it possible to optimize these particles for cell specific delivery of nucleic acid sequences, for minimizing immunogenicity, for tuning stability and particle lifetime, for efficient degradation, for accurate delivery to the nucleus, etc.

Fragments of AAV may be readily utilized in a variety of vector systems and host cells. Among desirable AAV fragments are the cap proteins, including the vp1, vp2, vp3 and hypervariable regions, the rep proteins, including rep 78, rep 68, rep 52, and rep 40, and the sequences encoding these proteins. Such fragments may be used alone, in combination with other AAV serotype sequences or fragments, or in combination with elements from other AAV or non-AAV viral sequences. As used herein, artificial AAV serotypes include, without limitation, AAV with a non-naturally occurring capsid protein. Such an artificial capsid may be generated by any suitable technique, using a novel AAV sequence of the invention (e.g., a fragment of a vp1 capsid protein) in combination with heterologous sequences which may be obtained from another AAV serotype (known or novel), non-contiguous portions of the same AAV serotype, from a non-AAV viral source, or from a non-viral source. An artificial AAV serotype may be, without limitation, a chimeric AAV capsid, a recombinant AAV capsid, or a "humanized" AAV capsid. In one embodiment, a vector contains AAV9 cap and/or rep sequences. See, U.S. Pat. No. 7,906, 111, which is incorporated by reference herein.

In one embodiment, an AAV vector having AAV9 capsid characterized by the amino acid sequence of SEQ ID NO: 6, is provided herein, in which a nucleic acid encoding a classic late infantile neuronal ceroid lipofuscinosis 2 (CLN2) gene under control of regulatory sequences directing expression thereof in patients in need thereof.

As used herein, an "AAV9 capsid" is characterized by DNAse-resistant particle which is an assembly of about 60 variable proteins (vp) which are typically expressed as alternative splice variants resulting in proteins of different length of SEQ ID NO: 6. See also Genbank Accession No. AAS99264.1, which is incorporated herein by reference. See, also U.S. Pat. No. 7,906,111 and WO 2005/033321. As used herein "AAV9 variants" include those described in, e.g., WO2016/049230, U.S. Pat. No. 8,927,514, US 2015/0344911, and U.S. Pat. No. 8,734,809. The amino acid sequence is reproduced in SEQ ID NO: 6 and the coding sequence is reproduced in SEQ ID NO: 7. In one embodiment, the AAV9 capsid includes a capsid encoded by SEQ ID NO: 7, or a sequence sharing at least about 90%, 95%, 95%, 98% or 99% identity therewith.

The largest protein, vp1, is generally the full-length of the amino acid sequence of SEQ ID NO: 6 (aa 1-736 of SEQ ID NO: 6). In certain embodiments, the AAV9 vp2 protein has the amino acid sequence of 138 to 736 of SEQ ID NO: 6. In certain embodiments, the AAV9 vp3 has the amino acid sequence of 203 to 736 of SEQ ID NO: 6. In certain embodiments, the vp 1, 2 or 3 proteins may be have truncations (e.g., 1 or more amino acids at the N-terminus or C-terminus). An AAV9 capsid is composed of about 60 vp proteins, in which vp1, vp2 and vp3 are present in a ratio of about 1 vp, to about 1 vp2, to about 10 to 20 vp3 proteins within the assembled capsid. This ratio may vary depending upon the production system used. In certain embodiments, an engineered AAV9 capsid may be generated in which vp2 is absent.

It is within the skill in the art to design nucleic acid sequences encoding this AAV9 capsid, including DNA (genomic or cDNA), or RNA (e.g., mRNA). In certain embodiments, the nucleic acid sequence encoding the AAV9 vp1 capsid protein is provided in SEQ ID NO: 7. In other embodiments, a nucleic acid sequence of 70% to 99.9% identity to SEQ ID NO: 7 may be selected to express the AAV9 capsid. In certain other embodiments, the nucleic acid sequence is at least about 75% identical, at least 80% identical, at least 85%, at least 90%, at least 95%, at least 97% identical, or at least 99% to 99.9% identical to SEQ ID NO: 7.

As used herein, the term "Glade" as it relates to groups of AAV refers to a group of AAV which are phylogenetically related to one another as determined using a Neighbor-Joining algorithm by a bootstrap value of at least 75% (of at least 1000 replicates) and a Poisson correction distance measurement of no more than 0.05, based on alignment of the AAV vp1 amino acid sequence. The Neighbor-Joining algorithm has been described in the literature. See, e.g., M. Nei and S. Kumar, Molecular Evolution and Phylogenetics, Oxford University Press, New York (2000). Computer programs are available that can be used to implement this algorithm. For example, the MEGA v2.1 program implements the modified Nei-Gojobori method. Using these techniques and computer programs, and the sequence of an AAV vp1 capsid protein, one of skill in the art can readily determine whether a selected AAV is contained in one of the clades identified herein, in another Glade, or is outside these clades. See, e.g., G Gao, et al, J Virol, 2004 June; 78(10): 6381-6388, which identifies Clades A, B, C, D, E and F, and provides nucleic acid sequences of novel AAV, GenBank Accession Numbers AY530553 to AY530629. See, also, WO 2005/033321. AAV9 is further characterized by being within Clade F. Other Clade F AAV include AAVhu31 and AAVhu32.

As used herein, relating to AAV, the term variant means any AAV sequence which is derived from a known AAV sequence, including those sharing at least 70%, at least 75%, at least 80%, at least 85%, at least 90%, at least 95%, at least 97%, at least 99% or greater sequence identity over the amino acid or nucleic acid sequence. In another embodiment, the AAV capsid includes variants which may include up to about 10% variation from any described or known AAV capsid sequence. That is, the AAV capsid shares about 90% identity to about 99.9% identity, about 95% to about 99% identity or about 97% to about 98% identity to an AAV capsid provided herein and/or known in the art. In one embodiment, the AAV capsid shares at least 95% identity with an AAV9 capsid. When determining the percent identity of an AAV capsid, the comparison may be made over any of the variable proteins (e.g., vp1, vp2, or vp3). In one embodiment, the AAV capsid shares at least 95% identity with the AAV9 over the vp1, vp2 or vp3.

As used herein, "artificial AAV" means, without limitation, an AAV with a non-naturally occurring capsid protein. Such an artificial capsid may be generated by any suitable technique, using a selected AAV sequence (e.g., a fragment of a vp1 capsid protein) in combination with heterologous sequences which may be obtained from a different selected AAV, non-contiguous portions of the same AAV, from a non-AAV viral source, or from a non-viral source. An artificial AAV may be, without limitation, a pseudotyped AAV, a chimeric AAV capsid, a recombinant AAV capsid, or a "humanized" AAV capsid. Pseudotyped vectors, wherein the capsid of one AAV is replaced with a heterologous capsid protein, are useful in the invention. In one embodiment, AAV2/9 and AAV2/rh.10 are exemplary pseudotyped vectors.

In another embodiment, a self-complementary AAV is used. "Self-complementary AAV" refers a plasmid or vector having an expression cassette in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

The term "exogenous" as used to describe a nucleic acid sequence or protein means that the nucleic acid or protein does not naturally occur in the position in which it exists in a chromosome, or host cell. An exogenous nucleic acid sequence also refers to a sequence derived from and inserted into the same host cell or subject, but which is present in a non-natural state, e.g. a different copy number, or under the control of different regulatory elements.

The term "heterologous" as used to describe a nucleic acid sequence or protein means that the nucleic acid or protein was derived from a different organism or a different species of the same organism than the host cell or subject in which it is expressed. The term "heterologous" when used with reference to a protein or a nucleic acid in a plasmid, expression cassette, or vector, indicates that the protein or the nucleic acid is present with another sequence or subsequence with which the protein or nucleic acid in question is not found in the same relationship to each other in nature.

In still another embodiment, the expression cassette, including any of those described herein is employed to generate a recombinant AAV genome.

In one embodiment, the expression cassette described herein is engineered into a suitable genetic element (vector) useful for generating viral vectors and/or for delivery to a host cell, e.g., naked DNA, phage, transposon, cosmid, episome, etc., which transfers the CLN2 sequences carried thereon. The selected vector may be delivered by any suitable method, including transfection, electroporation, liposome delivery, membrane fusion techniques, high velocity DNA-coated pellets, viral infection and protoplast fusion. The methods used to make such constructs are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, NY.

For packaging an expression cassette or rAAV genome or production plasmid into virions, the ITRs are the only AAV components required in cis in the same construct as the expression cassette. In one embodiment, the coding sequences for the replication (rep) and/or capsid (cap) are removed from the AAV genome and supplied in trans or by a packaging cell line in order to generate the AAV vector.

Methods for generating and isolating AAV viral vectors suitable for delivery to a subject are known in the art. See, e.g., U.S. Pat. Nos. 7,790,449; 7,282,199; WO 2003/042397; WO 2005/033321, WO 2006/110689; and U.S. Pat. No. 7,588,772 B2. In a one system, a producer cell line is transiently transfected with a construct that encodes a transgene flanked by ITRs and a construct(s) that encodes rep and cap. In a second system, a packaging cell line that stably supplies rep and cap is transiently transfected with a construct encoding the transgene flanked by ITRs. In each of these systems, AAV virions are produced in response to infection with helper adenovirus or herpesvirus, requiring the separation of the rAAVs from contaminating virus. More recently, systems have been developed that do not require infection with helper virus to recover the AAV—the required helper functions (i.e., adenovirus E1, E2a, VA, and E4 or herpesvirus UL5, UL8, UL52, and UL29, and herpesvirus polymerase) are also supplied, in trans, by the system. In these newer systems, the helper functions can be supplied by transient transfection of the cells with constructs that encode the required helper functions, or the cells can be engineered to stably contain genes encoding the helper functions, the expression of which can be controlled at the transcriptional or posttranscriptional level.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated, even if subsequently reintroduced into the natural system. Such polynucleotides could be part of a vector and/or such polynucleotides or polypeptides could be part of a composition, and still be isolated in that such vector or composition is not part of its natural environment.

In yet another system, the expression cassette flanked by ITRs and rep/cap genes are introduced into insect cells by infection with baculovirus-based vectors. For reviews on these production systems, see generally, e.g., Zhang et al., 2009, "Adenovirus-adeno-associated virus hybrid for large-scale recombinant adeno-associated virus production," Human Gene Therapy the contents of which is incorporated herein by reference in its entirety. Methods of making and using these and other AAV production systems are also described in the following U.S. patents, the contents of each of which is incorporated herein by reference in its entirety: U.S. Pat. Nos. 5,741,683; 6,057,152; 6,204,059; 6,268,213; 6,491,907; 6,660,514; 6,951,753; 7,094,604; 7,172,893; 7,201,898; 7,229,823; and 7,439,065. See generally, e.g., Grieger & Samulski, 2005, "Adeno-associated virus as a gene therapy vector: Vector development, production and clinical applications," Adv. Biochem. Engin/Biotechnol. 99: 119-145; Buning et al., 2008, "Recent developments in adeno-associated virus vector technology," J. Gene Med. and the references cited below, each of which is incorporated herein by reference in its entirety.

The methods used to construct any embodiment of this invention are known to those with skill in nucleic acid manipulation and include genetic engineering, recombinant engineering, and synthetic techniques. See, e.g., Green and Sambrook et al, Molecular Cloning: A Laboratory Manual, Cold Spring Harbor Press, Cold Spring Harbor, NY (2012). Similarly, methods of generating rAAV virions are well known and the selection of a suitable method is not a limitation on the present invention. See, e.g., K. Fisher et al, (1993) J. Virol., 70:520-532 and U.S. Pat. No. 5,478,745.

"Plasmids" generally are designated herein by a lower case p preceded and/or followed by capital letters and/or numbers, in accordance with standard naming conventions that are familiar to those of skill in the art. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

In one embodiment, the production plasmid is that described herein, or as described in WO2012/158757, which is incorporated herein by reference. Various plasmids are known in the art for use in producing rAAV vectors, and are useful herein. The production plasmids are cultured in the host cells which express the AAV cap and/or rep proteins. In the host cells, each rAAV genome is rescued and packaged into the capsid protein or envelope protein to form an infectious viral particle.

In one aspect, a production plasmid comprising an expression cassette described above is provided. In one embodiment, the production plasmid is that shown in FIG. 1B. This plasmid is used in the examples for generation of the rAAV-human codon optimized TPP1 vector. Such a plasmid is one that contains a 5' AAV ITR sequence; a selected promoter; a polyA sequence; and a 3' ITR; additionally, it also contains an intron sequence, such as the chicken beta-actin intron. An exemplary schematic is shown in FIG. 1A. In a further embodiment, the intron sequence keeps the rAAV vector genome with a size between about 3 kilobases (kb) to about 6 kb, about 4.7 kb to about 6 kb, about 3 kb to about 5.5 kb, or about 4.7 kb to 5.5 kb. An example of a production plasmid which includes the TPP1 encoding sequence can be found in SEQ ID NO: 5. In another embodiment, the production plasmid is modified to optimized vector plasmid production efficiency. Such modifications include addition of other neutral sequences, or inclusion of a lambda stuffer sequence to modulate the level of supercoil of the vector plasmid. Such modifications are contemplated herein. In other embodiments, terminator and other sequences are included in the plasmid.

In certain embodiments, the rAAV expression cassette, the vector (such as rAAV vector), the virus (such as rAAV), and/or the production plasmid comprises AAV inverted terminal repeat sequences, a codon optimized nucleic acid sequence that encodes TPP1, and expression control sequences that direct expression of the encoded proteins in a host cell. In other embodiments, the rAAV expression cassette, the virus, the vector (such as rAAV vector), and/or the production plasmid further comprise one or more of an intron, a Kozak sequence, a polyA, post-transcriptional regulatory elements and others. In one embodiment, the post-transcriptional regulatory element is Woodchuck Hepatitis Virus (WHP) Posttranscriptional Regulatory Element (WPRE).

The expression cassettes, vectors and plasmids include other components that can be optimized for a specific species using techniques known in the art including, e.g., codon optimization, as described herein. The components of the cassettes, vectors, plasmids and viruses or other compositions described herein include a promoter sequence as part of the expression control sequences. In another embodiment, the promoter is cell-specific. The term "cell-specific" means that the particular promoter selected for the recombinant vector can direct expression of the optimized TPP1 coding sequence in a particular cell or tissue type. In one embodiment, the promoter is specific for expression of the transgene in ependyma, the epithelial lining of the brain ventricular system. In another embodiment, the promoter is specific for expression in a brain cell selected from neurons, astrocytes, oligoedendrocytes, and microglia. In one embodiment, the promoter is modified to add one or more restriction sites to facilitate cloning.

In another embodiment, the promoter is a ubiquitous or constitutive promoter. An example of a suitable promoter is a hybrid chicken β-actin (CBA) promoter with cytomegalovirus (CMV) enhancer elements, such as the sequence shown in SEQ ID NO: 5 at nt 3396 to 4061. In another embodiment, the promoter is the CB7 promoter. Other suitable promoters include the human β-actin promoter, the human elongation factor-1α promoter, the cytomegalovirus (CMV) promoter, the simian virus 40 promoter, and the herpes simplex virus thymidine kinase promoter. See, e.g., Damdindorj et al, (August 2014) A Comparative Analysis of Constitutive Promoters Located in Adeno-Associated Viral Vectors. PLoS ONE 9(8): e106472. Still other suitable promoters include viral promoters, constitutive promoters, regulatable promoters [see, e.g., WO 2011/126808 and WO 2013/04943]. Alternatively a promoter responsive to physiologic cues may be utilized in the expression cassette, rAAV genomes, vectors, plasmids and viruses described herein. In one embodiment, the promoter is of a small size, under 1000 bp, due to the size limitations of the AAV vector. In another embodiment, the promoter is under 400 bp. Other promoters may be selected by one of skill in the art.

In a further embodiment, the promoter is selected from SV40 promoter, the dihydrofolate reductase promoter, a phage lambda (PL) promoter, a herpes simplex viral (HSV) promoter, a tetracycline-controlled trans-activator-responsive promoter (tet) system, a long terminal repeat (LTR) promoter, such as a RSV LTR, MoMLV LTR, BIV LTR or an HIV LTR, a U3 region promoter of Moloney murine sarcoma virus, a Granzyme A promoter, a regulatory sequence(s) of the metallothionein gene, a CD34 promoter, a CD8 promoter, a thymidine kinase (TK) promoter, a B19 parvovirus promoter, a PGK promoter, a glucocorticoid promoter, a heat shock protein (HSP) promoter, such as HSP65 and HSP70 promoters, an immunoglobulin promoter, an MMTV promoter, a Rous sarcoma virus (RSV) promoter, a lac promoter, a CaMV 35S promoter, a nopaline synthetase promoter, an MND promoter, or an MNC promoter. The promoter sequences thereof are known to one of skill in the art or available publically, such as in the literature or in databases, e.g., GenBank, PubMed, or the like.

In another embodiment, the promoter is an inducible promoter. The inducible promoter may be selected from known promoters including the rapamycin/rapalog promoter, the ecdysone promoter, the estrogen-responsive promoter, and the tetracycline-responsive promoter, or heterodimeric repressor switch. See, Sochor et al, An Autogenously Regulated Expression System for Gene Therapeutic Ocular Applications. Scientific Reports, 2015 Nov. 24; 5:17105 and Daber R, Lewis M., A novel molecular switch. J Mol Biol. 2009 Aug. 28; 391(4):661-70, Epub 2009 Jun. 21 which are both incorporated herein by reference in their entirety.

In other embodiments, the expression cassette, vector, plasmid and virus described herein contain other appropriate transcription initiation, termination, enhancer sequences, efficient RNA processing signals such as splicing and polyadenylation (polyA) signals; TATA sequences; sequences that stabilize cytoplasmic mRNA; sequences that enhance translation efficiency (i.e., Kozak consensus sequence); introns; sequences that enhance protein stability; and when desired, sequences that enhance secretion of the encoded product. The expression cassette or vector may contain none, one or more of any of the elements described herein.

Examples of suitable polyA sequences include, e.g., a synthetic polyA or from bovine growth hormone (bGH), human growth hormone (hGH), SV40, rabbit β-globin (RGB), or modified RGB (mRGB). In a further embodiment, the poly A has a nucleic acid sequence from nt 33 to 159 of SEQ ID NO: 5.

Examples of suitable enhancers include, e.g., the CMV enhancer, the RSV enhancer, the alpha fetoprotein enhancer, the TTR minimal promoter/enhancer, LSP (TH-binding globulin promoter/alpha1-microglobulin/bikunin enhancer), an APB enhancer, ABPS enhancer, an alpha mic/bik enhancer, TTR enhancer, en34, ApoE amongst others.

In one embodiment, a Kozak sequence is included upstream of the TPP1 coding sequence to enhance translation from the correct initiation codon. In another embodiment, CBA exon 1 and intron are included in the expression cassette. In one embodiment, the TPP1 coding sequence is placed under the control of a hybrid chicken β actin (CBA) promoter. This promoter consists of the cytomegalovirus (CMV) immediate early enhancer, the proximal chicken β actin promoter, and CBA exon 1 flanked by intron 1 sequences.

In another embodiment, the intron is selected from CBA, human beta globin, IVS2, SV40, bGH, alpha-globulin, beta-globulin, collagen, ovalbumin, p53, or a fragment thereof.

In one embodiment, the expression cassette, the vector, the plasmid and the virus contain a 5' ITR, chicken beta-actin (CBA) promoter, CMV enhancer, CBA exon 1 and intron, human codon optimized CLN2 sequence, rabbit globin poly A and 3' ITR. In a further embodiment, the expression cassette includes nt 1 to 4020 of SEQ ID NO: 9. In yet a further embodiment, the 5' ITR has a nucleic acid sequence from nt 3199 to nt 3328 of SEQ ID NO: 5 and the 3'ITR has a nucleic acid sequence from nt 248 to nt 377 of SEQ ID NO: 5. In a further embodiment, the production plasmid has a sequence of SEQ ID NO: 5, also shown in FIGS. 1C-1E.

In another aspect, a method for treating Batten disease caused by a defect in the CLN2 gene comprises delivering to a subject in need thereof a vector (such as rAAV) which encodes TPP1, as described herein. In one embodiment, a method of treating a subject having Batten disease with a rAAV described herein is provided.

By "administering" as used in the methods means delivering the composition to the target selected cell which is characterized by a defect in the CLN2 gene. In one embodiment, the method involves delivering the composition by intrathecal injection. In another embodiment, ICV injection to the subject is employed. In another embodiment, intrathecal-lumbar (IT-L) injection to the subject is employed. In still another method, intravascular injections may be employed. In another embodiment, intramuscular injection is employed. Still other methods of administration may be selected by one of skill in the art given this disclosure.

By "administering" or "route of administration" is delivery of composition described herein, with or without a pharmaceutical carrier or excipient, of the subject. Routes of administration may be combined, if desired. In some embodiments, the administration is repeated periodically. The pharmaceutical compositions described herein are designed for delivery to subjects in need thereof by any suitable route or a combination of different routes. In some embodiments, direct delivery to the brain (optionally via intrathecal, ICV or IT-L injection), or delivery via systemic routes is employed, e.g., intravascular, intraarterial, intraocular, intravenous, intramuscular, subcutaneous, intradermal, and other parental routes of administration. The nucleic acid molecules, the expression cassette and/or vectors described herein may be delivered in a single composition or multiple compositions. Optionally, two or more different AAV may be delivered, or multiple viruses [see, e.g., WO20 2011/126808 and WO 2013/049493]. In another embodiment, multiple viruses may contain different replication-defective viruses (e.g., AAV and adenovirus), alone or in combination with proteins. As used herein, the terms "intrathecal delivery" or "intrathecal administration" refer to a route of administration for drugs via an injection into the spinal canal, more specifically into the subarachnoid space so that it reaches the cerebrospinal fluid (CSF). Intrathecal delivery may include lumbar puncture, intraventricular (including intracerebroventricular (ICV)), suboccipital/intracisternal, and/or C1-2 puncture. For example, material may be introduced for diffusion throughout the subarachnoid space by means of lumbar puncture. In another example, injection may be into the cisterna magna.

As used herein, the terms "intracisternal delivery" or "intracisternal administration" refer to a route of administration for drugs directly into the cerebrospinal fluid of the cisterna magna cerebellomedularis, more specifically via a suboccipital puncture or by direct injection into the cisterna magna or via permanently positioned tube. A device which is useful for delivering the compositions described herein into cerebrospinal fluid is described in PCT/US2017/16133, which is incorporated herein by reference.

Also provided herein are pharmaceutical compositions. The pharmaceutical compositions described herein are designed for delivery to subjects in need thereof by any suitable route or a combination of different routes.

In yet other aspects, these nucleic acid sequences, vectors, expression cassettes and rAAV viral vectors are useful in a pharmaceutical composition, which also comprises a pharmaceutically acceptable carrier, excipient, buffer, diluent, surfactant, preservative and/or adjuvant, etc. Such pharmaceutical compositions are used to express the optimized TPP1 in the host cells through delivery by such recombinantly engineered AAVs or artificial AAVs.

To prepare these pharmaceutical compositions containing the nucleic acid sequences, vectors, expression cassettes and rAAV viral vectors, the sequences or vectors or viral vector is preferably assessed for contamination by conventional methods and then formulated into a pharmaceutical composition suitable for administration to the patient. Such formulation involves the use of a pharmaceutically and/or physiologically acceptable vehicle or carrier, such as buffered saline or other buffers, e.g., HEPES, to maintain pH at appropriate physiological levels, and, optionally, other medicinal agents, pharmaceutical agents, stabilizing agents, buffers, carriers, adjuvants, diluents, surfactant, or excipient etc. For injection, the carrier will typically be a liquid. Exemplary physiologically acceptable carriers include sterile, pyrogen-free water and sterile, pyrogen-free, phosphate buffered saline. A variety of such known carriers are provided in U.S. Pat. No. 7,629,322, incorporated herein by reference. In one embodiment, the carrier is an isotonic sodium chloride solution. In another embodiment, the carrier is balanced salt solution. In one embodiment, the carrier includes tween. If the virus is to be stored long-term, it may be frozen in the presence of glycerol or Tween20.

In one exemplary specific embodiment, the composition of the carrier or excipient contains 180 mM NaCl, 10 mM NaPi, pH7.3 with 0.0001%-0.01% Pluronic F68 (PF68). The exact composition of the saline component of the buffer ranges from 160 mM to 180 mM NaCl. Optionally, a different pH buffer (potentially HEPES, sodium bicarbonate, TRIS) is used in place of the buffer specifically described. Still alternatively, a buffer containing 0.9% NaCl is useful.

As used herein, the term "dosage" can refer to the total dosage delivered to the subject in the course of treatment, or the amount delivered in a single unit (or multiple unit or split dosage) administration. The pharmaceutical virus compositions can be formulated in dosage units to contain an amount of replication-defective virus carrying the codon optimized nucleic acid sequences encoding TPP1 as described herein that is in the range of about $1.0 \times 10^9$ GC to about $1.0 \times 10^{16}$ GC per dose including all integers or fractional amounts within the range. In one embodiment, the compositions are formulated to contain at least $1 \times 10^9$, $2 \times 10^9$, $3 \times 10^9$, $4 \times 10^9$, $5 \times 10^9$, $6 \times 10^9$, $7 \times 10^9$, $8 \times 10^9$, or $9 \times 10^9$ GC per dose including all integers or fractional amounts within the range. In another embodiment, the compositions are formulated to contain at least $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, or $9 \times 10^{10}$ GC per dose including all integers or fractional amounts within the range. In another embodiment, the compositions are formulated to contain at least $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, or $9 \times 10^{11}$ GC per dose including all integers or fractional amounts within the range. In another embodiment, the compositions are formulated to contain at least $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, or $9 \times 10^{12}$ GC per dose including all integers or fractional amounts within the range. In another embodiment, the compositions are formulated to contain at least $1 \times 10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, or $9 \times 10^{13}$ GC per dose including all integers or fractional amounts within the range. In another embodiment, the compositions are formulated to contain at least $1 \times 10^{14}$, $2 \times 10^{14}$, $3 \times 10^{14}$, $4 \times 10^{14}$, $5 \times 10^{14}$, $6 \times 10^{14}$, $7 \times 10^{14}$, $8 \times 10^{14}$, or $9 \times 10^{14}$ GC per dose including all integers or fractional amounts within the range. In another embodiment, the compositions are formulated to contain at least $1 \times 10^{15}$, $2 \times 10^{15}$, $3 \times 10^{15}$, $4 \times 10^{15}$, $5 \times 10^{15}$, $6 \times 10^{15}$, $7 \times 10^{15}$, $8 \times 10^{15}$, or $9 \times 10^{15}$ GC per dose including all integers or fractional amounts within the range. In one embodiment, for human application the dose can range from $1 \times 10^{10}$ to about $1 \times 10^{12}$ GC per dose including all integers or fractional amounts within the range. All dosages may be measured by any known method, including as measured by oqPCR or digital droplet PCR (ddPCR) as described in, e.g., M. Lock et al, Hum Gene Ther Methods. 2014 April; 25(2):115-25. doi: 10.1089/hgtb.2013.131, which is incorporated herein by reference.

In one embodiment, an aqueous suspension suitable for administration to a Batten patient is provided. The suspension comprises an aqueous suspending liquid and about $7.5 \times 10^9$ GC or viral particles to about $1 \times 10^{12}$ GC or viral particles per gram of brain of a recombinant adeno-associated virus (rAAV) described herein useful as a therapeutic for Batten disease.

It may also be desirable to administer multiple "booster" dosages of the pharmaceutical compositions of this invention. For example, depending upon the duration of the transgene within the CNS, one may deliver booster dosages at 6 month intervals, or yearly following the first administration. The fact that AAV-neutralizing antibodies were not generated by administration of the rAAV vector should allow additional booster administrations.

Such booster dosages and the need therefor can be monitored by the attending physicians, using, for example, the TPP1 activity, and neurocognitive tests described in the examples below. Other similar tests may be used to determine the status of the treated subject over time. Selection of the appropriate tests may be made by the attending physician. Still alternatively, the method of this invention may also involve injection of a larger volume of virus-containing solution in a single or multiple infection to allow TPP1 activity levels close to those found in normal subjects.

These above doses may be administered in a variety of volumes of carrier, excipient or buffer formulation, ranging from about 100 microliters to about 50 mL, including all numbers within the range, depending on the size of the patient, the viral titer used, the route of administration, and the desired effect of the method. In one embodiment, the volume of carrier, excipient or buffer is at least about 500 µL. In one embodiment, the volume is about 750 µL. In another embodiment, the volume is about 1 mL. In another embodiment, the volume is about 2 mL. In another embodiment, the volume is about 3 mL. In another embodiment, the volume is about 4 mL. In another embodiment, the volume is about 5 mL. In another embodiment, the volume is about 6 mL. In another embodiment, the volume is about 7 mL. In another embodiment, the volume is about 8 mL. In another embodiment, the volume is about 9 mL. In another embodiment, the volume is about 10 mL. In another embodiment, the volume is about 11 mL. In another embodiment, the volume is about 12 mL. In another embodiment, the volume is about 13 mL. In another embodiment, the volume is about 14 mL. In another embodiment, the volume is about 15 mL. In another embodiment, the volume is about 16 mL. In another embodiment, the volume is about 17 mL. In another embodiment, the volume is about 18 mL. In another embodiment, the volume is about 19 mL. In another embodiment, the volume is about 20 mL. In another embodiment, the volume is about 21 mL. In another embodiment, the volume is about 22 mL. In another embodiment, the volume is about 23 mL. In another embodiment, the volume is about 24 mL. In another embodiment, the volume is about 25 mL or more. In one embodiment, the maximum injected volume is about 10% of total cerebrospinal fluid volume.

In one embodiment, the viral constructs may be delivered in doses of from at least $1 \times 10^9$ to about least $1 \times 10^{13}$ GCs in volumes of about 100 microliters mL to about 1 mL for small animal subjects, such as mice. For larger veterinary subjects, the larger human dosages and volumes stated above are useful. See, e.g., Diehl et al, J. Applied Toxicology, 21:15-23 (2001) for a discussion of good practices for administration of substances to various veterinary animals. This document is incorporated herein by reference.

It is desirable that the lowest effective concentration of virus or other delivery vehicle be utilized in order to reduce the risk of undesirable effects, such as toxicity. Still other dosages in these ranges may be selected by the attending physician, taking into account the physical state of the subject, preferably human, being treated, the age of the subject, and the degree to which the disorder, has developed.

Yet another aspect described herein is a method for treating, retarding or halting progression of Batten disease in a mammalian subject. In one embodiment, an rAAV carrying the CLN2 native, modified or codon optimized sequence, preferably suspended in a physiologically compatible carrier, diluent, excipient and/or adjuvant, may be administered to a desired subject including a human subject in a therapeutically effective amount. This method comprises administering to a subject in need thereof any of the nucleic acid sequences, expression cassettes, rAAV genomes, plasmids, vectors or rAAV vectors or compositions containing them. In one embodiment, the composition is delivered intrathecally. In another embodiment, the composition is delivered via ICV. In still another embodiment, the composition is delivered using a combination of administrative routes suitable for treatment of Batten disease, and may also involve intravenous administration or other conventional administration routes.

For use in these methods, the volume and viral titer of each dosage is determined individually, as further described herein. The dosages, administrations and regimens may be determined by the attending physician given the teachings of this specification. In another embodiment, the method involves administering the compositions in two or more dosages (e.g., split dosages). In another embodiment, a second administration of an rAAV including the selected expression cassette (e.g., CLN2 containing cassette) is performed at a later time point. Such time point may be weeks, months or years following the first administration. Such second administration is, in one embodiment, performed with an rAAV having a different capsid than the rAAV from the first administration. In another embodiment, the rAAV from the first and second administration have the same capsid.

In still other embodiments, the compositions described herein may be delivered in a single composition or multiple compositions. Optionally, two or more different AAV may be delivered, or multiple viruses (see, e.g., WO 2011/126808 and WO 2013/049493). In another embodiment, multiple viruses may contain different replication-defective viruses (e.g., AAV and adenovirus).

According to the present invention, a "therapeutically effective amount" of the hTPP1 is delivered as described herein to achieve a desired result, i.e., treatment of Batten disease or one or more symptoms thereof. A Unified Batten Disease Rating Scale (UBDRS) has been proposed which is a comprehensive system which physical, seizure, behavioral, and capability assessments. See, Mink, J., The Unified Batten Disease Rating Scale, accessible at rarediseases.info.nih.govifilesimink.pdf. In one embodiment, the goal of treatment is to limit progression of the disease. This may be assessed by a quantitative and qualitative evaluation of symptoms, using the CLN2 disease rating disease scale or UBDRS.

In another embodiment, the method includes performing additional testing, e.g., assays and neurocognitive testing to determine the efficacy of the treatment. Such tests include those performed as part of the UBDRS, discussed above, and include, without limitation, assessment of: speech clarity, tongue protrusion, visual acuity, tone (arms, legs, neck), strength (arms, legs), hand tapping, heel stomping, spontaneous movements (akinesia), Stereotypies, Dystonia, myoclonus, tremor, chorea, dysmetria, gait, postural stability, seizures, behavior and mood, and overall health.

In one embodiment of the methods described herein, a one-time delivery of a composition as described herein, e.g., an AAV delivery of an optimized CLN2 cassette, is useful in treating Batten disease in a subject. In another embodiment of the methods described herein, a one-time delivery of a composition as described herein, e.g., an AAV delivery of an optimized CLN2 cassette, is useful in preventing Batten disease in a subject having a CLN2 defect.

Thus, in one embodiment, the composition is administered before disease onset. In another embodiment, the composition is administered prior to the initiation of neurological impairment. In another embodiment, the composition is administered after initiation of neurological impairment. In one embodiment, neonatal treatment is defined as being administered a TPP1 coding sequence, expression cassette or vector as described herein within 8 hours, the first 12 hours, the first 24 hours, or the first 48 hours of delivery. In another embodiment, particularly for a primate (human or non-human), neonatal delivery is within the period of about 12 hours to about 1 week, 2 weeks, 3 weeks, or about 1 month, or after about 24 hours to about 48 hours. In another embodiment, the composition is delivered after onset of symptoms. In one embodiment, treatment of the patient (e.g., a first injection) is initiated prior to the first year of life. In another embodiment, treatment is initiated after the first 1 year, or after the first 2 to 3 years of age, after 5 years of age, after 11 years of age, or at an older age. In one embodiment, treatment is initiated from ages about 4 years of age to about 12 years of age. In one embodiment, treatment is initiated on or after about 4 years of age. In one embodiment, treatment is initiated on or after about 5 years of age. In one embodiment, treatment is initiated on or after about 6 years of age. In one embodiment, treatment is initiated on or after about 7 years of age. In one embodiment, treatment is initiated on or after about 8 years of age. In one embodiment, treatment is initiated on or after about 9 years of age. In one embodiment, treatment is initiated on or after about 10 years of age. In one embodiment, treatment is initiated on or after about 11 years of age. In one embodiment, treatment is initiated on or after about 12 years of age. However, treatment can be initiated on or after about 15, about 20, about 25, about 30, about 35, or about 40 years of age. In one embodiment, treatment in utero is defined as administering the composition as described herein in the fetus. See, e.g., David et al, Recombinant adeno-associated virus-mediated in utero gene transfer gives therapeutic transgene expression in the sheep, Hum Gene Ther. 2011 April; 22(4):419-26. doi: 10.1089/hum.2010.007. Epub 2011 Feb. 2, which is incorporated herein by reference.

In another embodiment, the composition is readministered at a later date. Optionally, more than one readministration is permitted. Such readministration may be with the same type of vector, a different viral vector, or via non-viral delivery as described herein.

The goals of the treatments described herein include limiting or halting the progression of Batten disease. Desirable results of the treatments include, without limitation, increases in any of the assessment scores of the UBDRS, an increase in TPP1 activity or expression levels, increase in (or reduction in progression of impairment of) motor function, as determined by neurocognitive testing, and increase in (or reduction in progression of impairment of) cortical volume by MRI. A desired result includes reducing muscle weakness, increasing muscle strength and tone, or maintaining or increasing respiratory health, or reducing tremors or twitching. Other desired endpoints can be determined by a physician.

In yet another embodiment, any of the above described methods is performed in combination with another, or secondary, therapy. The secondary therapy may be any now known, or as yet unknown, therapy which helps prevent, arrest or ameliorate these mutations or defects or any of the effects associated therewith. The secondary therapy can be administered before, concurrent with, or after administration of the compositions described above. In one embodiment, a secondary therapy involves non-specific approaches for maintaining the health of the retinal cells, such as administration of neurotrophic factors, anti-oxidants, anti-apoptotic agents. The non-specific approaches are achieved through injection of proteins, recombinant DNA, recombinant viral vectors, stem cells, fetal tissue, or genetically modified cells. The latter could include genetically modified cells that are encapsulated. In one embodiment, the secondary therapy is intracerebroventricular cerliponase alpha (BMN 190). See, Schulz et al, Intracerebroventricular cerliponase alfa (BMN 190) in children with CLN 2 disease: results from a phase 1/2 open label, dose-escalation study, J Inherit Metab Disease, 39:S51, which is incorporated herein by reference. The recommended dosage is 30-300 mg ICV infusion administered every other week.

In one embodiment, a method of generating a recombinant rAAV comprises obtaining a plasmid containing an AAV expression cassette as described above and culturing a packaging cell carrying the plasmid in the presence of sufficient viral sequences to permit packaging of the AAV viral genome into an infectious AAV envelope or capsid. Specific methods of rAAV vector generation are described above and may be employed in generating a rAAV vector that can deliver the codon optimized CLN2 in the expression cassettes and genomes described above and in the examples below.

In certain embodiments of this invention, a subject has Batten disease, for which the components, compositions and methods of this invention are designed to treat. As used herein, the term "subject" as used herein means a mammalian animal, including a human, a veterinary or farm animal, a domestic animal or pet, and animals normally used for clinical research. In one embodiment, the subject of these methods and compositions is a human. Still other suitable subjects include, without limitation, murine, rat, canine, feline, porcine, bovine, ovine, non-human primate and others. As used herein, the term "subject" is used interchangeably with "patient".

As used herein, the term "treatment" or "treating" is defined encompassing administering to a subject one or more compounds or compositions described herein for the purposes of amelioration of one or more symptoms of Batten disease. "Treatment" can thus include one or more of reducing onset or progression of Batten disease, preventing disease, reducing the severity of the disease symptoms, or retarding their progression, including the progression of neurological impairment, removing the disease symptoms, delaying onset of disease or monitoring progression of disease or efficacy of therapy in a given subject.

In one aspect, a coding sequence is provided which encodes a functional TPP1 protein. By "functional hTPP1", is meant a gene which encodes an TPP1 protein which provides at least about 50%, at least about 75%, at least about 80%, at least about 90%, or about the same, or greater than 100% of the biological activity level of the native TPP1 protein, or a natural variant or polymorph thereof which is not associated with disease.

A variety of assays exist for measuring TPP1 expression and activity levels in vitro. See, e.g., Example 2 below. The methods described herein can also be combined with any other therapy for treatment of Batten disease or the symptoms thereof. The management of CLN2 disease is complex. Patients require extensive multidisciplinary medical care due to the high symptom load and the rapid rate of functional decline, and families require extensive psychosocial support, yet no management guidelines currently exist for this condition. See, e.g., Williams et al, Management strategies for CLN2 disease, Pediatric Neurology 69 (2017) 102e112, which is incorporated herein by reference. However, in certain embodiments, the standard of care may include intracerebroventricular cerliponase alpha (BMN 190). See, Schulz et al, Intracerebroventricular cerliponase alfa (BMN 190) in children with CLN 2 disease: results from a phase 1/2 open label, dose-escalation study, J Inherit Metab Disease, 39:S51, which is incorporated herein by reference. The recommended dosage is 30-300 mg ICV infusion administered every other week.

In certain embodiments, the AAV9.CLN2 vector is produced. A number of suitable purification methods may be selected. Examples of suitable purification methods are described, e.g., International Patent Application No. PCT/US2016/065970, filed Dec. 9, 2016 and its priority documents, U.S. Patent Application No. 62/322,071, filed Apr. 13, 2016 and 62/226,357, filed Dec. 11, 2015 and entitled "Scalable Purification Method for AAV9", which is incorporated by reference herein.

In the case of AAV viral vectors, quantification of the genome copies ("GC") may be used as the measure of the dose contained in the formulation. Any method known in the art can be used to determine the genome copy (GC) number of the replication-defective virus compositions of the invention. One method for performing AAV GC number titration is as follows: Purified AAV vector samples are first treated with DNase to eliminate contaminating host DNA from the production process. The DNase resistant particles are then subjected to heat treatment to release the genome from the capsid. The released genomes are then quantitated by real-time PCR using primer/probe sets targeting specific region of the viral genome (for example poly A signal). Another suitable method for determining genome copies are the quantitative-PCR (qPCR), particularly the optimized qPCR or digital droplet PCR [Lock Martin, et al, Human Gene Therapy Methods. April 2014, 25(2): 115-125. doi:10.1089/hgtb.2013.131, published online ahead of editing Dec. 13, 2013]. Alternatively, ViroCyt3100 can be used for particle quantitation, or flow cytometry. In another method, the effective dose of a recombinant adeno-associated virus carrying a nucleic acid sequence encoding the optimized TPP1 coding sequence is measured as described in S. K. McLaughlin et al, 1988 J. Virol., 62:1963, which is incorporated by reference in its entirety.

The replication-defective virus compositions can be formulated in dosage units to contain an amount of replication-defective virus that is in the range of about $1.0 \times 10^9$ GC to about $9 \times 10^{15}$ GC (to treat an average subject of 70 kg in body weight) including all integers or fractional amounts within the range, and preferably $1.0 \times 10^{12}$ GC to $1.0 \times 10^{14}$ GC for a human patient. In one embodiment, the compositions are formulated to contain at least $1 \times 10^9$, $2 \times 10^9$, $3 \times 10^9$, $4 \times 10^9$, $5 \times 10^9$, $6 \times 10^9$, $7 \times 10^9$, $8 \times 10^9$, or $9 \times 10^9$ GC per dose including all integers or fractional amounts within the range. In another embodiment, the compositions are formulated to contain at least $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, or $9 \times 10^{10}$ GC per dose including all integers or fractional amounts within the range. In another embodiment, the compositions are formulated to contain at least $1 \times 10^{11}$, $2 \times 10^{11}$, $3 \times 10^{11}$, $4 \times 10^{11}$, $5 \times 10^{11}$, $6 \times 10^{11}$, $7 \times 10^{11}$, $8 \times 10^{11}$, or $9 \times 10^{11}$ GC per dose including all integers or fractional amounts within the range. In another embodiment, the compositions are formulated to contain at least $1 \times 10^{12}$, $2 \times 10^{12}$, $3 \times 10^{12}$, $4 \times 10^{12}$, $5 \times 10^{12}$, $6 \times 10^{12}$, $7 \times 10^{12}$, $8 \times 10^{12}$, or $9 \times 10^{12}$ GC per dose including all integers or fractional amounts within the range. In another embodiment, the compositions are formulated to contain at least $1 \times 10^{13}$, $2 \times 10^{13}$, $3 \times 10^{13}$, $4 \times 10^{13}$, $5 \times 10^{13}$, $6 \times 10^{13}$, $7 \times 10^{13}$, $8 \times 10^{13}$, or $9 \times 10^{13}$ GC per dose including all integers or fractional amounts within the range. In another embodiment, the compositions are formulated to contain at least $1 \times 10^{14}$, $2 \times 10^{14}$, $3 \times 10^{14}$, $4 \times 10^{14}$, $5 \times 10^{14}$, $6 \times 10^{14}$, $7 \times 10^{14}$, $8 \times 10^{14}$, or $9 \times 10^{14}$ GC per dose including all integers or fractional amounts within the range. In another embodiment, the compositions are formulated to contain at least $1 \times 10^{15}$, $2 \times 10^{15}$, $3 \times 10^{15}$, $4 \times 10^{15}$, $5 \times 10^{15}$, $6 \times 10^{15}$, $7 \times 10^{15}$, $8 \times 10^{15}$, or $9 \times 10^{15}$ GC per dose including all integers or fractional amounts within the range. In one embodiment, for human application the dose can range from $1 \times 10^{10}$ to about $1 \times 10^{15}$ GC per dose including all integers or fractional amounts within the range.

In certain embodiments, the dose may be in the range of about $1 \times 10^9$ GC/g brain mass to about $1 \times 10^{12}$ GC/g brain mass. In certain embodiments, the dose may be in the range of about $3 \times 10^{10}$ GC/g brain mass to about $3 \times 10^{11}$ GC/g brain mass. In certain embodiments, the dose may be in the range of about $5 \times 10^{10}$ GC/g brain mass to about $1.85 \times 10^{11}$ GC/g brain mass.

In one embodiment, the viral constructs may be delivered in doses of from at least about least $1 \times 10^9$ GCs to about $1 \times 10^{15}$, or about $1 \times 10^{11}$ to $5 \times 10^{13}$ GC. Suitable volumes for delivery of these doses and concentrations may be determined by one of skill in the art. For example, volumes of about 1 µL to 150 mL may be selected, with the higher volumes being selected for adults. Typically, for newborn infants a suitable volume is about 0.5 mL to about 10 mL, for older infants, about 0.5 mL to about 15 mL may be selected. For toddlers, a volume of about 0.5 mL to about 20 mL may be selected. For children, volumes of up to about 30 mL may be selected. For pre-teens and teens, volumes up to about 50 mL may be selected. In still other embodiments, a patient may receive an intrathecal administration in a volume of about 5 mL to about 15 mL are selected, or about 7.5 mL to about 10 mL. Other suitable volumes and dosages may be determined. The dosage will be adjusted to balance the therapeutic benefit against any side effects and such dosages may vary depending upon the therapeutic application for which the recombinant vector is employed.

The above-described recombinant vectors may be delivered to host cells according to published methods. In certain embodiments, for administration to a human patient, the rAAV is suitably suspended in an aqueous solution containing saline, a surfactant, and a physiologically compatible salt or mixture of salts. Suitably, the formulation is adjusted to a physiologically acceptable pH, e.g., in the range of pH 6 to 9, or pH 6.5 to 7.5, pH 7.0 to 7.7, or pH 7.2 to 7.8. As the pH of the cerebrospinal fluid is about 7.28 to about 7.32, for intrathecal delivery, a pH within this range may be desired; whereas for intravenous delivery, a pH of 6.8 to about 7.2 may be desired. However, other pHs within the broadest ranges and these subranges may be selected for other route of delivery.

A suitable surfactant, or combination of surfactants, may be selected from among nonionic surfactants that are nontoxic. In one embodiment, a difunctional block copolymer surfactant terminating in primary hydroxyl groups is selected, e.g., such as Pluronic® F68 (BASF), also known as Poloxamer 188, which has a neutral pH, has an average molecular weight of 8400. Other surfactants and other Poloxamers may be selected, i.e., nonionic triblock copolymers composed of a central hydrophobic chain of polyoxypropylene (poly(propylene oxide)) flanked by two hydrophilic chains of polyoxyethylene (poly(ethylene oxide)), SOLUTOL HS 15 (Macrogol-15 Hydroxystearate), LABRASOL (Polyoxy capryllic glyceride), polyoxy 10 oleyl ether, TWEEN (polyoxyethylene sorbitan fatty acid esters), ethanol and polyethylene glycol. In one embodiment, the formulation contains a poloxamer. These copolymers are commonly named with the letter "P" (for poloxamer) followed by three digits: the first two digits×100 give the approximate molecular mass of the polyoxypropylene core, and the last digit×10 gives the percentage polyoxyethylene content. In one embodiment Poloxamer 188 is selected. The surfactant may be present in an amount up to about 0.0005% to about 0.001% of the suspension.

In one example, the formulation may contain, e.g., buffered saline solution comprising one or more of sodium chloride, sodium bicarbonate, dextrose, magnesium sulfate (e.g., magnesium sulfate·7H2O), potassium chloride, calcium chloride (e.g., calcium chloride·2H2O), dibasic sodium phosphate, and mixtures thereof, in water. Suitably, for intrathecal delivery, the osmolarity is within a range compatible with cerebrospinal fluid (e.g., about 275 to about 290); see, e.g., emedicine.medscape.com/article/2093316-overview. Optionally, for intrathecal delivery, a commercially available diluent may be used as a suspending agent, or in combination with another suspending agent and other optional excipients. See, e.g., Elliotts B® solution (Lukare Medical). In other embodiments, the formulation may contain one or more permeation enhancers. Examples of suitable permeation enhancers may include, e.g., mannitol, sodium glycocholate, sodium taurocholate, sodium deoxycholate, sodium salicylate, sodium caprylate, sodium caprate, sodium lauryl sulfate, polyoxyethylene-9-laurel ether, or EDTA.

In another embodiment, the composition includes a carrier, diluent, excipient and/or adjuvant. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The buffer/carrier should include a component that prevents the rAAV, from sticking to the infusion tubing but does not interfere with the rAAV binding activity in vivo.

Optionally, the compositions of the invention may contain, in addition to the rAAV and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The compositions according to the present invention may comprise a pharmaceutically acceptable carrier, such as defined above. Suitably, the compositions described herein comprise an effective amount of one or more AAV suspended in a pharmaceutically suitable carrier and/or admixed with suitable excipients designed for delivery to the subject via injection, osmotic pump, intrathecal catheter, or for delivery by another device or route. In one example, the composition is formulated for intrathecal delivery. In one embodiment, intrathecal delivery encompasses an injection into the spinal canal, e.g., the subarachnoid space. In one embodiment, the route of delivery is intracerebroventricular injection (ICV). In another embodiment, the route of delivery is intrathecal-lumbar (IT-L) delivery.

The viral vectors described herein may be used in preparing a medicament for delivering hTPP1 to a subject (e.g., a human patient) in need thereof, supplying functional TPP1 to a subject, and/or for treating Batten disease. A course of treatment may optionally involve repeat administration of the same viral vector (e.g., an AAV9 vector) or a different viral vector (e.g., an AAV9 and an AAVrh10). Still other combinations may be selected using the viral vectors and non-viral delivery systems described herein.

The hTPP1 cDNA sequences described herein can be generated in vitro and synthetically, using techniques well known in the art. For example, the PCR-based accurate synthesis (PAS) of long DNA sequence method may be utilized, as described by Xiong et al, PCR-based accurate synthesis of long DNA sequences, Nature Protocols 1, 791-797 (2006). A method combining the dual asymmetrical PCR and overlap extension PCR methods is described by Young and Dong, Two-step total gene synthesis method, Nucleic Acids Res. 2004; 32(7): e59. See also, Gordeeva et al, J Microbiol Methods. Improved PCR-based gene synthesis method and its application to the *Citrobacter freundii* phytase gene codon modification. 2010 May; 81(2):147-52. Epub 2010 Mar. 10; see, also, the following patents on oligonucleotide synthesis and gene synthesis, Gene Seq. 2012 April; 6(1):10-21; U.S. Pat. Nos. 8,008,005; and 7,985, 565. Each of these documents is incorporated herein by reference. In addition, kits and protocols for generating DNA via PCR are available commercially. These include the use of polymerases including, without limitation, Taq polymerase; OneTaq® (New England Biolabs); Q5® High-Fidelity DNA Polymerase (New England Biolabs); and GoTaq® G2 Polymerase (Promega). DNA may also be generated from cells transfected with plasmids containing the hOTC sequences described herein. Kits and protocols are known and commercially available and include, without limitation, QIAGEN plasmid kits; Chargeswitch® Pro Filter Plasmid Kits (Invitrogen); and GenElute™ Plasmid Kits (Sigma Aldrich). Other techniques useful herein include sequence-specific isothermal amplification methods that eliminate the need for thermocycling. Instead of heat, these methods typically employ a strand-displacing DNA polymerase, like Bst DNA Polymerase, Large Fragment (New England Biolabs), to separate duplex DNA. DNA may also be generated from RNA molecules through amplification via the use of Reverse Transcriptases (RT), which are RNA-dependent DNA Polymerases. RTs polymerize a strand of DNA that is complimentary to the original RNA template and is referred to as cDNA. This cDNA can then be further amplified through PCR or isothermal methods as outlined above. Custom DNA can also be generated commercially from companies including, without limitation, GenScript; GENEWIZ®; GeneArt® (Life Technologies); and Integrated DNA Technologies.

The term "expression" is used herein in its broadest meaning and comprises the production of RNA or of RNA and protein. With respect to RNA, the term "expression" or "translation" relates in particular to the production of peptides or proteins. Expression may be transient or may be stable.

The term "translation" in the context of the present invention relates to a process at the ribosome, wherein an mRNA strand controls the assembly of an amino acid sequence to generate a protein or a peptide.

It is to be noted that the term "a" or "an" refers to one or more. As such, the terms "a" (or "an"), "one or more," and "at least one" are used interchangeably herein.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

As used herein, "disease", "disorder" and "condition" are used interchangeably, to indicate an abnormal state in a subject.

As used herein, the term "about" or "—" means a variability of 10% from the reference given, unless otherwise specified.

The term "regulation" or variations thereof as used herein refers to the ability of a composition to inhibit one or more components of a biological pathway.

Unless defined otherwise in this specification, technical and scientific terms used herein have the same meaning as commonly understood by one of ordinary skill in the art and by reference to published texts, which provide one skilled in the art with a general guide to many of the terms used in the present application.

EXAMPLES

The following examples are illustrative only and are not intended to limit the present invention.

Example 1: AAV.hTPP1co Vectors

Figure 1B:
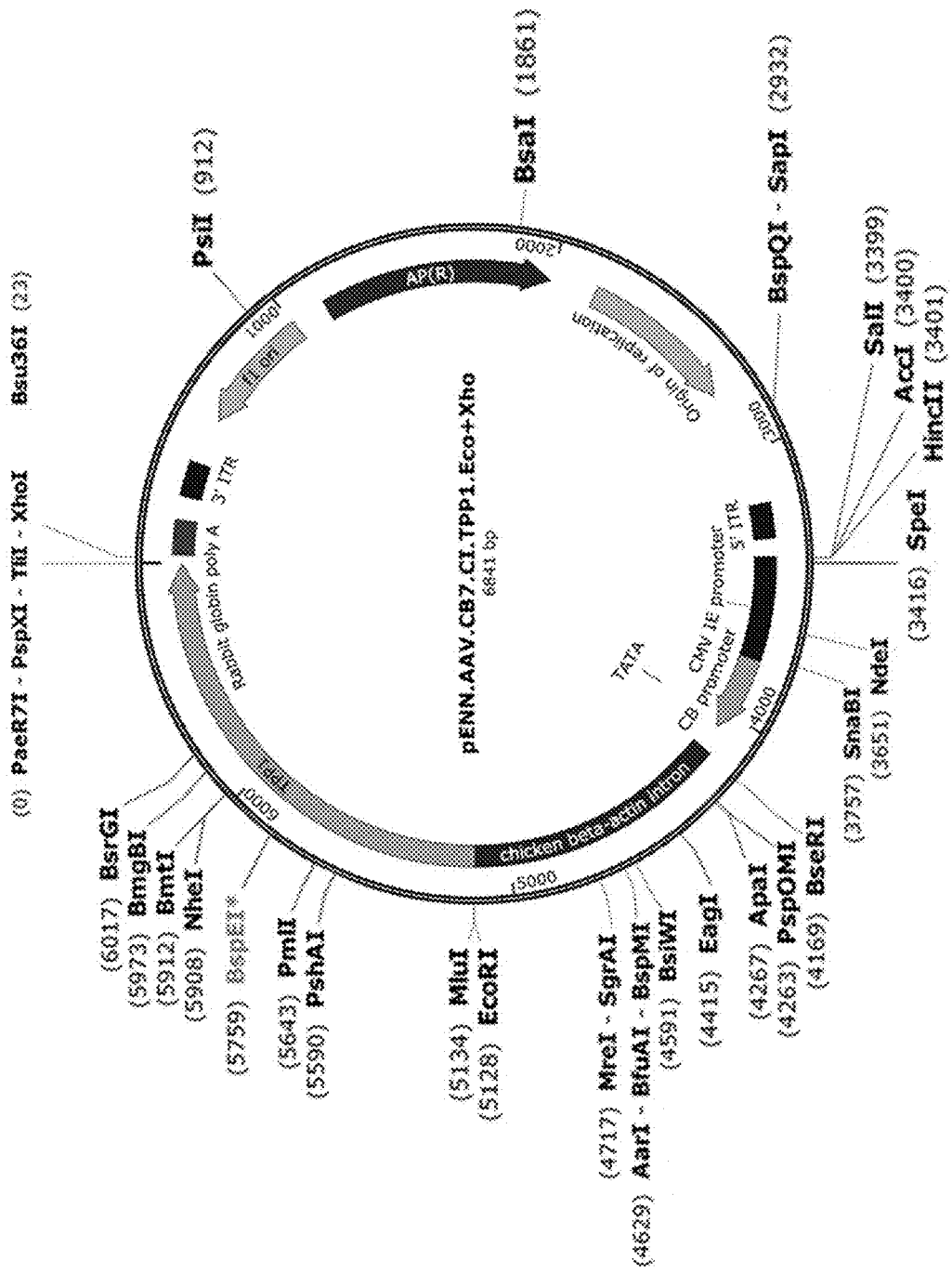
FIG. 1B provides a map of the production plasmid of the AAV.hTPP1co vector.

The human (h) TPP1-encoding optimized cDNA was custom-designed for optimal codon usage and synthesized. The hTPP1co cDNA as shown in FIG. 1F and reproduced as SEQ ID NO: 3, was then placed in a transgene expression cassette which was driven by a CB7 promoter, a hybrid between a cytomegalovirus (CMV) immediate early enhancer (C4) and the chicken beta actin promoter, while transcription from this promoter is enhanced by the presence of the chicken beta actin intron (CI) (FIGS. 1A and 1B). The polyA signal for the expression cassette is the rabbit beta-globin (RBG) polyA.

A 6841 bp production plasmid of AAV.hTPP1co vector (AAV.CB7.CI.hTPP1co.RBG) was constructed with the hTPP1co expression cassette described herein flanked by AAV2 derived ITRs as well as resistance to Ampicillin as a selective marker (FIG. 1B). A similar AAV.hTPP1co production plasmid with resistance to Kanamycin was also constructed. The vectors derived from both plasmids were single-stranded DNA genome with AAV2 derived ITRs flanking the hTPP1co expression cassette described herein.

The AAV.hTPP1co vectors were made by triple transfection and formulated in excipient consisting of phosphate-buffered saline (PBS) containing and 0.001% Pluronic F68 (PF68). See, e.g. Mizukami, Hiroaki, et al., A Protocol for AAV vector production and purification, Diss. Di-vision of Genetic Therapeutics, Center for Molecular Medicine, 1998. Genome titers of the vector produced was determined via droplet digital PCR (ddPCR). See, e.g., M. Lock et al, Hu Gene Therapy Methods, Hum Gene Ther Methods. 2014 April; 25(2):115-25. doi: Epub 2014 Feb. 14.

Example 2: In Vitro Expression of AAV.hTPP1co Vectors

The AAV.hTPP1co was tested for expression of functional TPP1 in vitro. HEK 293 cells were plated in 6-well plates. When reaching about 90% confluency, the cells were transfected with 5 μg of AAV.hTPP1co vectors or no DNA. 72 hours later, the supernatant of the cell cultures was harvested and processed for TPP1 activity/enzyme assay.

For the TPP1 assay, fluorogenic substrate, AAF-AMC (Bachem, Catolog #1-1415, 10 mM dissolved in DMSO) was diluted in Assay Buffer containing 50 mM sodium acetate and 100 mM sodium chloride at pH 5.0) to 500 μM. 50 μL of the tested sample (supernatant) was firstly loaded into a black well plate in duplicate. 50 μL of 500 μM substrate was added to each well to start the reaction of converting substrates to products catalyzed by functional TPP1 and releasing fluorescent product, AMC. The intensities of fluorescent signal from samples were monitored for 10 minutes via a fluorescent microplate reader in kinetic mode (the emission wavelength was set at 460 nm while the excitation wavelength was at 380 nm). 7-Amino-4-Methyl-coumarin (AMC, Thermo Fisher #A191) was utilized as a fluorescence reference standard. Concentrations of the released fluorescent product were calculated based on the standard curve of AMC diluted in the Assay Buffer and then plotted in FIG. 2.

Figure 2:
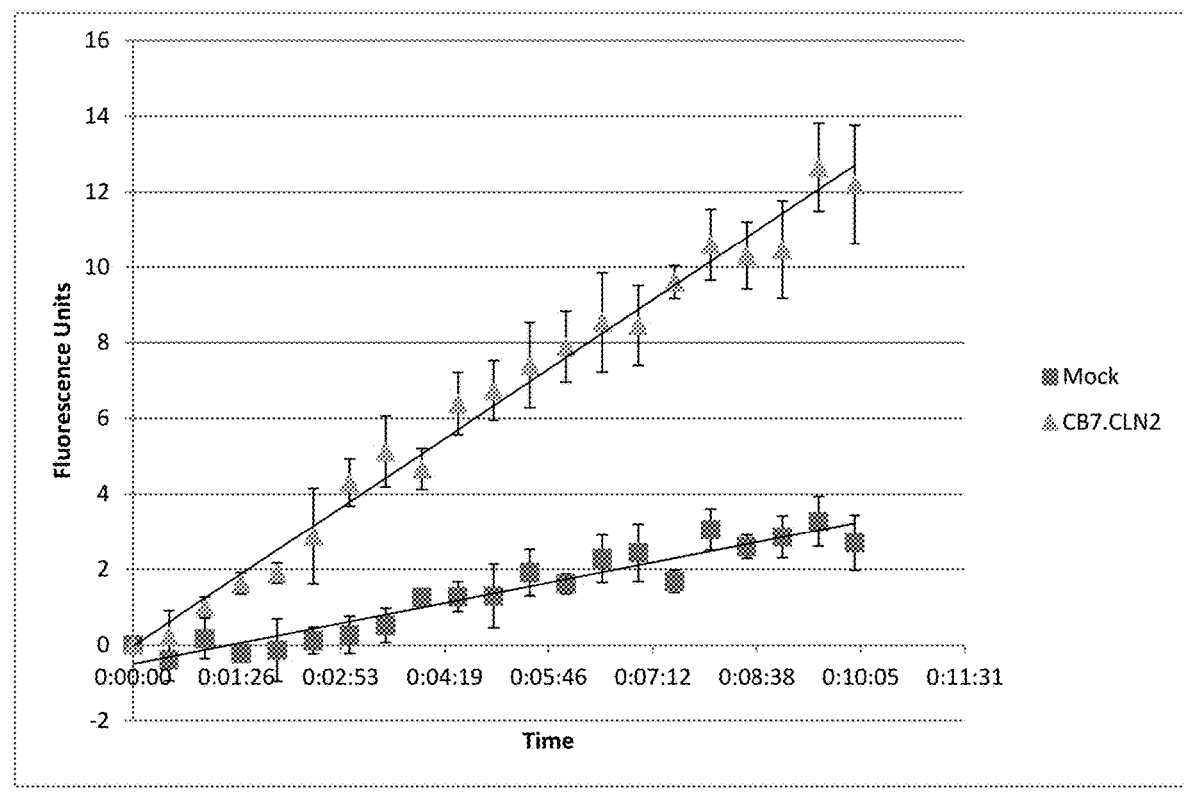
FIG. 2 is a line graph of TPP1 enzyme activity measured in the culture supernatant of AAV.hTPP1co transfected cells (triangles) and control cells (squares) as described in Example 2.

During the 10-minute observation period, supernatant from cell cultures transfected with AAV.hTPP1co demonstrated a steady and sharp increase of the fluorescent signal (CB7.CLN2, upper line in FIG. 2) while the supernatant from the non-transfected cells only showed a minor increase (Mock, lower line in FIG. 2). This result indicated that the AAV.hTPP1co vectors were able to express human functional TPP1 proteins in vitro.

Example 3: In Vivo Expression of AAV.hTPP1co Vectors

To assess the in vivo expression of the AAV.hTPP1co vectors described herein, 10 C57BL/6J wild-type male mice were injected with the AAV.hTPP1co described herein via intracerebroventricular administration at $1\times10^{11}$ GC. Mice were kept on a 12-hour light/12-hour dark cycle, and food/water was provided ad libitum. 10 wild-type male mice without injection served as control. All mice were sacrificed and necropsy was performed 14 days after injection. Expression of TPP1 and overt toxicity were evaluated.

Figure 3A:
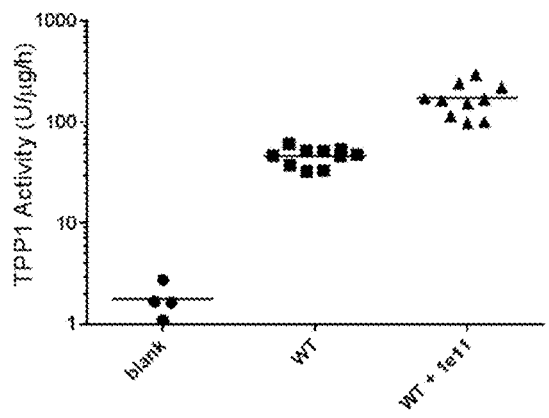
FIGS. 3A to 3D provide TPP1 enzyme activity measured in brain (FIG. 3A), CSF (FIG. 3B), serum (FIG. 3C) and liver (FIG. 3D) of wild type mice with no treatment or with an ICV administration of AAV.hTPP1co at $11 \times 10^{11}$ GC as described in Example 3.

To assess expression of TPP1 in the murine brain, brain samples of the mice described above were harvested and homogenized in MPS® tissue lysis buffer. Protein concentration in brain lysate was determined by the bicinchoninic acid assay (BCA assay). TPP1 enzyme activity of the brain lysate was measured as described in Example 2 and normalized to units/h/µg brain protein. Assay buffer incubated with substrates and no brain lysate was served as negative control. The results were plotted in FIG. 3A. Brain lysate of wildtype mice without injection (WT, FIG. 3A) demonstrated a TPP1 enzyme activity compared to the negative control (blank, FIG. 3A), while the highest level of TPP1 enzyme activity was observed in the mice treated with AAV.hTPP1co (WT+1e11, FIG. 3A).

Figure 3B:
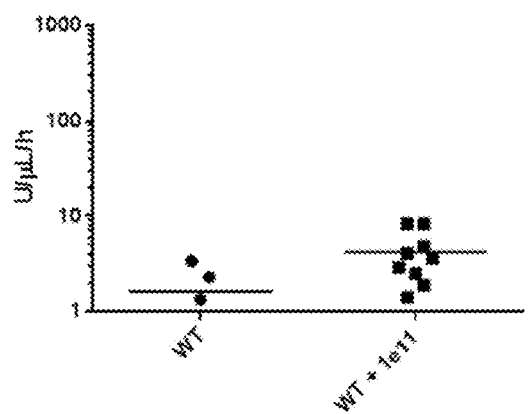
Figure 3C:
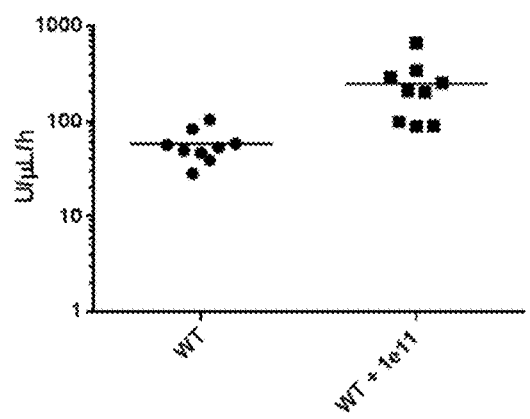
Figure 3D:
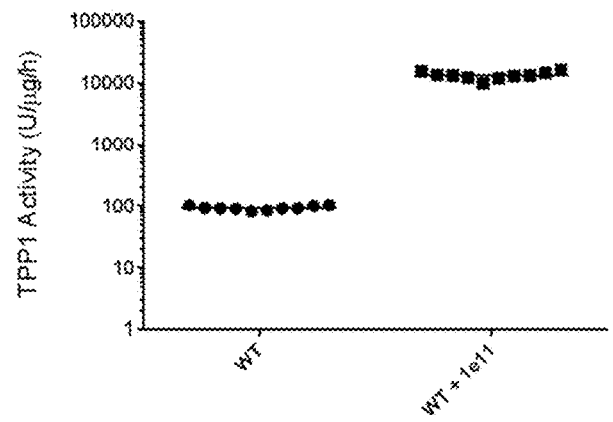

Parallel studies of TPP1 enzyme activity using cerebrospinal fluid (CSF, FIG. 3B), serum (FIG. 3C) and liver (FIG. 3D) of the tested animals described above were performed. CSF samples contaminated with blood during collection were excluded from measurement. The result for liver samples was normalized to units/h/µg liver protein determined by BCA assay while those for CSF and serum samples were normalized to units/h/µl of liquid volume of the tested sample used for the assay. Increases in TPP1 enzyme activity of mice injected with the AAV.hTPP1co were observed in CSF (WT+1e11, FIG. 3B), serum (WT+1e11, FIG. 3C) and liver (WT+1e11, FIG. 3D) compared to mice without treatment (WT).

In view of the above, injection of the AAV.hTPP1co described herein resulted in expression of functional human TPP1 in vivo.

Tissues and organs of the tested mice, such as brain, eye, liver, lung, kidney and muscle, were also collected and are processed for toxicity evaluation, such as morphology and immunostaining of damage response marker (GFAP and etc.).

Example 4: AAV.hTPP1co Vectors in TPP1 Knock-Out (KO) Mice/Mouse Model

To assess the efficacy of the AAV.hTPP1co injection, TPP1 knock-out (KO) mice were obtained and maintained on a 12-hour light/12-hour dark cycle with food/water provided ad libitum. 2-3 month old female TPP1 KO mice (KO mice) were utilized. 5 mice were injected with $1\times10^{11}$ GC of the AAV.hTPP1co vectors via intracerebroventricular administration while 4 mice were injected with phosphate-buffered saline (PBS) as control. Body weights of the tested mice were monitored and recorded. TPP1 enzyme activity of samples from brain, CSF, serum and liver were measured. Brain histology, such as lipofuscin auto-fluorescence and astrocytosis assessed by GFAP expression, was evaluated. Functional and behavioral tests, such as rotarod, tremor scoring and nest building were performed.

While the Tpp1m1j mouse model of CLN2 disease has not been extensively described in the scientific literature, available data from Karst et al. (2016) and a natural history study establish that the Tpp1m1j mouse model is a biologically-relevant animal model of CLN2 disease that reproduces many of the characteristic features of the target patient population. The Tpp1m1j mouse model results from a single nucleotide mutation in the splice donor site downstream of exon 8 of the CLN2 gene, which encodes for the soluble lysosomal enzyme TPP1. As a result of this mutation, Tpp1m1j mice exhibit undetectable levels of TPP1 enzymatic activity in brain tissue, as well as a similar pathophysiology, phenotype, and mortality as humans with CLN2 disease. Inflammation and glial cell activation in CNS tissues appears to begin as early as 1-month of age in this mouse model, while the accumulation of lipofuscin is detectable in neurons by 2-months of age. Subsequently, animals exhibit progressive neuronal degeneration in the brain, spinal cord, and motor neurons. Tpp1m1j mice initially show intermittent tremor and hunched posture starting at 2-months of age, before progressing to a constant tremor, diminished neurobehavioral function, and weight loss over time. Seizures and death are observed as early as 3.5-months of age, and 100% mortality is observed by 6-months of age (Karst et al., 2016; unpublished data). In summary, the Tpp1m1J mouse model is a biologically-relevant animal model of CLN2 disease and is highly similar to other established mouse and canine models, including the Tpp1tm1Plob mouse (Sleat et al., 2004) and TPP1-null dachshund (Awano et al., 2006) models.

There are several reported animal models of CLN2 disease, including canine and murine models. The most well-characterized in the scientific literature is the TPP1-null canine model first reported in a population of Dachshunds (Awano et al., 2006). As a result of a single nucleotide deletion in exon 4 of canine TPP1 (canine ortholog of human CLN2) and predicted frameshift mutation with a premature stop codon, affected canines exhibit many of the clinical and biochemical manifestations of humans with CLN2 disease, including deficient TPP1 enzymatic activity (<1% WT levels in brain tissue), generalized myoclonic seizures (responsive to diazepam), retinal degeneration and vision loss, progressive neurological signs (vomiting, tremors, unresponsiveness to learned commands, proprioceptive ataxia, asymmetric reduction in menace response, cerebellar ataxia, motor dysfunction, hyperactivity, myoclonus of the head, decreased cognitive function), and early mortality (~10-12 months of age). Extensive neuropathology consistent with CLN2 disease in humans is also evident, including neuronal cell loss, depletion of white matter, progressive brain atrophy, and lysosomal accumulation of autoflourescent storage granules consisting of characteristic curvilinear-appearing material. However, breeding constraints and the extremely limited availability of this animal pose challenges to the use of the TPP1-null canine model in the preclinical testing program for AAV9.CB7.hCLN2.

The most commonly-reported murine model of CLN2 disease in the scientific literature is the Tpp1tm1Plob mouse model developed by Dr. Peter Lobel (Sleat et al., 2004). In this model, the CLN2 gene carries a neomycin cassette in Intron 11. As a result, there is no detectable TPP1 enzymatic activity in the brain of these animals. Pathophysiology and neurobehavioral changes in this model reflect CLN2 disease in humans, including progressive neurological signs (impaired motor function, tremor, seizure), extensive neuropathology (progressive lysosomal accumulation and inflammation in the brain, widespread axonal degeneration), and shortened lifespan (~6 months). The Tpp1tm1Plob mouse model has been incorporated into the preclinical testing programs of numerous clinical stage programs (ClinicalTrials.gov identifiers: NCT00151216, NCT01414985, NCT01161576; Passini et al., 2005; Passini et al., 2006; Sondhi et al., 2007; Sondhi et al., 2008). However, the Tpp1tm1Plob mouse model is not commercially-available and thus was not feasible to incorporate into the preclinical testing program for AAV9.CB7.hCLN2.

The Tpp1m1j mouse model of CLN2 disease, which is highly similar to the Tpp1tm1Plob mouse model, is commercially-available through Jackson Laboratories. This mouse model results from a single nucleotide mutation in the splice donor site downstream of exon 8 of the CLN2 gene. As a result of this mutation, Tpp1m1j mice exhibit undetectable levels of TPP1 enzymatic activity in brain tissue, as well as a similar pathophysiology, phenotype, and mortality as humans with CLN2 disease (Karst et al., 2016).

Figure 15:
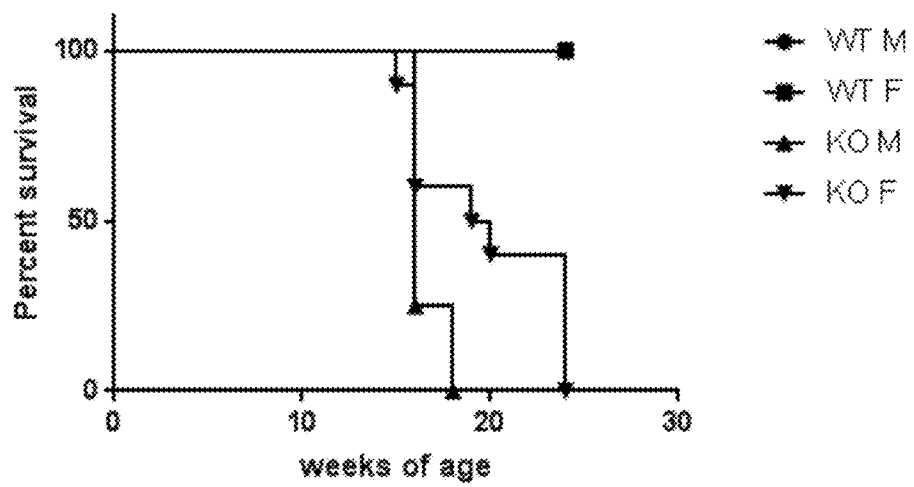
FIG. 15 shows survival curves of Tpp1m1j mice (denoted as '1(0'; n=60) and wild type littermate controls (n=40). Median survival was observed to be 16 and 19 weeks for males and females, respectively. Early death in males was attributed to cage fighting-induced seizures.

A natural history study was conducted to further characterize the Tpp1m1j mouse model. Briefly, wild-type (n=40) and Tpp1m1j mice (n=60) were monitored for progression of the disease phenotype (body weight, clinical observations, survival) with scheduled sacrifices (of surviving animals, as feasible) at 1-(n=20), 3-(n=20), and 5.5-(n=20) months of age to evaluate TPP1 enzymatic activity and histopathology (accumulation of lysosomal storage material, astrocytosis) in brain tissue. Briefly, cage-side observations revealed onset of a moderate gait abnormality and/or tremors in the majority of Tpp1m1j mice at 2-months of age, while a minority of animals appeared to experience generalized fatal seizures prior to the onset of other clinical symptoms. A slight impairment of motor coordination was observed in Tpp1m1j mice at 3-months of age upon clinical observations. Grand mal seizures or generalized clonic-tonic seizures were observed in the majority of animals, beginning as early 3.5-months of age. The seizures appeared to be caused and/or amplified by environmental stress, such as during cage changes, loud noises, and fighting (of note, reported instances of apparent fatal startle seizures induced by environmental stimuli such as loud noises have also been reported in the Tpp1tm1Plob mouse model (Sleat et al., 2004)). In general, Tpp1m1j mice showed rapid deterioration following onset of symptoms, including decreased motility, gradual weight loss, inability to feed, partial and then generalized tremor, seizures, and early mortality (100% mortality by 6-months of age; FIG. 15). The apparent gender-specific differences in the survival curves are hypothesized to be the result of a higher incidence of environmental stimuli-induced fatal seizures in male animals due to fighting.

Figure 16A:
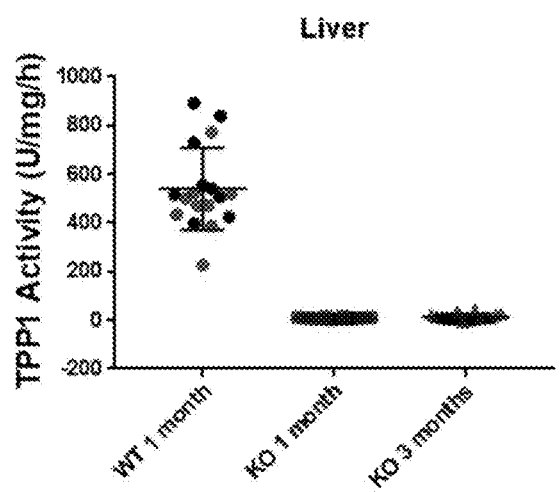
FIGS. 16A to 16B show TPP1 enzymatic activity in Tpp1m1j (KO) and wild-type littermates (WT) at 1 and 3 months of age (Liver, FIG. 16A; and Cerebrum, FIG. 16B). Data for female animals is denoted in blue; data for male animals is denoted in black.
Figure 16B:
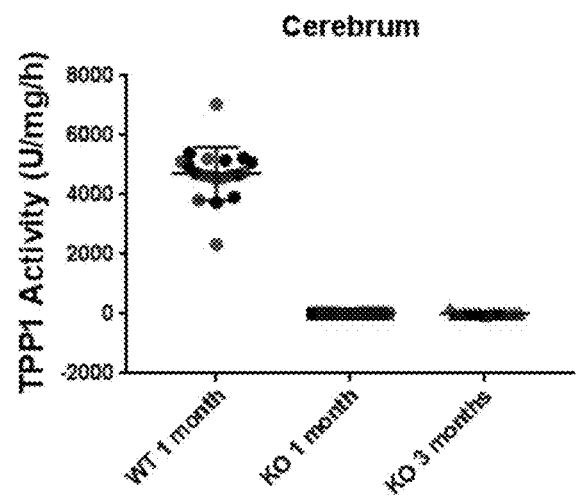

TPP1 enzymatic activity was measured in the brain and liver of Tpp1m1j mice using a modified version of the protocol by Sohar et al. (Sohar et al., 2000). Data confirm the absence of any residual TPP1 activity in all tested tissues at all time points (FIG. 16).

Cortex, hippocampus, brainstem, and cerebellum were harvested at 1-, 3-, and 5.5-months of age and processed to analyze neuropathology and accumulation of lysosomal storage material as a marker for disease progression. CNS tissue showed progressive lysosomal accumulation and neuropathology, which was marked by end-stage disease at 5.5-months (data not shown). Briefly, on H&E stained sections, brain was unremarkable at 1-month of age (whereas mild astrocytosis was already present upon GFAP immunostaining). At 3-months of age, numerous measures of neuropathology were observed including eosinophilic storage material in large brainstem neurons, gliosis in the cortex, and widespread astrocytosis in multiple regions of the brain. At 5.5-months of age, storage pathology was prominent in pyramidal cortical neurons and brainstem large neurons, in addition to widespread and prominent astrocytosis throughout the brain. Storage material was readily apparent under fluorescent light (without staining), particularly in the brainstem.

Besides intrinsic neuronal defects, another emerging factor common to many LSDs (including CLN2 disease) is neuroinflammation, which may negatively impact neuronal survival and contribute to progressive neurodegeneration. Microglial and astrocyte activation is a hallmark of many LSDs that affect the CNS, which often precedes and predicts regions where eventual neuron loss will occur (Bosch et al., 2015). Thus, to enable the objective quantification of astrocytosis, a scoring system was developed based on GFAP staining (ie, GFAP score). The GFAP score was defined as the average number of activated astrocytes (stained with anti-GFAP antibody) per 20× power field. In this natural history study, GFAP scores were calculated in the hippocampus and in the cortex at 1-, 3-, and 5.5-months of age. Results show a progressive accumulation of GFAP that coincides with disease progression (FIG. 17). Astrocytosis appears to be a more sensitive marker of neuropathology than neuronal storage accumulation as it was observed before storage accumulation (which was detected at 3-months of age). The observation of astrocytosis as early as 1-month of age in the cortex and hippocampus is consistent with the hypothetical role of inflammation as a primary cause of neuronal death in CLN2 disease, although the sensitivity of methods used to detect lipofuscin accumulation (non-specific dyes with no signal amplification by immunohistochemistry) is decreased relative to GFAP staining. In summary, the Tpp1m1J mouse model is a biologically-relevant animal model of CLN2 disease and highly similar to other established mouse and canine models, including the Tpp1tm1Plob mouse (Sleat et al., 2004) and TPP1-null dachshund (Awano et al., 2006) animal models. Tpp1m1j mice exhibit characteristic features of CLN2 disease in humans, including early age at onset of clinical symptoms, rapid progression of the abnormal phenotype, and shortened lifespan, as well as similar pathophysiological, biochemical, and functional changes. Starting in the first weeks of life (and presumably before birth) in the Tpp1m1j mouse, the deficiency in TPP1 enzymatic activity culminates in the accumulation of lipid-containing residues of lysosomal digestion, also known as lipofuscin granules, in the cytoplasm of neurons. Lipofuscin accumulation in the cytoplasm of neurons is revealed by H&E staining and correlates with an increase in astrocyte activation or astrocytosis (indicative of neuro-inflammation). Subsequently, Tpp1m1j mice experience progressive deterioration of motor function and gait abnormalities, tremors, seizures, weight loss and inability to eat, and early mortality.

A. Weights

Figure 11:
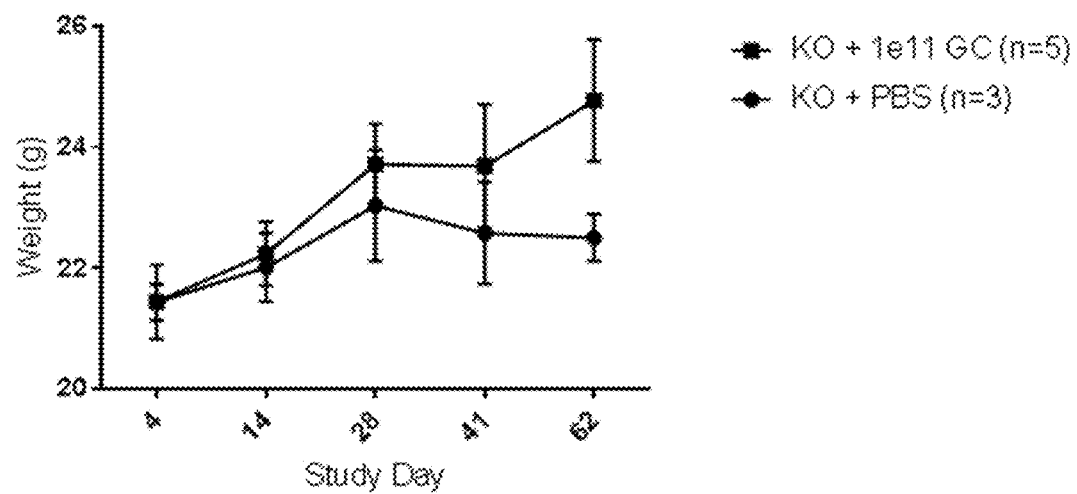
FIG. 11 provides body weights of KO mice injected with PBS (KO+PBS, n=3) or $1 \times 10^{11}$ GC of the AAV.hTPP1co (KO+1e11 GC, n=5) as described in Example 4.

Body weights of five TPP1 KO mice injected with $1 \times 10^{11}$ GC of AAV.hTPP1co vectors were monitored about every 14 days after injection (closed squares connected by line shown in FIG. 11). Three TPP1 KO mice injected with PBS only served as control (closed circles connected by line in FIG. 11). The fourth TPP1 KO mice died during the study thus was excluded here. The body weights at day 4 after injection were comparable between the treated mice and control while treatment with $1 \times 10^{11}$ GC of AAV9.CB7.CI.hCLN2co.RBG appeared to booster weight gain in KO females.

B. TPP1 Enzyme Activity

TPP1 enzyme activities in the serum of TPP1 KO females injected ICV with PBS (FIG. KO+PBS, n=4) or $1 \times 10^{11}$ GC AAV9.CB7.CI.hCLN2co.RBG (FIG. 10, KO+1e11, n=5) were measured. Wildtype male mice without injection (FIG. 10, WT, n=2) or injected ICV with $1 \times 10^{11}$ GC AAV9.CB7.CI.hCLN2co.RBG (FIG. 10, WT+1e11, n=2) as described in Example 3 were tested simultaneously for accurate comparison.

Figure 10:
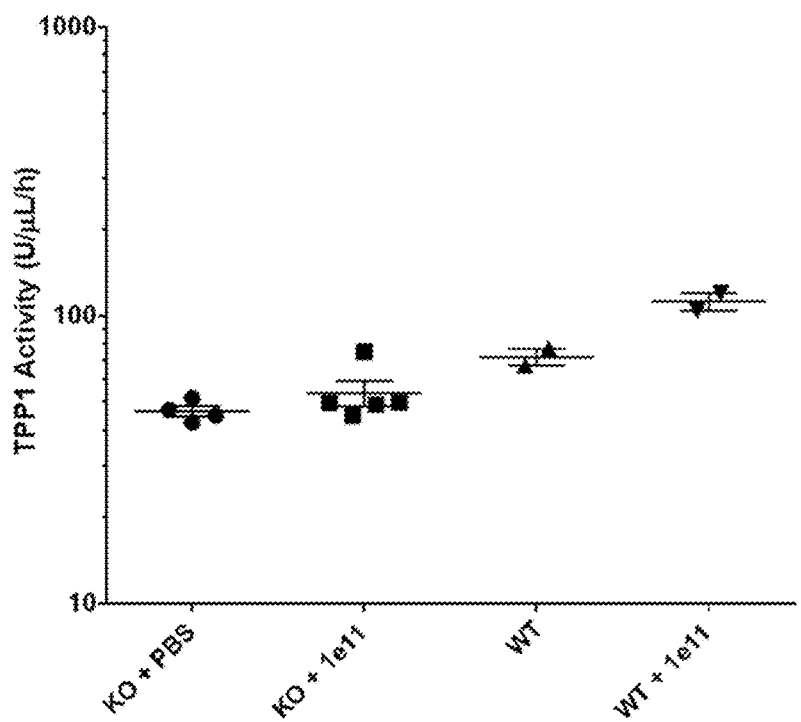
FIG. 10 provides results of TPP1 enzyme activity tested in the sera of TPP1 KO and wildtype mice treated with PBS only or $1 \times 10^{11}$ GC of the AAV.hTPP1co as described in Example 4.

TPP1 enzyme activity was measured in serum and normalized to Units/µL/h by dividing by the volume of serum used for the assay as described in Example 2. After injection with AAV.hTPP1co, female KO mice did not show elevated TPP1 enzyme activity in serum in contrast to the male wildtype mice (FIG. 10).

C. Brain Histology days post ICV injection with PBS or $1\times10^{11}$ GC AAV9.CB7.CI.hCLN2co.RBG, animals were euthanized and tissues, such as brain, lung, liver, muscle and kidney, were harvested. The brain samples were sectioned and taken for further histological analysis.

Cortex and thalamus were stained for GFAP (Glial fibrillary acidic protein), a marker of astrocyte activation, by immunohistochemistry. Astrocyte activation, also known as astryocytosis, is one of the primary causes of neuron death/loss in NCLs. WT animals showed relatively little GFAP staining in cortex and thalamus (not shown). PBS treated knockouts showed dramatically increased GFAP staining in cortex and thalamus (not shown). Knockouts treated with $1\times10^{11}$ GC AAV9.CB7.CI.hCLN2co.RBG appeared to show amelioration of GFAP staining in both cortex and thalamus (not shown).

D. Functional and Behavioral Tests a. Nest Building

TPP1 KO females injected ICV with PBS (n=4) or $1\times10^{11}$ GC of AAV9.CB7.CI.hCLN2co.RBG (n=5) were group housed. Animals were rehoused into new cages and 24 hours post cage-change, nestlets were observed for signs of nest-building.

KO females treated with PBS showed minimal signs of tearing up their nestlets and building a nest, which is consistent with observations described by Ron Crystal in the Peter Lobel model. KO females treated with $1\times10^{11}$ GC of AAV9.CB7.CI.hCLN2co.RBG tore up their nestlets and built a normal nest, demonstrating an improvement in normal behavior of the mice. Nest building test is performing on more mice for quantitative purpose.

b. Rocking Rotarod Test

TPP1 KO females injected ICV with PBS (n=4) or $1\times10^{11}$ GC of AAV9.CB7.CI.hCLN2co.RBG (n=5) underwent rocking rotarod testing according to the protocol below.

For the rotarod test, mice were exposed to the rotarod for 4 consecutive days, one habituation and rocking rotarod session and then three subsequent training sessions (including motor learning and rocking rotarod). An increase in the latency to "fail" indicates learning had occurred. The time period of the day for training and testing was kept the same, which were 8 am to 12 pm. On the first day, two trials were performed at a constant low speed (5 rpm) to allow the mouse to habituation to the equipment. Mice were placed on a rotarod running at 5 rpm for 120 seconds. If a mouse fell, the animal was put back on the rod. 2 minutes rest was allowed between the 2 trials. The Rotarod was set in constant speed mode at 5 rpm. On the same day, rocking rotarod session was started just after habituation (2 minutes rest in between was allowed). The rotarod was set at 10 rpm with reverse rotation every other rotation for a total of 180 seconds. A trial was terminated when a mouse fell off or after 180 seconds. After a 3 min of inter-trial intervals (ITI), a second trial was performed. After another 3 min ITI, a third and last trial was performed. Rotarod setting was set in rocking mode at 10 rpm with reverse rotation after one full rotation.

Figure 12A:
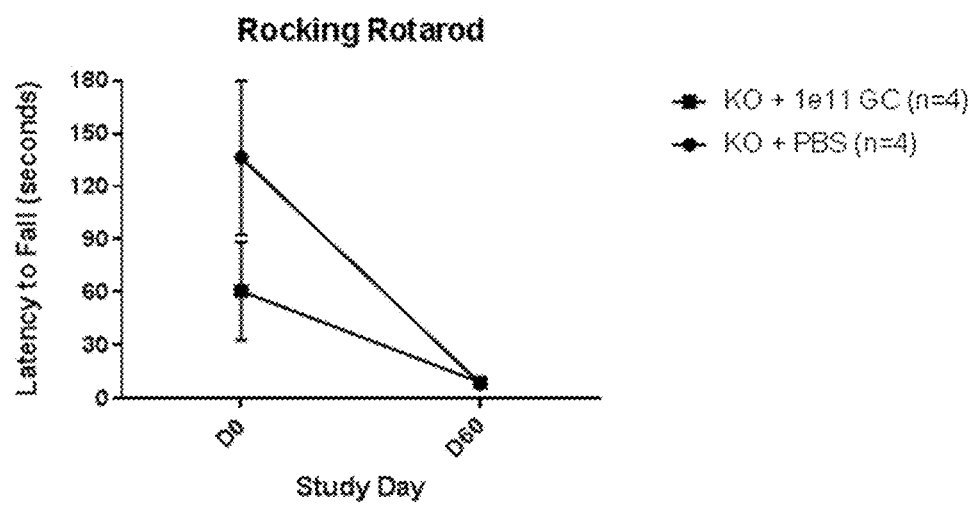
FIG. 12A provides results of the rocking rotarod assay tested in the TPP1 KO mice treated with PBS only (KO+PBS, n=4) or $1 \times 10^{11}$ GC of the AAV.hTPP1co (KO+1e11GC, n=4) as described in Example 4. The latency to fall was measured as the time spent on the rod in second.

3 months old animal were tested starting on the injection day (D0) as well as on day 60 post-injection (about 5 months old, D60). Each mouse was tested 3 times on D0 and 3 times on D60. The average of latency to fall measured as time spent on the rotarod in second for each group was plotted in FIG. 12A. No significant difference between PBS (KO+PBS, closed circles connected by line in FIG. 12A, n=4) and AAV.hTPP1co treated KOs (KO+1e11 GC, closed squares connected by line in FIG. 12A, n=4) was observed on D60.

c. Accelerating Rotarod Test

TPP1 KO females injected ICV with PBS (n=4) or $1\times10^{11}$ GC of AAV9.CB7.CI.hCLN2co.RBG (n=5) underwent accelerating rotarod testing according to the protocol below.

Mice were exposed to the Rotarod for 4 consecutive days, one habituation and rocking rotarod session and then three subsequent training sessions (including motor learning and accelerated rotarod). An increase in the latency to "fail" indicated learning had occurred. The time period of the day for training and testing was kept the same, which were 8 am to 12 pm. On the first day, two trials were performed at a constant low speed (5 rpm) to allow the mouse to habituation to the equipment. Mice were then placed on a Rotarod running at 5 rpm for 120 seconds. If a mouse fell, the animal was put back on the rod. 2 minutes rest was allowed between the 2 trials. The rotarod was set in constant speed mode at 5 rpm. On the second to the fourth day, mice were exposed to accelerated rotarod. The Rotarod was set to accelerate from 5 rpm to 40 rpm over 300 seconds. A trial was terminated when a mouse fell off, made one passive complete revolution while hanging on, or after 300 seconds. After a 5 min ITI, a second trial was performed. After another 5 min ITI, a third and last trial was performed. During this session, the rotarod was set in accelerated ramp mode from 5 to 40 rpm for 300 second.

Figure 12B:
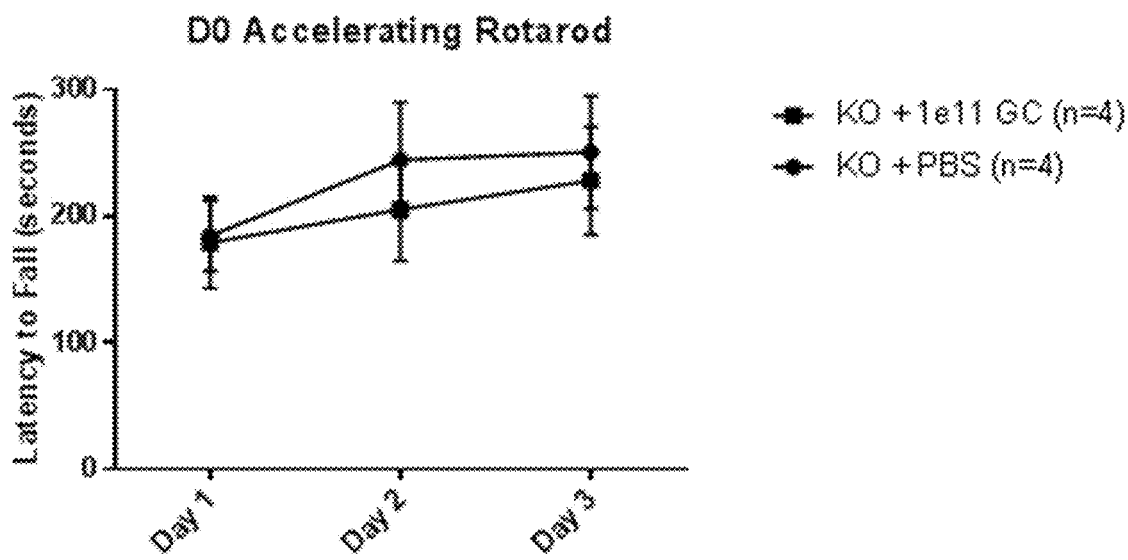
FIGS. 12B and 12C provides results of the accelerating rotarod assay tested in TPP1 KO mice treated with PBS only (KO+PBS, n=4) or $1 \times 10^{11}$ GC of the AAV.hTPP1co (KO+1e11GC, n=4) in the test starting on the day of injection (D0) or the test starting 60 days post injection (D60) as described in Example 4. The latency to fall was measured as the time spent on the rod in second.
Figure 12C:
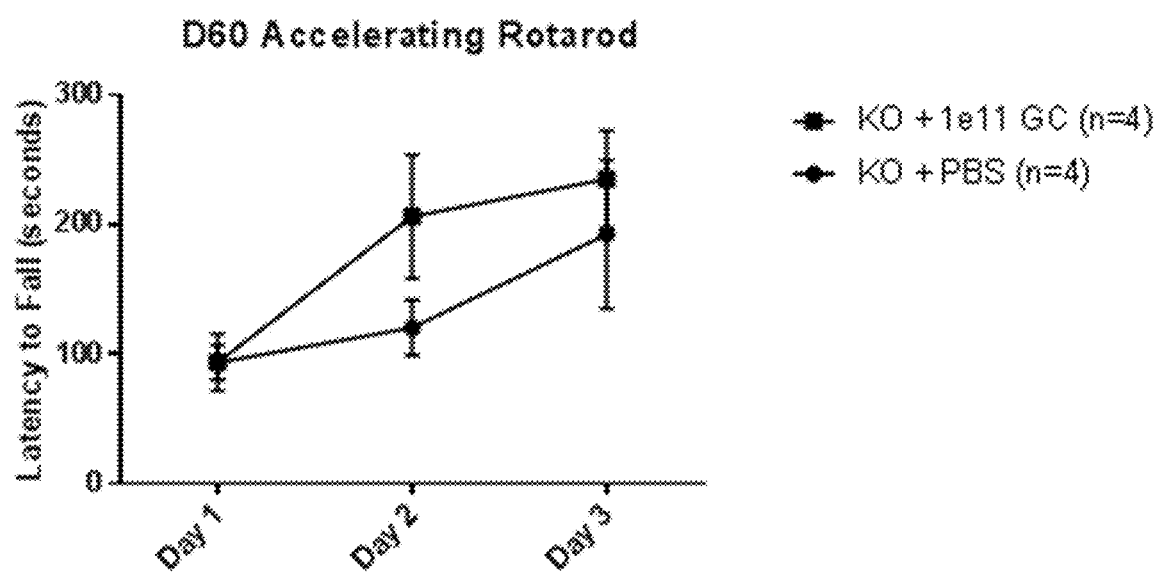

3 months old animal were tested starting on the injection day (D0) as well as on day 60 post-injection (about 5 months old, D60). Each mouse was tested 3 times on D0 and 3 times on D60. The average of latency to fall measured as time spent on the rotarod in second for each group was plotted in FIGS. 12B (D0) and 12C (D60). An improved learning was observed on the second training date in AAV.hTPP1co treated KOs during the D60 test.

Example 5: Dose Efficacy

Experiments were performed to assess the efficacy and toxicity of the AAV.hTPP1co injection at various doses. TPP1 knock-out (KO) mice and wildtype mice were maintained on a 12-hour light/12-hour dark cycle with food/water provided ad libitum. TPP1 KO mice at 1 month of age were injected with $3\times10^9$ (low dose) or $3\times10^{11}$ (high dose) GC of the AAV.hTPP1co described above via intracerebroventricular administration. TPP1 KO and Wildtype mice were also injected with PBS and served as control. Each group contained ten male and ten female animals. Survival and body weights of the tested mice were monitored and recorded. TPP1 enzyme activity of samples from brain, CSF, serum and liver were measured. Brain histology, such as lipofuscin auto-fluorescence and astrocytosis assessed by GFAP expression, was evaluated. Functional and behavioral tests, such as motor coordination assay, were performed. Furthermore, the anti-TPP1 immune response was also evaluated.

A. Survival Curve and Body Weight

Survival was monitored daily and animal was euthanized if they lost 20% of weight. The survival curve was plotted in FIG. 4A while the median survival weeks for each tested group were calculated and listed in FIG. 4B. Death of high dose treated animals was not detected during the observation period with an exception of one female. All low dose treated animals and untreated KO were found dead. The median survival weeks of male KO mice were 15 while female KO mice demonstrated a 24-week median survival time. In the $3\times10^9$ GC of AAV.hTPP1co treated KO mice, the median survival of males was 16 weeks while the one of females was 19 weeks (FIG. 4B).

Figure 4A:
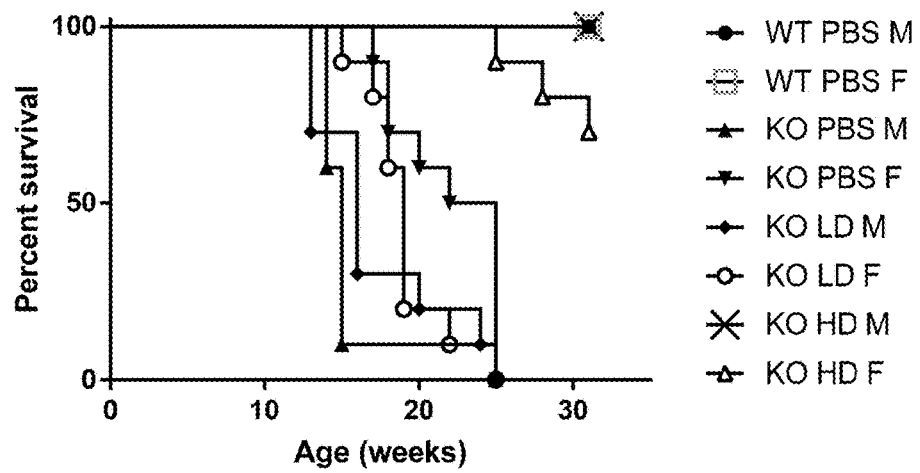
FIG. 4A is a survival cure of TPP1 KO mice treated with PBS only (male, closed upright triangles; female, closed inverted triangles), $3 \times 10^9$ GC (male, diamonds; female, open circles) or $3 \times 10^{11}$ GC (male, cross; female, open triangles) of the AAV.hTPP1co vectors. Wildtype mice (male, closed circles; female, open squares) were served as control. In each group, both male and female animals were monitored and recorded separately to reveal potential gender differences.

Animals administered AAV9.CB7.hCLN2 at the high-dose exhibited normalization of motor learning (cerebellum function) compared to wild-type controls, as well as dramatically increased survival (85% survival at 30 weeks post-injection versus 0% survival in control animals) (FIG. 4A'). There did not appear to be benefit in survival or other measures of bioactivity in Tpp1m1j mice that were administered AAV9.CB7.hCLN2 at the low-dose (7.5×109 GC/g brain mass), with an observed median survival of ~17 weeks in both low-dose and control animals.

Figure 5:
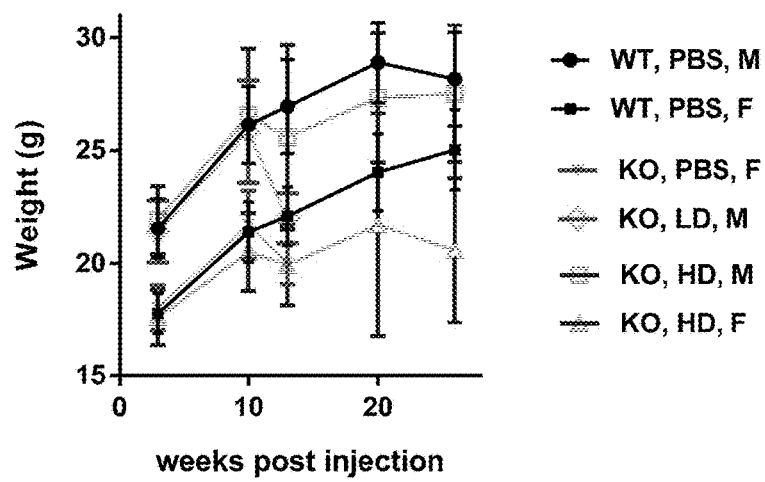
FIG. 5 is a line graph showing the body weights in gram of TPP1 KO mice treated with PBS only (female, closed triangles), $3 \times 10^9$ GC (male, open diamonds) or $3 \times 10^{11}$ GC (male, open squares; female, open triangles) of the AAV.hTPP1co. Wildtype mice (male, closed circles; female, closed squares) were served as controls.

The body weights of all tested animals described above were plotted in FIG. 5. High dose treated animals showed a moderate weight loss compare to KO.

B. Motor Coordination Assay

NCL is a CNS disease and neurons death affects the motricity. To evaluate the disease phenotype, mice were tested for motor coordination on a rotarod as described in Example 4. Mice were trained on this protocol every 3 weeks since age of one month. The latency to fall measured in time spent on rotarod in second were recorded. The results of trial 3 at day 3 of the test starting day post therapy were plotted in FIG. 6. Significant differences between untreated and high dose treated KO were observed, while a same physical ability between the WT and high dose treated KO were observed. These results demonstrated that the high dose therapy compensated the disease phenotype in TPP1 KO mice.

C. Anti-TPP1 Immune Response

To evaluate toxicity and enzyme correction of the AAV.hTPP1co described above, the immune response against TPP1 was evaluated. At 70 days post ICV injection, 3.3 month old mice described above in the instant Example were bleed. The produced sera were tested for presence of anti-TPP1 antibody to evaluate the immune response against TPP1 protein.

Immune response was measured by ELISA as described below. TPP1 proteins at pH7.5 were diluted in regular PBS for a final concentration at 2.5 µg/ml. To coat the ELISA plate, 50 µL of diluted TPP1 was loaded to each well and the covered plate was kept in cold room overnight. Five wash via buffer B were performed on the following day in a plate washer. 200 µl blocking solution (2% (2 g per 100 ml) bovine serum albumin (BSA) diluted in PBS) was added to each well and incubated for a minimum of 1 hour at room temperature to block the nonspecific binding sites of the plate. The blocking solution was removed by inverting the plate and shaking vigorously. The collected serum was diluted a thousand times in regular PBS and each well was loaded with 50 µl of such diluted sera. PBS only wells were served as negative control while a positive sample were diluted at 1/10, 1/30, 1/90, 1/270, 1/810, 1/2430 and 1/7290 to generate a standard curve. Duplicates or triplicates for each tested serum were performed. After a 2-hour incubation at room temperature, five washes with buffer B were performed in the plate washer.

To test anti-TPP1 IgG, primary antibody, which is HRP conjugated goat anti mouse IgG antibody, was diluted at 1:10,000 in blocking buffer. 100 µL of prepared primary antibody was added to each well and incubated for 1 hour at room temperature. Five washes with buffer B were performed in the plate washer. 150 µl HRP substrate (3,3',5,5'-Tetramethylbenzidine, TMB) were loaded to each well. 1 to 30 minutes incubation in dark was allowed for develop a detectable color. 50 µl stop buffer (sulfuric acid) were added to each well with gentle pipetting if necessary. Signal at 450 nm was measured using a plate reader.

For detecting anti-TPP1 IgM, the same protocol as described above were performed with following modifications. The primary antibody was goat anti mouse IgM. After incubation with primary antibodies, five washes with buffer B were performed followed by a 30 minute incubation with 100 µl HRP conjugated anti-goat secondary antibody diluted at 1:10,000 in blocking buffer.

Figure 7A:
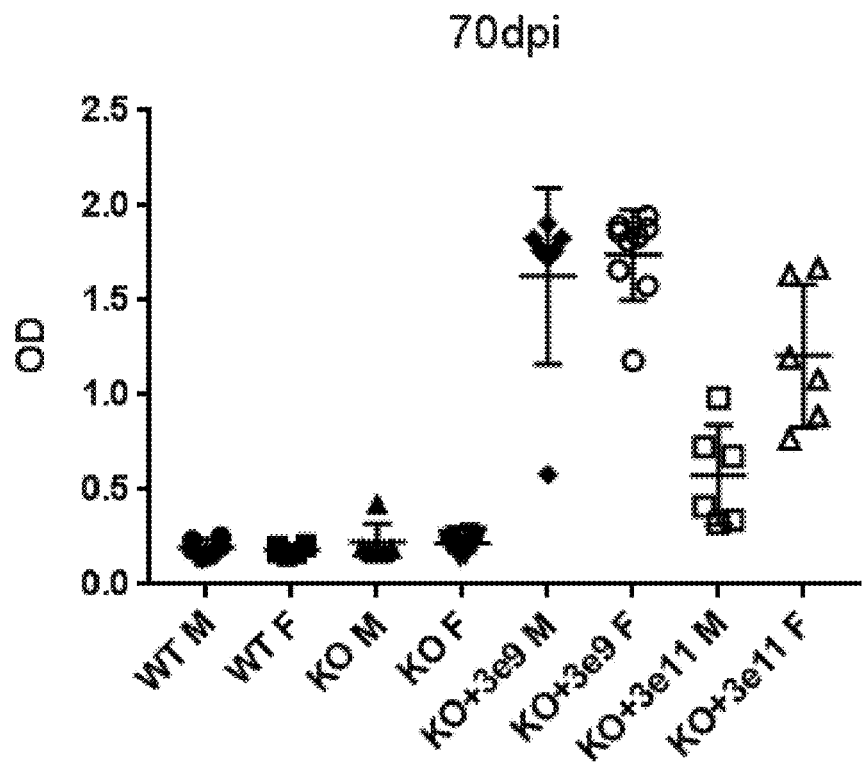
FIG. 7A is an ELISA result showing the generation and amount of anti-TPP1 antibodies in the sera of TPP1 KO mice treated with PBS only, $3 \times 10^9$ GC or $3 \times 10^{11}$ GC of the AAV.hTPP1co as described in Example 5. Wildtype mice were served as control. In each group, both male and female animals were tested and recorded separately to reveal potential gender differences. The optical density (OD) measured were plotted in y axis. A higher OD value indicates a larger amount of anti-TPP1 antibodies.
Figure 7B:
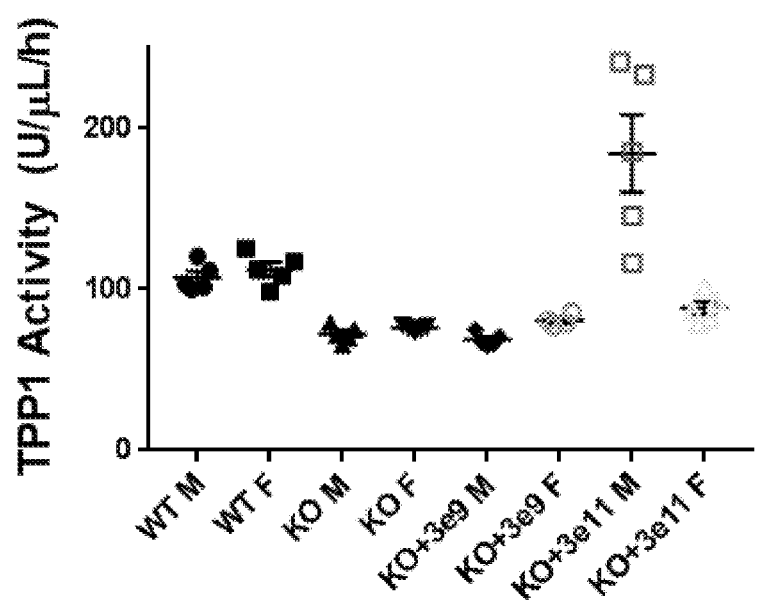
FIG. 7B provides results of TPP1 enzyme activity tested in the sera of TPP1 KO mice treated with PBS only, $3 \times 10^9$ GC or $3 \times 10^{11}$ GC of the AAV.hTPP1co as described in Example Wildtype mice were served as control. In each group, both male and female animals were tested and recorded separately to reveal potential gender differences.

Both low dose treated male and female KO mice and high dose treated female mice showed strong immune responses against TPP1 (FIG. 7A), demonstrating this immune response was independent of the therapeutic dose. Male KOs treated with high dose of the AAV.hTPP1co vectors showed moderate immune response. The concomitant TPP1 enzymatic activity in the same sera was measured as described in Examples 2 and 4 and plotted in FIG. 7B and FIG. 20. Enzyme activity was inversely correlated with presence of anti-TPP1 antibody. Nevertheless, no difference in therapeutic efficacy was observed between male and female high dose as shown in Example 5, suggesting no negative impact of the anti TPP1 immune response.

D. TPP1 Enzyme Activity

Figure 8:
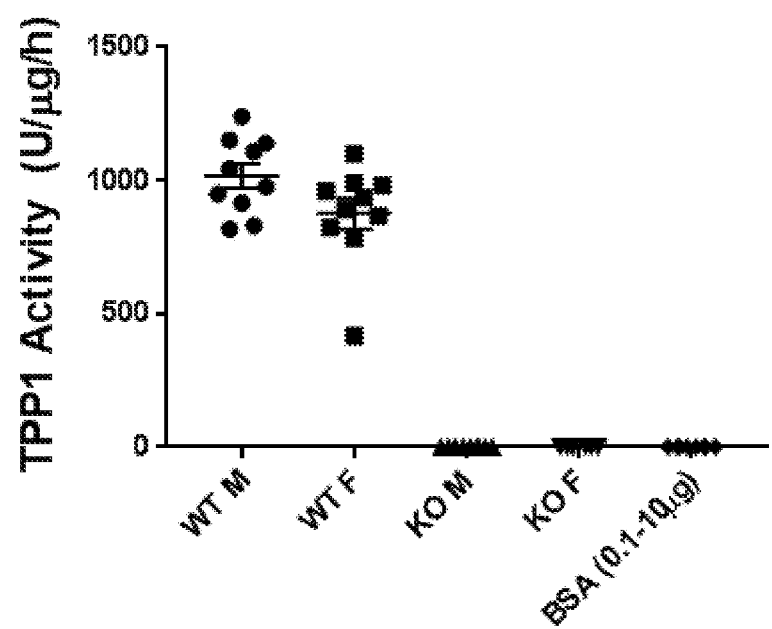
FIG. 8 provides results of TPP1 enzyme activity tested in the brain section comprising part of lateral ventricle (LV), hippocampus and thalamus of TPP1 KO mice as well as wildtype mice as described in Example 5. 0.1 to 10 µg of BSA was utilized as negative control.
Figure 9:
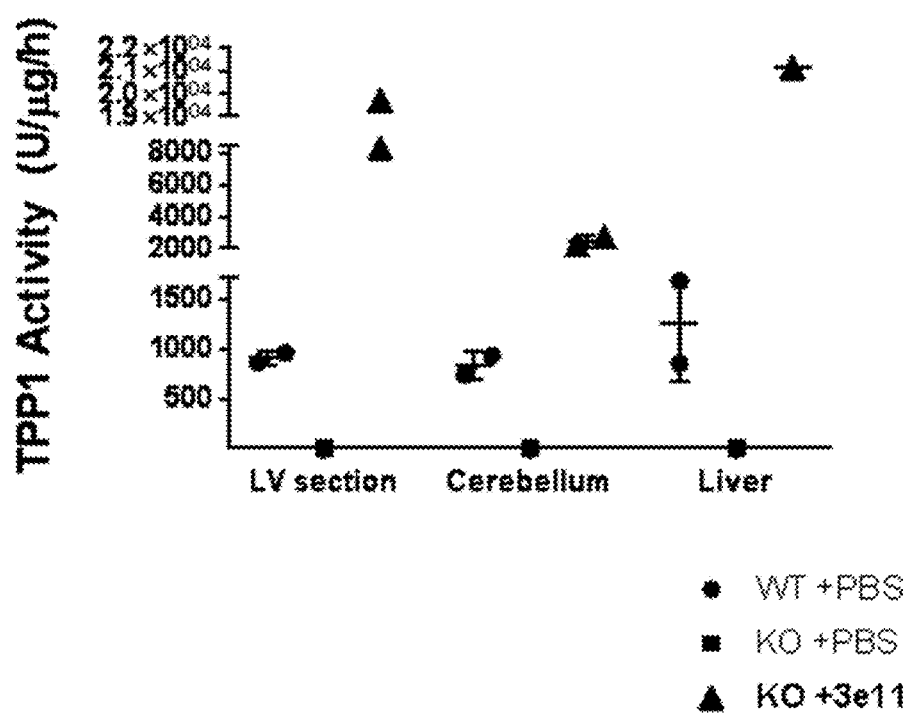
FIG. 9 provides results of TPP1 enzyme activity tested in the brain section (labelled as LV section, comprising part of lateral ventricle (LV), hippocampus and thalamus) as well as cerebellum and liver of TPP1 KO mice injected with PBS only or $3 \times 10^{11}$ GC of AAV.hTPP1co, and wildtype mice injected with PBS only as described in Example 5.

To evaluate the TPP1 enzymatic activity in different organs as well as to assess enzymatic correction in affected tissues (mostly brain), TPP1 enzyme activity was measured as described in Examples 2 and 4. Brain tissues, such as cortex and sections comprising part of lateral ventricle (LV), hippocampus and thalamus (labelled as LV section in FIG. 9), were harvested, dissected and processed as described in Example 4. No TPP1 activity was observed in 3-month-old male and female TPP1 KO mice and thus was used as baseline demonstrating the total absence of residual TPP1 in the KOs while one-month-old wildtype mice demonstrated a normal and detectable level of TPP1 activity (FIG. 8). Similar result was observed in other organs, including cerebellum and liver in the wildtype mice as well as the KOs injected with PBS only (FIG. 9). TPP1 enzyme activity treated with $3\times10^{11}$ GC of the AAV.hTPP1co described above were also measured and plotted in FIG. 9 for comparison. In the three different organs tested (LV section, cerebellum and liver), high dose vector treated KOs provided more TPP1 activity than wild type while the TPP1 activity level of KO injected with PBS stayed low and thus was subtracted from all samples shown in FIG. 9, demonstrating a successful cellular enzymatic correction and a healthy phenotype in KO mice treated with hAAV.hTPP1co.

Figure 20:
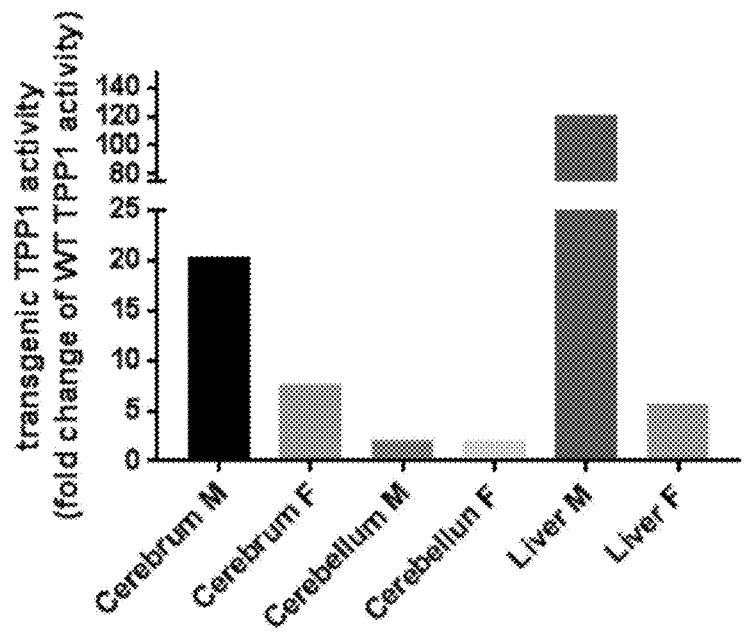

In high-dose animals, TPP1 enzymatic activity (the enzyme encoded by AAV9.CB7.hCLN2) was increased to supraphysiological levels in the cerebrum, cerebellum, and liver at 30 weeks post-injection (FIG. 20).

E. Histological Analysis

To assess the bioactivity and efficacy of ICV injection of AAV.hTPP1co in the brain, brain samples of the tested mice were stained for GFAP, a marker of activated astrocytes/astrocytosis, via immunohistochemistry. Images not shown. Both cortex and thalamus of one-month-old wildtype mice showed no GFAP but the corresponding samples of the KO animals were observed with astrocytosis at one month of age, indicating that astrocytes were activated by accumulation of lipids in neurons due to TPP1 mutation and such astrocytosis progress started at one month old or earlier. In KO mice, astrocytosis kept increasing upon growth. At 3 months of age, a further elevated level of GFAP was detected in both cortex and thalamus in the KO mice. In the survival curve shown in FIG. 4, death of KO animals was observed starting at 3.5 months of age, which is consistent with the reported links between activated astrocytes and neuronal death observed in different parts of the brain of NCL patients and animal models. Thus, this neuronal loss conferred the disease phenotype of tremor and motor coordination abnormality observed in the KO. This conclusion was further supported by the massive astrocytosis observed via GFAP immunostaining in hippocampus sections adjacent to lateral ventricles of the 3.5 month-old KO mice injected with PBS and found dead as described in Example 4.

Furthermore, GFAP staining was performed only at 4.5 months of age using the brain samples of KO animals treated with $1 \times 10^{11}$ GC of the AAV.hTPP1co described above as well wildtype and KO mice injected with PBS. The brain of AAV.hTPP1co treated mice was clear of astrocytosis with an observation similar to wildtype, indicating that the AAV.hTPP1co therapy not only controlled but also actively repressed activated astrocytes. Quantification of astrocytosis is performed. In high-dose animals, brain neurons exhibited corrections in astrocytosis (marker of neuroinflammation) and lysosomal accumulation of substrates at 30 weeks post-injection (FIG. 9).

In view of the above, the enzyme activity and physiological phenotype of TPP1 KO mice were successfully restored via administration of AAV.CB7.CI.hTPP1co.RBG.

Example 6: Manufacturing

Briefly, HEK293 cells from the master cell bank (MCB) are transfected with 3 plasmids to produce the packaged vector genome: a plasmid containing the CLN2 expression cassette and 2 helper plasmids encoding AAV9 capsid proteins and replication elements. Cell culture supernatant containing the viral vector product is harvested, clarified, and concentrated by tangential flow filtration (TFF) followed by affinity and anion exchange (AEX) chromatography. The AEX fractions are pooled and TFF is repeated to produce purified bulk drug substance (BDS) from which drug product is produced by adjusting concentration (dilution or concentrating via TFF) with final formulation buffer followed by sterile filtration and filling into a vial. The AAV9.CB7.hCLN2 BDS and final drug product (FDP) manufacturing processes will be performed at a contract manufacturing organization(s) (CMOs) using current Good Manufacturing Practices (cGMPs) to ensure safety, identity, quality, purity, and potency of BDS and FDP.

Cell Culture and Harvest

The cell culture and harvest manufacturing process comprises 4 main manufacturing steps: cell seeding and expansion, transient transfection, vector harvest, and vector clarification. These process steps are depicted in the overview process flow diagram.

Cell Seeding and Expansion: A qualified HEK293 cell line is used for the production process. A MCB was produced at WuXi AppTec and fully characterized. Cell culture used for vector production is initiated from a single, thawed MCB vial and expanded. Cells are expanded to achieve a total viable cell count of approximately $1.4 \times 10^{10}$ cells using T-flasks and 10-layer cell culture chambers (CS-10). The culture is expanded in 4 stages using increasingly larger surface areas (1×T-75, 4×T-225, 2×CS-10, and 14×CS-10). In the first stage, the cells are grown for 3-4 days until confluent and then passaged to the next stage. In subsequent stages, cells are grown for 4-5 days, then passaged. This expansion allows sufficient cell mass to be generated for seeding up to fifty 36-layer cell culture vessels (HS-36s) for vector production per BDS lot. Cells are cultivated in medium composed of Dulbecco's Modified Eagle Medium (DMEM), supplemented with 10% gamma irradiated, US-sourced, fetal bovine serum (FBS) throughout the expansion process. The cells utilized are anchorage dependent and cell disassociation is accomplished using TrypLE Select, an animal product-free cell dissociation reagent. Cell seeding is accomplished using sterile, single-use disposable bioprocess bags and tubing sets. The cells are maintained at 37° C. (±2° C.), in 5% (±0.5%) CO2 atmosphere. The total process time from vial thaw through inoculation of the 50 HS-36s is 15-20 days.

Transient Transfection: Following 4 days of growth (DMEM media+10% FBS), HS-36 cell culture media is replaced with fresh, serum-free DMEM media and transfected with the 3 production plasmids using an optimized polyethylenimine (PEI)-based transfection method. Sufficient DNA plasmid transfection complex is prepared in the biological safety cabinet (BSC) to transfect up to 50 HS-36s (per BDS batch). Initially, a DNA/PEI mixture is prepared containing 7.9 mg of pAAV.CB7.CI.CLN2.RBG.KanR vector genome plasmid, 158 mg of pAdDeltaF6, 79 mg of pAAV29KanRGXRep2 AAV plasmid and PEI (PEIPro, PolyPlus Transfection SA). After mixing, the solution is allowed to sit at room temperature for 25 min and then added to serum-free media to quench the reaction and then added to the HS-36s. The transfection mixture is equalized between all 36 layers of the HS-36 and the cells are incubated at 37° C. (±2° C.) in a 5% (±0.5%) CO2 atmosphere for 5 days.

Vector Harvest: The cell culture supernatant is harvested from the HS-36s by aseptically pumping the supernatant into disposable bioprocess bags. Following collection, the harvest material is supplemented with MgCl2 to a final concentration of 2 mM (co-factor for Benzonase) and Benzonase nuclease is added to a final concentration of ≥25 units/mL. The harvest material (in a disposable bioprocess bag) is mixed and incubated at 37° C. for 2 h to provide sufficient time for enzymatic digestion of residual cellular and plasmid DNA present in the harvest as a result of the transfection procedure. This step is performed to minimize the amount of residual DNA in the final vector drug product. After the incubation period, NaCl is added to a final concentration of 500 mM to end digestion and aid in the recovery of the product during filtration and downstream tangential flow filtration (TFF).

Vector Clarification: Cells and cellular debris are removed from the Benzonase-treated harvest material using a Sartoguard polyethersulfone (PES) capsule filter (1.2/0.2 µm; Sartorius Stedim Biotech Inc.) connected in series as a sterile, closed tubing and bag set that is driven by a peristaltic pump. Bioburden reduction filtration ensures that at the end of the filter train, any bioburden potentially introduced during the upstream production process will be reduced before downstream purification.

Vector Purification Process

The purification process comprises 4 main manufacturing steps that are described in detail below: concentration and buffer exchange by TFF, affinity chromatography, anion exchange chromatography, and concentration and buffer exchange by TFF.

Concentration and Buffer Exchange by Tangential Flow Filtration: Volume reduction (10-fold) of the clarified product is achieved by TFF using a custom sterile, closed bioprocessing tubing, bag and membrane set. The principle of TFF is to flow a solution under pressure parallel to a membrane of suitable porosity (100 kDa). The pressure differential drives molecules of smaller size through the membrane and effectively into the waste stream while retaining molecules larger than the membrane pores. By recirculating the solution, the parallel flow sweeps the membrane surface preventing membrane pore fouling. By choosing an appropriate membrane pore size and surface area, a liquid sample may be rapidly reduced in volume while retaining and concentrating the desired molecule. Diafiltration in TFF applications involves addition of a fresh buffer to the recirculating sample at the same rate that liquid is passing through the membrane and to the waste stream. With increasing volumes of diafiltration, increasing amounts of the small molecules are removed from the recirculating sample. This results in a modest purification of the clarified product, but also achieves buffer exchange compatible with the subsequent affinity column chromatography step. Accordingly, a 100 kDa, PES membrane is used for concentration that is then diafiltrated with ≥3.3 volumes of a buffer composed of 20 mM Tris, 400 mM NaCl, pH 7.5. The diafiltered product is then stored at 2-8° C. for ≥16 h and then further clarified with a 1.2/0.2 µm depth filter capsule to remove any precipitated material. The process time for the harvest, clarification, and concentration steps is approximately 2 days.

Affinity Chromatography: The diafiltered product is subsequently applied to a POROS® CaptureSelect® AAV9 affinity matrix (Life Technologies) that efficiently captures the AAV9 serotype. Under these ionic conditions, a significant percentage of residual cellular DNA and proteins flow through the column, while AAV9 particles are efficiently captured. Following application, the column is washed using two buffers (20 mM Tris, 1 M NaCl, pH 7.5 and 20 mM Tris, 400 mM NaCl, pH 7.5) to remove additional feed impurities followed by a low pH step elution (400 mM NaCl, 20 mM Sodium Citrate, pH 2.5). The eluate is immediately neutralized by the addition of neutralization buffer (200 mM Bis Tris Propane, 0.01% Pluronic F68, pH 10.2) at 10% the volume of the eluate. The process time for affinity chromatography step is less than 1 day. The process intermediate may be held overnight at 2-8° C. prior to further processing.

Anion Exchange Chromatography: To achieve further reduction of in-process impurities including empty AAV particles, an anion exchange chromatography step is employed. For this step, the POROS-AAV9 elution pool is diluted 50-fold (20 mM Bis Tris Propane, 0.001% Pluronic® F68, pH 10.2) to reduce ionic strength to enable binding to a CIMmultus QA monolith matrix (BIA Separations). Following a low-salt wash (20 mM Bis-Tris Propane, 10 mM NaCl, pH 10.2), vector product is eluted using a 60-column volume (CV) NaCl linear salt gradient (10-190 mM NaCl in 20 mM Bis Tris Propane, 0.001% Pluronic F68, pH 10.2). This shallow salt gradient separates capsid particles without a vector genome (empty particles) from particles containing vector genome (full particles) and results in a preparation enriched for full capsids. Fractions are collected into bags containing 3.7% volume of 1 M Bis Tris, 0.27% Pluronic F68, pH 6.3 to minimize non-specific binding to bags and the length of exposure to high pH, respectively. The appropriate peak fractions are collected and pooled. The process time for anion exchange chromatography step is less than 1 day. The process intermediate may be held overnight at 2-8° C. prior to further processing.

Concentration and Buffer Exchange by Hollow Fiber Tangential Flow Filtration: The pooled anion exchange intermediate is concentrated and buffer exchanged by using TFF. In this step, a 100 kDa membrane hollow fiber TFF membrane is used. During the step, the product is brought to a determined target concentration. Following this concentration step, buffer exchange is achieved by diafiltration with 4 volumes of formulation buffer. Samples are removed for BDS testing after 0.45/0.22 µm filtration. The process time for the concentration and buffer exchange step is less than 1 day.

Filling and Storage: Following filtration and sampling, the BDS is filled into polypropylene bottles and stored frozen at ≤−60° C. in a quarantine location until release for FDP processing.

TABLE 1

| Proposed Formulation for AAV9.CB7.hCLN2 Excipient | Proposed formulation for AAV9.CB7.hCLN2 (mM) |
| --- | --- |
| Sodium Chloride | 150 |
| Magnesium Chloride | 1.2 |
| Potassium Chloride | 3 |
| Calcium Chloride | 1.4 |
| Sodium Phosphate | 1 |
| Dextrose | 4.4 |
| Poloxamer 188 | 0.001% |

Thaw and Pooling: Frozen aliquots of BDS are thawed at room temperature. Multiple BDS batches may be pooled and mixed via swirling. The thawed BDS may be held overnight at 2-8° C.

Optional Concentration by TFF or Dilution: The BDS may be concentrated using hollow fiber TFF, or diluted with formulation buffer, to achieve the desired concentration (in GC/mL). The optional concentration step is performed using TFF with a 100 kDa hollow fiber TFF membrane, and is identical to the hollow fiber TFF concentration step in the BDS process. The concentrated DP intermediate may be held overnight at 2-8° C.

Sterile Filtration: A bioburden sample of the DP intermediate is taken immediately prior to filtration. The DP is 0.22 µm filtered using a pre-sterilized assembly. The 0.22 µm filter (Pall miniKleenpak 20 with Fluorodyne II) is flushed with formulation buffer, then drained. The DP intermediate is then filtered, and the filter, which is pre-use integrity tested by the filter manufacturer, is post-use integrity tested prior to filling the DP into vials. If the filter fails post-use integrity testing, the filtered intermediate may be re-filtered using a different filter. Filling, Storage, and Transportation: Filtered DP is filled into CZ vials using a peristaltic pump. The initial vials will be filled at a volume optimized for testing (for example 1 mL in a 10 mL vial). These will be used for sterility, endotoxin, and other release or stability testing. The fill volume will be increased for the next set of vials (for example 5 mL in a 10 mL vial), which will be used in the clinic. The final set of vials will again be filled at a lower volume (for example 1 mL in a 10 mL vial), and used for sterility, endotoxin, and other release or stability testing. Weight checks are performed at pre-defined intervals. Vials are capped and crimped, then 100% visually inspected, labelled, packaged in cartons, and frozen at ≤−60° C.

For shipping to clinical sites, the FDP vials previously packaged into cartons are placed into a pre-qualified cardboard shipping box with a temperature logger. The box is filled with dry ice to maintain the shipping temperature of ≤−60° C. Upon receipt of the shipment, the temperature logger is read to confirm no temperature excursion during shipping.

Example 7: Future Studies

In the proposed study, AAV9.CB7.hCLN2 will be administered via ICV injection in 4 week old mice at a dose level range of $2 \times 10^{10}$ GC/g brain mass to the maximum feasible dose (MFD) of $7.5 \times 10^{11}$ GC/g brain mass (due to anatomic constraints). Half of the animals will be sacrificed at 60 days post-injection to coincide with expected neuropathology and mortality in control animals and evaluated for bioactivity, including TPP1 enzymatic activity, accumulation of lysosomal storage material and storage pathology, and astrocytosis. The remainder of the animals will be evaluated for the time to onset of disease phenotype (defined by tremor and/or gait abnormality upon clinical observations) and followed for long-term survival for up to 210 days post-injection, which is beyond when 100% mortality is expected in control animals.

AAV9.CB7.hCLN2 will be administered to Tpp1m1j mice via ICV injection in the proposed study, as was done in the pilot study, because: i) IC injections are not feasible in Tpp1m1j mice due to anatomic constraints and animal welfare concerns; and ii) the biodistribution (BD) and transgene expression profiles of AAV9 vector-based products following ICV injection in mice and IC injection in canines, pigs, and non-human primates (NHPs) have been shown to be comparable (Haurigot et al., 2013; Hinderer et al., 2017; McLean et al., 2014; unpublished data) (see Section 3.4.2.5). Importantly, these similarities include the primary target tissues of vector BD and subsequent transgene expression in the CNS (brain, spinal cord) and peripheral tissues (liver, spleen), which enable the assessment of transgene expression/over-expression in both target and non-target tissues. Thus, pharmacology data generated in Tpp1m1j mice following ICV injection of AAV9.CB7.hCLN2 are relevant to the clinical scenario and planned IC ROA in the target patient population.

Example 8: Preclinical Studies

The proposed preclinical testing program for AAV9.CB7.hCLN2 includes a Hybrid Pharmacology/Toxicology study conducted in the Tpp1m1j mouse model of CLN2 disease. Mice administered AAV9.CB7.hCLN2 via ICV injection at multiple dose levels will be evaluated for safety at multiple timepoints, as follows:
- Clinical observations (cage-side, daily)
- Body weight (weekly)
- Clinical pathology (d60, d90, d210)
- Humoral immune response in serum (anti-hTPP1 antibodies in serum, ELISA) (baseline, d14, d60, d210)
- Organ weights (d60, d90, d210)
- Gross pathology and histopathology of a comprehensive list of tissues (d60, d90, d210)

In general, hybrid study designs facilitate the evaluation of the safety of a test article in a disease setting that reproduces the local microenvironment and pathophysiology status of the target patient population, which may impact the safety and bioactivity of the product in the clinical setting. Thus, safety/toxicology data generated from the proposed Hybrid Pharmacology/Toxicology study are anticipated to provide important information regarding the safety profile of AAV9.CB7.hCLN2. As per Agency guidance recommendations, "The animal species selected for assessment of bioactivity and safety should demonstrate a biological response to the investigational [product] similar to that expected in humans in order to generate data to guide clinical trial design." Therefore, the selection of the Tpp1m1j mouse model of CLN2 disease is appropriate for the evaluation of the safety of AAV9.CB7.hCLN2.

There are some potential challenges of assessing safety in Tpp1m1j mice, including the concern that the underlying pathology and early mortality in the diseased Tpp1m1j mice may mask potential test article-related effects and that the ability to perform some safety assessments (such as serial bleeds) may be limited due to the susceptibility of Tpp1m1j mice to environmental stimuli-induced fatal seizures. If these concerns are borne out by experience and the Tpp1m1j mouse safety data are not considered sufficient to satisfy regulatory requirements, an additional GLP-compliant toxicology study will be conducted in C57Bl/6 mice. C57Bl/6 mice are considered appropriate for detecting potential toxicities associated with AAV9.CB7.hCLN2 because: i) the C57Bl/6 mouse is the background strain for the Tpp1m1j mouse model used in pharmacology assessments; ii) the comparability of biodistribution and transgene expression profiles of AAV9 vector-based products following ICV injection in mice and IC injection in large animals has been established; iii) the feasibility of performing safety assessments in healthy mice is not limited by animal handling concerns or susceptibility to environmental stimuli-induced fatal seizures, such as in the Tpp1m1j mouse; and iv) the conduct of GLP-compliant safety/toxicology studies in healthy mice is feasible, well-established, and statistically-robust.

In this potential GLP Safety/Toxicology study, AAV9.CB7.hCLN2 will be administered at a dose level of $7.5 \times 10^{10}$, $2 \times 10^{11}$ and the MFD of $7.5 \times 10^{11}$ GC/g brain mass via ICV injection in 4-week old C57Bl/6 mice, and mice will be evaluated for safety/toxicity at multiple time points. The planned scheduled sacrifices (30 and 90 days post-injection) and study duration (90 days post-injection) were selected to coincide with the kinetics of AAV9 vector biodistribution and progression of the disease phenotype in Tpp1m1j mice. Safety assessments will include clinical observations, body weight, clinical pathology, immunogenicity, gross pathology, and histopathology of a comprehensive list of tissues.

There are several reported animal models of CLN2 disease, including canine and murine models. The most well-characterized in the scientific literature is the TPP1-null canine model first reported in a population of Dachshunds (Awano et al., 2006), although limited availability of this animal model and breeding constraints severely restricts the feasibility of its use in preclinical testing. The most commonly reported mouse model of CLN2 disease in the scientific literature is the Tpp1tm1Plob mouse model (Sleat et al., 2004), although this mouse model is not currently commercially-available and thus is not feasible for use in preclinical testing. The Tpp1m1j mouse model of CLN2 disease, which is highly similar to the Tpp1tm1Plob mouse and TPP1-null canine models, is commercially available and recapitulates characteristic features of CLN2 disease in humans. This Tpp1m1j mouse model results from a single nucleotide mutation in the splice donor site downstream of exon 8 of the CLN2 gene. As a result of this mutation, Tpp1m1j mice exhibit undetectable levels of TPP1 enzymatic activity in brain tissue, as well as a similar pathophysiology, phenotype, and mortality as humans with CLN2 disease (Karst et al., 2016; unpublished data from natural history study).

Completed pilot studies conducted in the biologically-relevant mouse model of CLN2 disease (Tpp1m1j mice) provide preliminary support for the scientific rationale of the AAV9-mediated delivery of a codon-optimized CLN2 transgene for the treatment of CLN2 disease. In completed pilot studies, 4-week old Tpp1m1j mice were administered AAV9.CB7.hCLN2 at a dose level of either $7.5 \times 10^9$ GC/g brain mass (low-dose) or $7.5 \times 10^{11}$ GC/g brain mass (high-dose) via ICV injection, and animals were monitored for disease progression and bioactivity for 30 weeks post-injection. Animals administered AAV9.CB7.hCLN2 at the high-dose exhibited normalization of motor learning (cerebellum function) compared to wild-type controls, as well as dramatically increased survival (85% survival at 30 weeks post-injection versus 0% survival in control animals). All surviving animals were sacrificed at 30 weeks post-injection for evaluation of TPP1 enzymatic activity and histopathology. In high-dose animals, TPP1 activity (the enzyme encoded by AAV9.CB7.hCLN2) was increased to supra-physiological levels in the cerebrum, cerebellum, and liver, and brain neurons exhibited corrections in astrocytosis and lysosomal accumulation of substrates. There did not appear to be benefit in survival or other measures of bioactivity in Tpp1m1j that were administered AAV9.CB7.hCLN2 at the low-dose ($7.5 \times 10^9$ GC/g brain mass), with an observed median survival of ~17 weeks in both low-dose and control animals.

AAV9.CB7.hCLN2 was administered to Tpp1m1j mice via ICV injection in pilot studies (and is planned for the definitive pharmacology and safety/toxicology studies), which is different than the planned clinical IC route of administration (ROA). However, IC injections are not feasible in Tpp1m1j mice due to anatomic constraints and animal welfare concerns. While IC administration offers several advantages over ICV in the clinic, data from multiple animal studies have shown similar biodistribution (BD) and transgene expression profiles of AAV9 vector-based products following ICV injection in mice and IC injection in canines, pigs, and non-human primates (NHPs) (Haurigot et al., 2013; Hinderer et al., 2017; McLean et al., 2014; unpublished data). Thus, pharmacology data generated in Tpp1m1j mice following ICV injection of AAV9.CB7.hCLN2 are relevant to the clinical scenario and planned IC ROA in the target patient population.

Data generated from pilot studies, as well as platform data from the preclinical testing programs of similar AAV9 vector-based products, were used to inform the design of the planned IND-enabling Hybrid Pharmacology/Toxicology study in a biologically-relevant murine model of CLN2 disease, Tpp1m1j mice. In the proposed study, AAV9.CB7.hCLN2 will be administered via ICV injection in 4-week old mice, at a vector dose level range of $2 \times 10^{10}$ GC/g brain mass to the MFD of $7.5 \times 10^{11}$ GC/g brain mass. Animals will be evaluated for numerous measures of bioactivity and safety/toxicity at multiple timepoints. Data generated from this study will be used to select a safe and efficacious starting clinical dose level and support the favorable benefit:risk profile of the administration of AAV9.CB7.hCLN2 in the target patient population.

In the event that adequate safety data are unable to be obtained from the planned Hybrid Pharmacology/Toxicology study due to animal handling and welfare concerns (ie, potential challenges to conducting some safety assessments in Tpp1m1j mice, such as serial bleeds), data may be complemented by additional safety data generated following the ICV administration of AAV9.CB7.hCLN2 in a GLP-compliant Safety/Toxicology study in C57Bl/6 mice. C57Bl/6 mice are considered appropriate for detecting potential toxicities associated with AAV9.CB7.hCLN2 because: i) the C57Bl/6 mouse is the background strain for the Tpp1m1j mouse model used in pharmacology assessments; ii) the comparability of biodistribution and transgene expression profiles of AAV9 vector-based products following ICV injection in mice and IC injection in large animals has been established; iii) the feasibility of performing safety assessments in healthy mice (eg, serial bleeds) is not limited by animal handling concerns or susceptibility to environmental stimuli-induced fatal seizures, such as in the Tpp1m1j mouse; and iv) the conduct of GLP-compliant safety/toxicology studies in healthy mice is feasible, well-established, and statistically-robust.

In this potential GLP Safety/Toxicology study, AAV9.CB7.hCLN2 will be administered at a dose level of $7.5 \times 10^{10}$, $2 \times 10^{11}$, or the MFD of $7.5 \times 10^{11}$ GC/g brain mass via ICV injection in 4-week old C57Bl/6 mice, and mice will be evaluated for safety/toxicity at multiple time points. The planned scheduled sacrifices at 30 and 90 days post-injection) and study duration (90 days post-injection) were selected to coincide with the kinetics of AAV9 vector biodistribution and progression of the disease phenotype in Tpp1m1j mice. Safety assessments will include clinical observations, body weight, clinical pathology, immunogenicity, gross pathology, and histopathology of a comprehensive list of tissues.

Proof-of-Concept (POC) and Pharmacology

Scientific Rationale for Increasing TPP1 Enzymatic Activity in the CNS to Treat CLN2 Disease The scientific rationale for the targeting of increases in TPP1 enzymatic activity as treatment for CLN2 disease is supported by preclinical and clinical experience with ERT and the administration of Brineura® in the treatment of CLN2 disease (Katz et al., 2014; Brineura®, FDA Summary of Basis of Approval; Brineura® EPAR; Schulz et al., 2016). The biweekly infusion into the lateral ventricles of Brineura® via a permanently implanted device was determined to stabilize motor function in patients with CLN2 disease by the FDA, while the EMA determined that there was a positive impact on language skills as well. The CSF and lysosomal half-lives of Brineura® is estimated to be 7 hours and 11.5 days, respectively; as a result, repeat infusions of Brineura® are necessary to maintain elevated TPP1 enzymatic activity levels (and presumably clinical benefit). Thus, there remains an unmet need for new therapies that can provide durable and long-term TPP1 enzymatic activity in the CNS without the high patient burden and morbidities associated with repeat administration of ERT.

Scientific Rationale for AAV9-Mediated Gene Transfer of CLN2 to Treat CLN2 Disease The ability of AAV vector-based products to target the CNS has been demonstrated in numerous models of monogenic CNS disease, and several early human trials evaluating first-generation AAV vector-based products have shown the safety of vector delivery to the brain (Bartus et al., 2014; Janson et al., 2002; Kaplitt et al., 2007; Mandel et al., 2004). However, many factors including the low transduction efficiency of these first-generation AAV vectors prevented the translation of the bioactivity observed in animal models to the clinic. With the advent of second-generation AAV vectors, the potential for gene transfer to the brain has been greatly enhanced. In particular, the ability of AAV9 vector-based products to selectively target the CNS and achieve widespread gene transfer with high efficiency has been demonstrated in rodents, cats, dogs, NHPs (Foust et al., 2010; Gray et al., 2013; Hinderer, 2014 et al; Hinderer et al., 2014b; Hinderer et al., 2016; Hinderer, 2016b; Haurigot et al., 2013; Bucher et al., 2014; Passini et al., 2014; Hinderer et al., 2017; FIG. 15). This ability has led to the initiation of numerous clinical trials to evaluate AAV9 vector-based products for a variety of indications, including variant CLN6 disease, Spinal Muscular Atrophy Type I, Giant Axonal Neuropathy, MPS I, MPS IIIa, and MPS IIIb.

Figure 14:
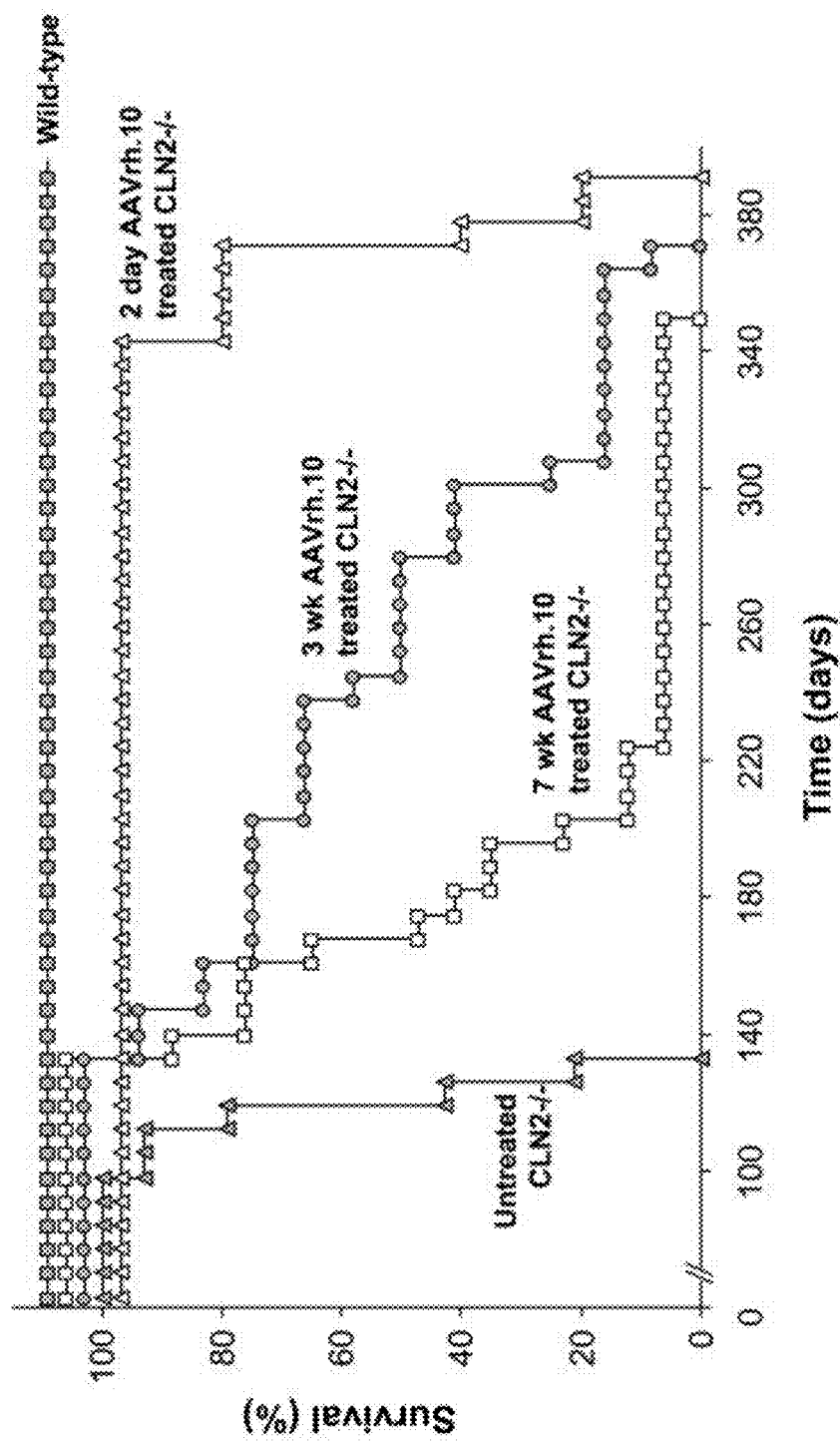
FIG. 14 demonstrates that AAVrh10 vector-based Delivery of CLN2 Prolongs Survival in CLN2−/− mice (Tpp1tm1Plob mouse model of CLN2 disease). Figure reproduced from Sondhi et al., 2008.

The successful AAV-mediated delivery of a CLN2 transgene (encoding for soluble TPP1) to the CNS has also been demonstrated in numerous animal studies conducted in mouse and dog models of disease, as well as healthy rats and NHPs (Hacket et al., 2005; Sondhi et al., 2005; Sondhi et al., 2012). The ability of an AAV2 vector expressing CLN2 to induce robust and sustained levels of TPP1 enzymatic activity in the CNS, delay disease onset, and increase survival following ICV infusion and direct striatal or cerebellar injection was demonstrated in mouse and canine models of CLN2 disease (Haskell et al., 2003; Katz et al., 2015; Katz et al., 2017). Similarly, animal studies conducted in a mouse model of CLN2 disease (Tpp1tm1Plob mice) demonstrated the ability of both AAV5 and AAVrh10 vectors to deliver the CLN2 transgene to the CNS following direct intracranial injection, with consequent increases in TPP1 expression and enzymatic activity, improvements in neurobehavioral function, and improvements in overall survival (Passini et al., 2005; Passini et al., 2006; Sondhi et al., 2007; Sondhi et al., 2008). These effects appeared to be age-dependent in mice; neonatal CLN2 mice (Tpp1tm1Plob mouse model; Sleat et al., 2004) administered the AAVrh10 vector-based product at 2 days old demonstrated persistent TPP1 expression and concomitant improvements in neurobehavioral function and survival, as compared to mice given the product at 3- and 7-weeks old (FIG. 14; Sondhi et al., 2008).

These promising animal data supported the initiation of multiple clinical trials in patients with CLN2 disease (ClinicalTrial.gov Identifiers: NCT00151216, NCT01414985, NCT01161576). In a Phase 1 clinical trial, an AAV2 vector-based product incorporating CLN2 was administered to 12 locations in the CNS via direct intracranial injection though six burr holes to ten subjects with CLN2 disease. Assessments of motor function, seizure activity, and language skills by the modified Hamburg LINCL clinical rating scale showed that the gene therapy was associated with a statistically significant slower decline in neurologic status compared with concurrent control subjects at both 12- and 18-month follow-ups (Worgall et al., 2008; Human Gene Therapy, 2004). A subsequent clinical trial evaluating an AAVrh10 vector-based product delivering the identical transgene was initiated based on the observation in animal studies that AAVrh10 vector-mediated delivery of the CLN2 transgene resulted in greater vector BD in the CNS in CLN2 (Tpp1tm1Plob) mice, as compared to AAV2, AAV5, and AAV8 vector-based products (Sondhi et al., 2007) (clinical data from this trial are not available). Collectively, these preclinical and clinical experiences support the scientific rationale of AAV-mediated delivery of the CLN2 transgene to the CNS to treat CLN2 disease; however, these AAV2 and AAVrh10 vector-based approaches incorporated a series of invasive intracranial injections to target the CNS and failed to halt disease progression in clinical testing.

AAV9.CB7.hCLN2 was developed to address these issues. The AAV9 serotype which is incorporated into AAV9.CB7.hCLN2 allows for efficient transduction of the CLN2 transgene and widespread biodistribution in the CNS following non-invasive IC injection. In patients with CLN2 disease, the non-invasive delivery of the CLN2 transgene encoding TPP1 to cells within the CNS could potentially provide a permanent source of secreted TPP1, thus restoring TPP1 enzymatic activity and allowing for the long-term correction of cells throughout the CNS. Based on published data from an animal study that evaluated mouse CLN2 mutants that express different amounts of TPP1, even low levels of TPP1 enzymatic activity appear to be sufficient to dramatically delay disease onset and increase survival: approximately 3% of normal TPP1 activity in brain delayed disease onset and doubled lifespan to a median of ~9 months compared to mice expressing ~0.2% of normal levels; expression of 6% of normal TPP1 activity dramatically attenuated disease, with a median lifespan of ~20 months which approached that of unaffected mice (Sleat et al., 2008). Additional clinical data from patients with CLN2 disease suggest that certain mutations in CLN2 may lead to an incomplete loss of TPP1 enzymatic activity (at least in peripheral tissues) and a subsequently protracted phenotype (Sleat et al., 1999; Bessa et al., 2008; Schulz et al., 2013). Thus, even modest levels of TPP1 enzymatic activity in the target patient population may be clinically meaningful.

Example 9: Biodistribution of AAV9/Safety in NHP

The biodistribution (BD) of AAV9 vector-based products following IC injection have been characterized in multiple species, including cats, dogs, and NHPs for up to two years post-injection as part of the preclinical testing programs for similar products. To summarize, similar AAV9 vector-based products widely distributed and persisted in the brain and spinal cord after intracisternal (IC) injection in a variety of animal species. Where multiple dose levels were evaluated, vector tissue levels were roughly dose-dependent. Vector distribution to the liver and spleen were generally as high, and sometimes higher, than that observed in the brain. Vector concentrations in tissues other than the CNS and liver were highly variable both within studies and between studies, but the majority of tissues evaluated contained vector. Overall, data collected across multiple studies showed consistent BD profiles (kinetics and target tissues/organs) for AAV9 vector-based products, with wide distribution in the CNS (brain, spinal cord) and periphery (liver, spleen).

These pre-existing data on the BD of similar AAV9 vector-based products (and their animal analogues) are applicable to AAV9.CB7.hCLN2 because the products are similar, and the BD of viral-mediated vectors is believed to be primarily independent of the transgene (Brandon et al., 2010; Tiesjema et al., 2010; Gonin et al., 2004; Cearley et al., 2006; Zincarelli et al., 2008).

The safety of the planned clinical route of administration (ROA), intracisternal (IC) injection (intrathecal delivery via image-guided suboccipital puncture into the cisterna magna), is based on safety data from GLP-compliant NHP studies conducted as part of the preclinical testing program for a similar AAV9 vector-based product. Briefly, the administration procedure was well-tolerated in all animals; there were no clinical, gross, or histological findings related to the administration procedure in any animals at 14, 30, or 90 days post-IC injection.

The scientific rationale for the use of immunosuppression in the planned clinical trial is based in part on histopathologic findings of minimal-mild axonopathy and neuronal degeneration in the CNS and dorsal root ganglia of NHPs administered similar AAV9 vector-based products, findings which appeared to be at least partially immunologically-mediated although were not associated with any observed clinical abnormalities.

Example 10: Clinical Trial

In the FIH clinical trial titled "AAV9.CB7.hCLN2 Gene Therapy: An Open-Label, Multicenter, Sequential Single Intracisternal Dose Escalation Study in Pediatric Subjects with Late-Infantile Neuronal Ceroid Lipofuscinosis Type 2 (CLN2) to pediatric patients with CLN2 disease during a single administration procedure via intracisternal (IC) injection. The trial will be comprised of two parts.

In Part I of the trial, the primary focus will be on safety and tolerability and up to two dose levels are planned as part of a conservative dose escalation design—subjects who are ≥2 years of age with a baseline CRS (combined motor and language domains) score of 3-5 during treatment with IT ERT (Brineura®) will be enrolled sequentially, a minimum of 8 weeks apart, with ongoing safety committee review. Trough levels of TPP1 enzymatic activity in the CSF will be measured just prior to regular IT ERT infusion. Trough TPP1 activity (ie, any residual activity from prior ERT infusion) are expected to be undetectable/low from the ongoing ERT treatment based on the short half-life of Brineura®, while sustained TPP1 activity from the gene therapy is expected to be measurable by 1-4 weeks post-injection of AAV9.CB7.hCLN2. Once trough TPP1 activity is measurable (ie, secretion of TPP1 from cells transduced following administration of AAV9.CB7.hCLN2), an Internal Safety Committee (ISC) could decide to discontinue subsequent IT ERT infusions if certain pre-specified criteria are met (eg, not yet identified, but criteria such as the suitability of stable CRS, sustained TPP1 enzymatic activity are being considered). Subjects at a minimum would receive IT ERT at 2 and 4 weeks post-injection of AAV9.CB7.hCLN2 and will have been off IT ERT for up to 4 weeks prior to the Week 8 visit. Two subjects will be dosed at the first dose level.

Figure 6:
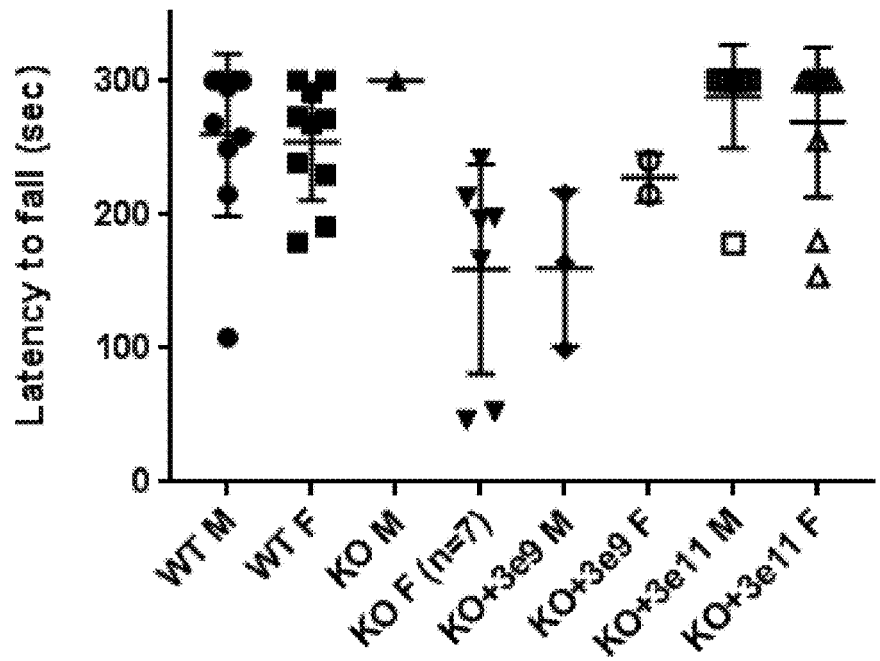
FIG. 6 provides results of motor coordination assay tested in TPP1 KO mice treated with PBS only, $3 \times 10^9$ GC or $3 \times 10^{11}$ GC of the AAV.hTPP1co as described in Example 5. Wildtype mice were served as control. In each group, both male and female animals were tested and recorded separately to reveal potential gender differences. The latency to fall was measured as the time spent on the rod in second.

In Part II of the study, an external Independent Data Monitoring Committee (IDMC) will determine if it is safe to proceed to dosing two subjects at a higher dose level in the same manner as the first dosing cohort. The highest-tolerated dose cohort may be expanded up to a total of 13 additional subjects and will include a patient population of both IT ERT-treated and IT ERT naïve subjects (FIG. 6). Inclusion/exclusion criteria will otherwise remain the same in this expanded population, including a score of 3-5 on the CLN2 Disease CRS. Criteria dictating clinically-appropriate IT ERT "rescue" infusion will be prospectively defined for patients who were previously treated with IT ERT.

In the proposed clinical trial, multiple measures of efficacy will be evaluated including TPP1 enzymatic activity in the CSF and the proportion of subjects who are categorized as responders, which is defined as subjects: i) without an unreversed (sustained) 2 category decline (ie, 1 in each of Language and Motor Domains or 2 in Motor Domain alone) in the 6-point combined Language and Motor Domains of the CLN2 Disease CRS (Steinfeld et al., 2002); and ii) without a "rescue" IT ERT infusion. Two sets of patient populations (ie, IT ERT naïve and IT ERT-treated) are planned in the Part II expansion cohort, where IT ERT naïve subjects will be followed for 72 weeks and IT ERT-treated subjects will be followed for 80 weeks, and the combined two patient populations will be compared to a natural history cohort. The primary reason to combine these two populations is to facilitate trial enrollment due to the rarity of CLN2 disease in general and the further reduction of IT ERT naïve patients following the recent approval of Brineura®.

Due to the potential impact of any residual ERT in IT ERT-treated patients and potentially confounding effects on assessment of safety and bioactivity of AAV9.CB7.hCLN2, a "wash-out" period is incorporated into the study design. Pharmacokinetic (PK) data for Brineura® in CSF and plasma suggest no apparent accumulation or PK time-dependence with a half-life of approximately 7 hours and 11.5 days in CSF and lysosomes, respectively (Brineura® EPAR), thus, the proposed "wash-out" period of up to 4 weeks following discontinuation of IT ERT is appropriate.

The assessment of language skills and development is a key component of CLN2 disease progression and thus is incorporated into the CRS (Steinfeld et al., 2002). To address any concerns regarding the utility of the Language domain of the 6-point combined Language and Motor Domains of the CRS (which were identified by FDA/CDER during review of Brineura® marketing application [Brineura®, FDA Summary Basis of Approval]), a comprehensive mitigation plan will be implemented to remove potential biases.

FDA provides multiple opportunities to expedite drug development for rare diseases and specifically addresses the targeting of a deficient gene in the FDA Draft Guidance for Industry: Expedited Programs for Serious Conditions—Drugs and Biologics—2014. This guidance also provides some insights relevant to endpoints that may be sufficient to support registration of a product for rare genetic diseases, stating that "for some well understood enzyme deficiencies, replacement of a deficient enzyme reliably predicts clinical benefit." This suggests that a gene therapy that reliably demonstrates transgene expression activity could meet the standard for accelerated approval under 21 CFR 314, subpart H. Moreover, based on this assertion, the case for early approval endpoints could be made for diseases in which deficient enzyme levels are linked to known etiology and their correction or normalization is associated with clinically meaningful effect.

In the setting of a previously-approved ERT, the correlation between enzyme levels (typically a secondary endpoint) and clinically meaningful outcomes (the precedent primary endpoint) is already established. In these instances, such as in many LSDs including CLN2 disease, successful delivery of a functioning gene copy and subsequent expression of the transgene product is evident at early timepoints (such as though measurement of reductions in CSF lysosomal storage material or enzymatic activity) well in advance of observed improvements in clinical outcomes. This suggests that enzymatic activity after gene therapy can be used as a proxy for clinical benefit. The use of enzyme activity as a basis for approval proposed is also consistent with FDA precedent, as recently stated in the FDA Directors memo accompanying the Summary Basis of Approval documents for Brineura® which states: "Since CLN2 is specifically attributed to deficiency of TPP1, reversal or prevention of its manifestations are theoretically possible if the replacement of TPP1 is durable or treatment is begun early in the course of the disease." Therefore, the potential for using TTP1 activity as an endpoint is consistent with FDA guidance.

In the proposed clinical trial, multiple measures of efficacy will be evaluated including sustained measure of TPP1 enzymatic activity in the CSF and stabilization in the 6-point combined Language and Motor Domains of the CLN2 Disease CRS. Based on the established role of TPP1 enzymatic activity in preventing pathological accumulation of lysosomal storage material and known etiology of CLN2 disease, significant and sustained increases in TPP1 activity are likely to be predictive of long-term stabilization in neurobehavioral function. Based on data from a study that evaluated mouse CLN2 mutants that express different amounts of TPP1, TPP1 enzymatic activity levels of 3-6% of normal appear to be sufficient to dramatically delay disease onset and increase survival (Sleat et al., 2008). Additional clinical data from patients with CLN2 disease suggest that certain mutations in CLN2 lead to an incomplete loss of TPP1 enzymatic activity (at least in peripheral tissues) and a subsequently protracted phenotype (Sleat et al., 1999; Bessa et al., 2008; Schulz et al., 2013). Furthermore, ERT with recombinant TPP1 (Brineura®, cerliponase alfa, BioMarin Pharmaceuticals), administered as a biweekly infusion into CSF via a permanently implanted device, was determined to stabilize declines in i) motor function over a 96-week study period by the FDA; and ii) both motor and language function over a 48-week study period by EMA. AAV9.CB7.hCLN2 is designed for the efficient and sustained expression of TPP1 in the CNS, and the one-time delivery of AAV9.CB7.hCLN2 into the CSF has the potential to provide a long-term source of the TPP1 enzyme and halt (or significantly delay) disease progression and neurocognitive decline in this rare genetic disease with high unmet need. Thus, if clinical data indicate significant and sustained measures in TPP1 enzymatic activity in the CSF at early timepoints that are suggestive of longer-term improvements in clinically meaningful stabilization in CRS, the adequacy of these data to provide primary support for the efficacy of AAV9.CB7.hCLN2 in a future marketing application will be discussed with the FDA.

Example 11: Completed Pilot Studies

Several in vitro and in vivo preclinical research and pilot studies were conducted to select the clinical candidate and collect preliminary data on the bioactivity of AAV9.CB7.hCLN2, including the Pilot Dose Ranging Study in Tpp1m1j mice (Study #W2553) (Research and pilot studies will be summarized in the IND). In Study #W2553, one-month old Tpp1m1j mice were administered AAV9.CB7.hCLN2 via ICV injection at a dose level of either 7.5×109 GC/g brain mass (low-dose; n=10/sex) or 7.5×1011 GC/g brain mass (high-dose; n=10/sex) in a total volume of 5 µl. Knock-out (n=10/sex) and wild type control (n=10/sex) animals were administered PBS via ICV injection. Animals were monitored for disease progression and survival for 30 weeks post-injection; preliminary measures of safety and bioactivity were collected at multiple time points, including clinical observations, body weight, rotarod-based neurobehavior assays (motor coordination and motor learning), humoral immune responses to the human TPP1 transgene product, TPP1 enzymatic activity in the brain and liver, astrocytosis, lysosomal accumulation of substrates, and survival.

Figure 18A:
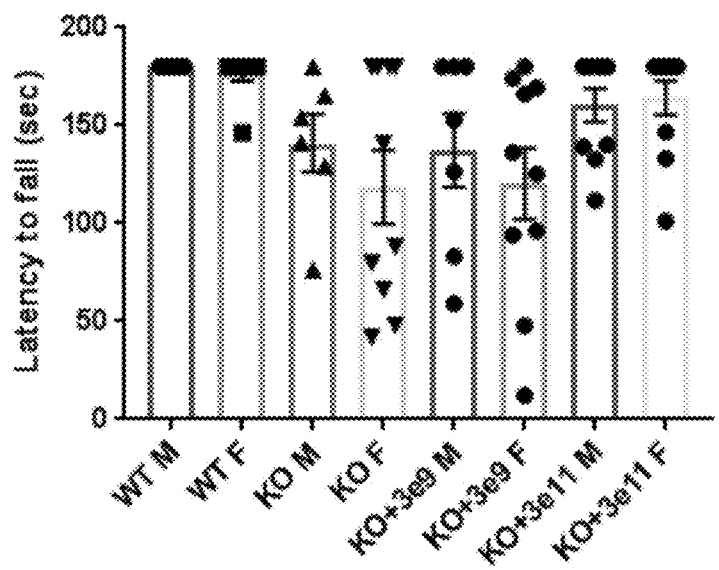
FIGS. 18A and 18B provide a neurobehavioral evaluation.
Figure 18B:
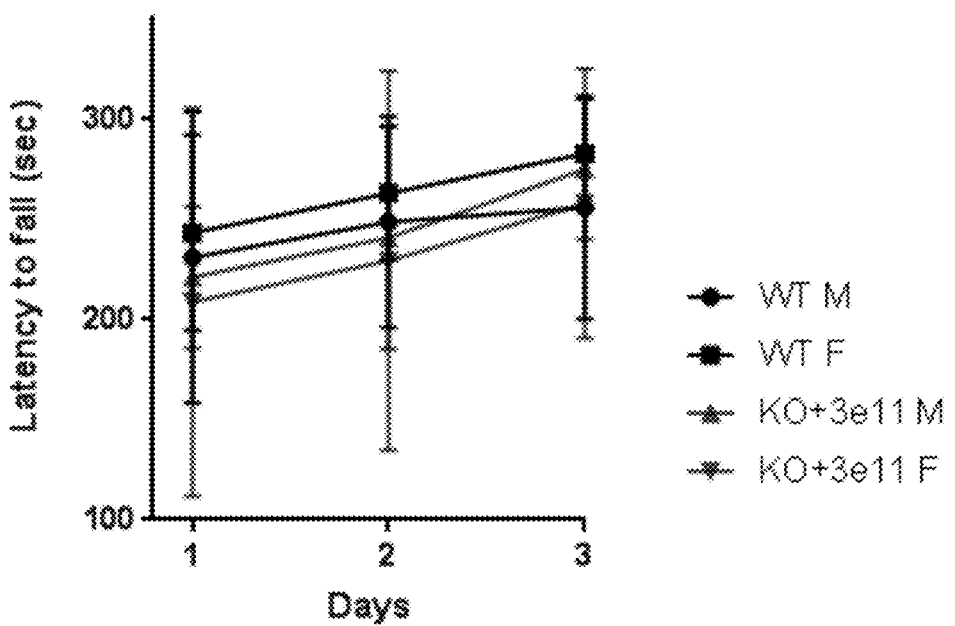

Tremors and gait abnormalities were qualitatively noted upon daily clinical observations in animals in the Tpp1m1j control and low-dose groups beginning around 8 weeks post-injection and progressively worsening for the duration of the study. Environmental stimuli-induced seizures became visible between 13 and 17 weeks of age for untreated KO and low dose treated KO, respectively. Assessments of motor coordination and motor learning were performed to evaluate neurobehavioral function in surviving animals at 7, 11 and 20 weeks post-injection. In the motor coordination assay performed at 11 weeks post-injection (180 second trial on rocking rotarod to assess latency to fall; 10 rpm), animals in the low-dose and Tpp1m1j control groups appeared to exhibit decreased function as compared to animals in the high-dose and wild-type control groups (FIG. 18A). In the motor learning assay performed at 20 weeks post-injection (300 second trial on accelerating rotarod over three consecutive days; 5-40 rpm), there did not appear to be a difference between surviving animals in the wild-type and high-dose groups (FIG. 18B), which is suggestive of a prevention of cerebellar functional decline following administration of AAV9.CB7.hCLN2 in this pilot study. Evaluation of neurobehavioral function at other time points was highly variable (data not shown).

While data from this pilot study are suggestive of an effect of AAV9.CB7.hCLN2 on the prevention of cerebellar functional decline, the utility of these neurobehavioral assays is limited in Tpp1m1j mice. Early mortality prevents the evaluation of Tpp1m1j control animals at later time-points, and data appeared to be highly variable in these assays despite clearly impaired function upon clinical observations (eg, pronounced gait abnormalities and tremor). The rapid progression from disease onset to early mortality, as well as the potential for environmental stimuli-induced fatal seizures during animal handling, pose additional challenges.

Overall, there were no differences in survival between Tpp1m1j control and low-dose animals, while all high-dose animals survived beyond the expected median survival of Tpp1m1j mice based on natural history data. At 30 weeks post-injection, survival in the high-dose group was 85% (10/10 males; 7/10 females) versus 0% in the low-dose and Tpp1m1j control groups (FIG. 4A). All surviving animals were necropsied at 30 weeks post-injection for histopathology.

Figure 19:
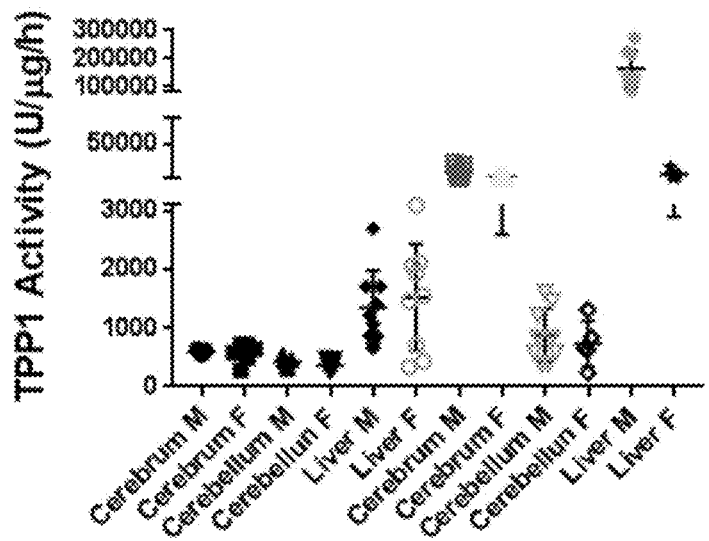
FIGS. 19 and 20 demonstrate TPP1 enzymatic activity in the brain and liver at 30 weeks post-injection (34 weeks of age) in surviving animals
Figure 21A:
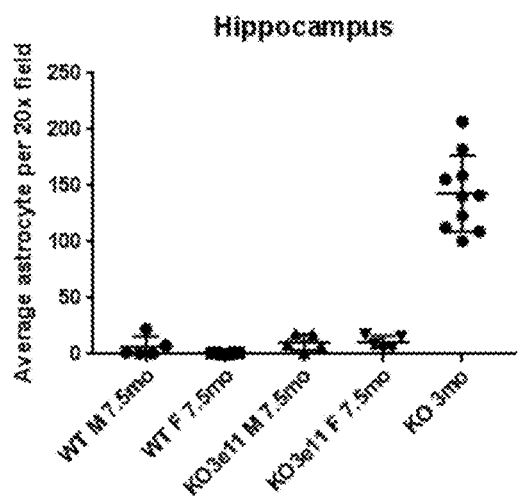
FIGS. 21A to 21C demonstrate correction of astrocytosis in the brain of high-dose and Tpp1m1J mice (30 weeks post-injection; labeled 7.5 mo) and control animals (15 weeks of age; labeled 3 mo). TPP1 KO mice were injected with PBS only or $3\times10^{11}$ GC of AAV.hTPP1co as well as wildtype mice injected with PBS only as described in Example 5. GFAP scores was established in three different parts of the brain (hippocampus—FIG. 21A; cortex—FIG. 21B; brainstem—FIG. 21C) of animals in the high-dose group and compared to GFAP scores in 15-week old Tpp1m1j control mice from the natural history study, as no vehicle control animals were alive at the end of the study. Data presented as average number of astrocytes per ×20 power field. P-value by unpaired Mann Whitney test.
Figure 21B:
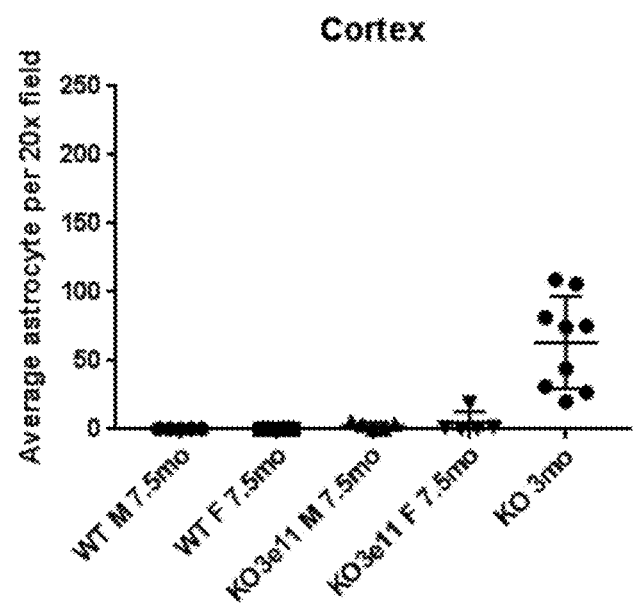
Figure 21C:
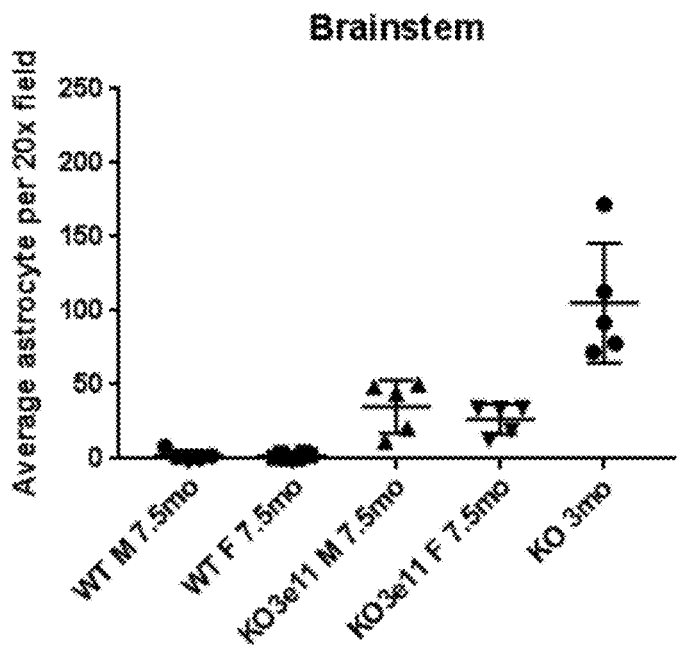

All surviving animals at 30 weeks post-injection were euthanized (ie, high-dose and WT control groups only; no animals survived from the Tpp1m1j control or low-dose groups), and tissues were harvested for evaluation of TPP1 enzymatic activity, inflammation (astrocytosis), and accumulation of substrates in the lysosomes. Collectively, data provide additional evidence of the bioactivity of AAV9.CB7.hCLN2, including: i) increases in TPP1 enzymatic activity to wild type levels in the serum (data not shown) and supraphysiological levels in the cerebrum, cerebellum, and liver (FIGS. 19 and 20); ii) near complete correction of astrocytosis in several parts of the brain, most markedly in the hippocampus (FIG. 21A) and cortex (FIG. 21B) (FIG. 21C shows brainstem); and iii) qualitative correction of the abnormal lysosomal storage phenotype in neurons as shown via three different techniques (data not shown Lysosomal storage in brainstem neurons can be visualized using three different techniques: auto-fluorescence, H&E and Periodic acid-Schiff (PAS) staining. Representative images from wild type control mice and Tpp1m1j mice administered the high-dose of AAV9-hCLN2 at 30 weeks post-injection were obtained (not shown). Representative images from Tpp1m1j control mice (denoted as 'KO') at 5.5-months of age were obtained (not shown). These three different techniques show a similar pattern of lysosomal accumulation. Abnormal storage accumulates in neurons of Tpp1m1j control mice and appears to be corrected in high-dose animals. While these techniques are qualitative only, the reduction of lysosomal storage in large neurons of the brainstem of high-dose animals at weeks post-injection was readily detected. Biodistribution to the liver was observed (data not shown), with levels of cell transduction appearing to correlate with TPP1 enzymatic activity in both the liver and serum. No other tissues were evaluated for biodistribution in this pilot study.

Humoral immune responses to the human TPP1 transgene product were assessed in serum using ELISA at 3, 10 and 30 weeks post-injection of AAV9.CB7.hCLN2 in Tpp1m1j mice. Data indicated a sustained immune response, although levels appeared highly variable-humoral immune responses to the human TPP1 transgene product appeared highest in low-dose males at weeks post-injection, with only a minimal response observed in high-dose males at both 10 and 30 weeks post-injection; within the high-dose group, anti-TPP1 immune responses were also higher in females than males at both 10 and 30 weeks post-injection. These pilot data may be suggestive of potential gender-specific differences in AAV9.CB7.hCLN2 biodistribution and transgene expression in mice or subsequent partial tolerance. There is some evidence that liver transduction efficiency of AAV vector-based products in mice may be testosterone-dependent (Davidoff, 2003), although it is likely that variable data in this pilot study are more illustrative of the challenges to the evaluation of immune responses to human proteins in animals (and challenges in their interpretability and applicability to the human clinical scenario), than any gender specific-differences in the biodistribution profile or immunogenicity of AAV9.CB7.hCLN2. Nonetheless, any potential gender-specific differences, specifically any effect on bioactivity or immunogenicity, will be evaluated further in the planned IND-enabling Hybrid Pharmacology/Toxicology study.

Example 12: Comparability of Intracerebroventricular (ICV) and Intracisternal (IC) Routes of Administration In pilot studies conducted in the Tpp1m1j mouse model, AAV9.CB7.hCLN2 was administered via ICV injection. This route of administration is different than the planned clinical IC route of administration, however IC injections are not feasible in Tpp1m1j mice. During IC injection procedures, it is necessary to withdraw a small volume of CSF to decrease pressure in the CSF compartment and confirm correct needle placement in the cisterna magna. Due to the relatively small CSF volume in mice, correct needle placement cannot be confirmed by withdrawing CSF. Thus, it is necessary to dissect fascia and muscle to expose the dura mater prior to injection. This surgical procedure is time-consuming and presents the risk of procedure-induced motor impairment and/or pathology in mice.

Considering that IC injections are not feasible in Tpp1m1j mice, the ICV route of administration was selected for pharmacology/toxicology studies due to similarities of the biodistribution and transgene expression profiles of AAV9 vector-based products following IC injection in large animals and ICV administration in mice.

In the preclinical testing program for a similar AAV9 vector-based product, the biodistribution profile (target tissues/organs) was shown to be comparable following either ICV injection in mice and IC injection in NHPs. Similarly, in a study published by Haurigot et al., (2013), AAV9 vector biodistribution and GFP mRNA expression were compared in canines following CSF delivery of $2\times10^{13}$ vg/animal of AAV9.GFP vectors through either IC (n=1) or ICV (n=2) injection. Side-by-side analyses of AAV9 vector biodistribution and transgene expression profiles in the CNS and somatic organs were not suggestive of major differences in the vector transduction profile with either route of delivery.

Thus, pharmacology/toxicology data generated in Tpp1m1j mice following ICV injection of AAV9.CB7.hCLN2 are relevant to the clinical scenario and planned IC route of administration in the target patient population.

Example 13: Planned Hybrid Pharmacology/Toxicology Study in Tpp1m1j Mouse Model of CLN2 Disease The proposed preclinical testing program for AAV9.CB7.hCLN2 includes an IND-enabling Hybrid Pharmacology/Toxicology study conducted in the Tpp1m1j mouse model of CLN2 disease. In general, hybrid study designs facilitate the evaluation of the safety and bioactivity of a test article in a disease setting that reproduces the local microenvironment and pathophysiology status of the target patient population, which may impact the safety and bioactivity of the product in the clinical setting. As a result, data generated in hybrid studies are oftentimes more relevant than data obtained from studies conducted in healthy animals. Thus, data generated from the proposed Hybrid Pharmacology/Toxicology study will help to inform the selection of a safe and efficacious initial clinical dose level.

In the proposed study, AAV9.CB7.hCLN2 will be administered via ICV injection in 4-week old mice at a dose level range of $2\times10^{10}$ GC/g brain mass to the MFD of $7.5\times10^{11}$ GC/g brain mass. Half of the animals will be sacrificed at 60 days post-injection to coincide with expected neuropathology and mortality in control animals and evaluated for bioactivity, including TPP1 enzymatic activity, accumulation of lysosomal storage material and storage pathology, and astrocytosis. The remainder of the animals will be evaluated for the time to onset of disease phenotype (defined by seizure, tremor and/or gait abnormality upon clinical observations) and followed for long-term survival for up to 210 days post-injection, which is beyond when 100% mortality is expected in control animals. All mice will be evaluated for limited assessments of safety at multiple time points, as feasible.

While data from pilot studies were suggestive of an effect of AAV9.CB7.hCLN2 on the prevention of cerebellum functional decline in Tpp1m1j mice, the utility of these neurobehavioral assays was limited and data on long-term survival is considered a more objective measure of bioactivity. Thus, the neurobehavioral assays used in pilot studies were not incorporated into the design of this study. Specifically, early mortality prevented the evaluation of Tpp1m1j control mice at later time points, and data from pilot studies appeared to be highly variable despite clearly impaired function upon clinical observations (eg, pronounced gait abnormalities and tremor). The rapid progression from disease onset to early mortality, as well as the potential for environmental stimuli-induced fatal seizures during animal handling, pose additional challenges for conducting these assessments in Tpp1m1j mice.

It is not feasible to collect all proposed measurements of safety and bioactivity in all groups due to limited tissue availability and susceptibility of Tpp1m1j mice to environmental stimuli-induced fatal startle seizures (which may limit the ability to perform in-life safety assessments that require animal handling, such as serial bleeds). Thus, assessments of bioactivity will be prioritized in Groups 1-6, and assessments of safety/toxicology will be prioritized in Groups 7-9.

Key design elements for the proposed study, and a discussion of their scientific rationale, is provided below:

1) Animal model of disease: The Tpp1m1j mouse model is a biologically-relevant murine model of CLN2 disease.
2) Test article: The intended clinical product and formulation (buffer/diluent) will be evaluated.
3) Dose level range: Multiple dose levels in a range from $2\times10^{10}$ GC/g brain mass to $7.5\times10^{11}$ GC/g brain mass will be evaluated to identify the minimum effective dose (MED) and no-observed-adverse-effect-level (NOAEL). In pilot studies, there did not appear to be benefit in survival or other measures of bioactivity in Tpp1m1j mice that were administered AAV9.CB7.hCLN2 at dose level of $7.5\times10^{9}$ GC/g brain mass. The MFD in Tpp1m1j mice utilizing the ICV route of administration (ROA) is $7.5 \times 10^{11}$ GC/g brain mass.
4) Intracerebroventricular (ICV) route of administration (ROA): Please see Section 3.4.2.5 for a detailed description of the similarities between the IC and ICV routes, which supports the applicability of the ICV route in mice to the planned clinical scenario. The acute safety of IC injection procedures was previously established in NHP studies conducted under IND #17565.
5) Scheduled sacrifices and study duration: The scheduled sacrifices at 60 and 90 days post-injection were selected to coincide with the onset of the disease phenotype in the Tpp1m1j mouse model (disease onset is characterized by onset of gait abnormalities, tremors, seizures, and sudden death) and expected neuropathology and early mortality, respectively. Based on natural history data, it is not expected that any Tpp1m1j control mice will survive until the final scheduled sacrifice at 210 days post-injection.
6) Pharmacology/bioactivity endpoints: The quantitative endpoints to evaluate bioactivity will include: time to onset of disease phenotype (defined as gait abnormality and/or tremor upon clinical observations, astrocytosis correction at 60 days post-injection, body weight changes (measured weekly), TPP1 enzymatic activity in brain tissue at 60 days post-injection, and survival through 210 days post-injection. At necropsy (day 60 post-injection), qualitative histology of lysosomal storage correction and TPP1 enzymatic activity in the cerebrum, cerebellum, liver, and serum will provide additional measures of bioactivity. Data from pilot studies indicated that neurobehavioral measurements (rotarod-based assays) are of limited utility in the Tpp1m1j mouse model; thus, these assessments have not been incorporated into the design of this study.
7) Safety/Toxicity endpoints: Control mice and Tpp1m1j mice administered AAV9.CB7.hCLN2 via ICV injection at the highest dose level (MFD) will be evaluated for safety and immunogenicity at multiple time points, as follows:
    Clinical observations (cage-side morbidity and mortality examinations, daily)
    Detailed clinical observations (weekly)
    Body weight (weekly)
    Complete clinical pathology (d30, d90)
    Immunogenicity (anti-TPP1 antibodies in serum, ELISA) (baseline, d14, d60, d210)
    Organ weights (d60, d90)
    Gross pathology and histopathology of a comprehensive list of tissues and any tissues showing macroscopic abnormalities (d60, d90)
8) Immunogenicity assessments: Humoral immune responses (serum antibodies against hTPP1) will be evaluated at baseline and 14, 60, and 210 days post-injection. Humoral immune response to transgene products in mice have been shown to correlate to the responses observed in NHPs (data not shown). However, cellular immune responses (ie, interferon gamma T cell ELISPOT assays) are not as informative in mice as it is not technically feasible to isolate adequate PBMC from whole blood to run the assay. For this reason, ELISPOT assays in mice would need to be performed with splenocytes, however data from the previous studies that included evaluation of T cell responses in splenocytes isolated from NHPs did not correlate with data obtained in PBMC from the same NHPs. Thus, evaluation of T-cell immune response are not incorporated into the study design.
9) Unscheduled deaths: Necropsy and other assessments, as appropriate, will be performed on all unscheduled deaths in an attempt to determine the cause of death.

Example 14: Safety/Toxicology and Biodistribution

Potential GLP Safety/Toxicology Study in C57Bl/6 Mice

The proposed preclinical testing program for AAV9.CB7.hCLN2 includes a Hybrid Pharmacology/Toxicology study conducted in the Tpp1m1j mouse model of CLN2 disease. Mice administered AAV9.CB7.hCLN2 via ICV injection at multiple dose levels up to the MFD will be evaluated for safety at multiple in-life timepoints and scheduled sacrifices, as follows:
    Clinical observations (cage-side, daily)
    Body weight (weekly)
    Clinical pathology (d60, d90, d210)
    Humoral immune response in serum (anti-hTPP1 antibodies in serum, ELISA) (baseline, d14, d60, d210)
    Organ weights (d60, d90, d210)
    Gross pathology and histopathology of a comprehensive list of tissues (d60, d90, d210) on any surviving animals (100% mortality is expected in control animals by 6-months of age).

In general, hybrid study designs facilitate the evaluation of the safety of a test article in a disease setting that reproduces the local microenvironment and pathophysiology status of the target patient population, which may impact the safety and bioactivity of the product in the clinical setting. Thus, safety/toxicology data generated from the proposed Hybrid Pharmacology/Toxicology study are anticipated to provide important information regarding the safety profile of AAV9.CB7.hCLN2. As per Agency guidance recommendations, "The animal species selected for assessment of bioactivity and safety should demonstrate a biological response to the investigational [product] similar to that expected in humans in order to generate data to guide clinical trial design." Therefore, the selection of the Tpp1m1j mouse model of CLN2 disease is appropriate for the evaluation of the safety of AAV9.CB7.hCLN2.

There are some potential challenges of assessing safety in Tpp1m1j mice, including the concern that the underlying pathology and early mortality in the disease Tpp1m1j mice may mask potential test article-related effects and that the ability to perform some safety assessments (such as serial bleeds) may be limited due to the susceptibility of Tpp1m1j mice to environmental stimuli-induced fatal seizures. If these concerns are borne out by experience, and the Tpp1m1j mouse safety data are not considered sufficient to satisfy regulatory requirements, an additional GLP-compliant toxicology study will be conducted in C57Bl/6 mice. C57Bl/6 mice are considered appropriate for detecting potential toxicities associated with AAV9.CB7.hCLN2 because: i) the C57Bl/6 mouse is the background strain for the Tpp1m1j mouse model used in pharmacology assessments; ii) the comparability of biodistribution and transgene expression profiles of AAV9 vector-based products following ICV injection in mice and IC injection in large animals has been established; iii) the feasibility of performing safety assessments in healthy mice is not limited by animal handling concerns or susceptibility to environmental stimuli-induced fatal seizures, such as in the Tpp1m1j mouse; and iv) the conduct of GLP-compliant safety/toxicology studies in healthy mice is feasible, well-established, and statistically-robust. The selection of rats as an alternative species is potentially appropriate and would theoretically enable the incorporation of the planned clinical IC ROA (which is not feasible in mice), however this species has not been sufficiently characterized (eg, biodistribution profile of AAV9 vector-based product following delivery into the CSF) to support its use in the preclinical testing program for AAV9.CB7.hCLN2.

In this potential GLP Safety/Toxicology study, AAV9.CB7.hCLN2 will be administered at a dose level of 7.5×1010, 2×1011 and the MFD of 7.5×1011 GC/g brain mass via ICV injection in 4-week old C57Bl/6 mice, and mice will be evaluated for safety/toxicity at multiple time points. The planned scheduled sacrifices (30 and 90 days post-injection) and study duration (90 days post-injection) were selected to coincide with the kinetics of AAV9 vector biodistribution and progression of the disease phenotype in Tpp1m1j mice. Safety assessments will include clinical observations, body weight, clinical pathology, immunogenicity, gross pathology, and histopathology of a comprehensive list of tissues. The safety of the proposed IC ROA has previously been established in studies conducted in NHPs under IND #17565.

Scientific Rationale and Safety of the Administration of AAV9.CB7.hCLN2 Via Intracisternal Injection Intracisternal (IC) injection was selected as the route of administration (ROA) for AAV9.CB7.hCLN2 to allow direct and non-invasive delivery of the vector to the target CNS tissue within the confined CSF compartment (Hinderer et al., 2014b; Hinderer et al., 2017; IND #17565). While intravenous delivery of AAV9 vector-based products has also been shown to target cells within the CNS, delivery into the CSF has been shown to achieve more efficient transduction in the brain at lower vector dose levels and with less transduction of peripheral organs (Nathwani et al., 2011; Gray et al., 2013; Hinderer et al., 2014; Hinderer et al., 2014b).

The definitive safety assessment of IC injection via image-guided suboccipital puncture into the cisterna magna (ie, planned clinical ROA) was previously evaluated in GLP-compliant NHP studies conducted as part of the preclinical testing programs for similar AAV9 vector-based products. Briefly, the administration procedure was well-tolerated in all animals across multiple studies; there were no clinical, gross, or histological findings related to the administration procedure in any animal at 14, 30, or 90 days post-IC injection. Complete preclinical study reports (and available clinical data) will be provided at the time of IND submission.

Existing Biodistribution Data for AAV9 Vector-Based Products Following IC Injection The likely biodistribution profile of AAV9.CB7.hCLN2 following IC injection in the target patient population is informed by pre-existing biodistribution data generated for similar AAV9 vector-based products. For example, the biodistribution of similar AAV9 vector-based products have been comprehensively characterized in multiple species, including cats, dogs, and NHPs for up to two years following IC injection, and the definitive assessments of biodistribution were conducted in GLP-compliant NHP studies designed with the input of FDA/CBER/OTAT (PTS #P5002653 and PTS #P5002919). To summarize, these products were shown to widely distribute and persist in the brain and spinal cord after IC injection in a variety of animal species. Where multiple dose levels were evaluated, vector tissue levels were roughly dose-dependent. Vector distribution to the liver and spleen were generally as high, and sometimes higher, than that observed in the brain; limited data suggests that preexisting titers to AAV9 may reduce peripheral tissue vector expression, though there was no observable effect on CNS expression. Vector concentrations in tissues other than the CNS and liver were highly variable both within studies and between studies, but all tissues evaluated contained vector. Furthermore, vector expression did not change meaningfully for up to 6-months following administration in the definitive assessment of the biodistribution in NHPs.

Overall, biodistribution profiles (target tissues/organs and kinetics of biodistribution) for AAV9 vector-based products have been shown to be consistent across multiple species and studies.

Example 15: Clinical Trial

Overview of Clinical Development Program and Planned Pivotal Clinical Trial

The proposed clinical development program for AAV9.CB7.hCLN2 includes a single trial conducted in two parts (FIG. 26; FIG. 27). A detailed synopsis is provided in Section 4.

In Part I of the trial, the primary focus will be on safety and tolerability and up to two dose levels are planned as part of a conservative dose escalation design—subjects who are ≥2 years of age with a baseline CRS (combined motor and language domains) score of 3-5 during treatment with IT ERT (Brineura®) will be enrolled sequentially, a minimum of 8-weeks apart, with ongoing ISC review. Two subjects will be dosed at the first dose level and an external IDMC will determine if it is safe to proceed to dosing two subjects at a higher dose level after an evaluation of safety.

In Part II of the study, the highest-tolerated dose cohort may be expanded up to a total of subjects and will include a patient population of both IT ERT-treated and IT ERT naïve subjects. Inclusion/exclusion criteria will otherwise remain the same in this expanded population, including a score of 3-5 on the CLN2 Disease CRS.

In Part I of the trial, the focus will be on safety and tolerability, although efficacy parameters will be measured. In the first dosing cohort, two eligible subjects on IT ERT will be enrolled sequentially at a minimum of 8 weeks apart to receive the lower dose, which is expected to be an efficacious dose. Each subject will undergo screening (Day −35 to Day −1) and if eligible will receive a single IC dose of AAV9.CB7.hCLN2 on Day 1 and will remain in the hospital for approximately 30 to 36 hours after dosing for observation. The subject will continue to receive IT ERT every 2 weeks during screening and up to 8 weeks post-administration of AAV9.CB7.hCLN2. Trough levels of CSF TPP1 activity will be measured just prior to the IT ERT infusion. Trough TPP1 activity are expected to be undetectable from the infusions while TPP1 activity from the gene therapy would be expected to be measurable from 1 to 4 weeks post administration. Once trough TPP1 activity is measurable and if pre-specified criteria are met, then the ISC could decide to stop IT ERT infusions if certain pre-specified criteria are met. Subjects would at a minimum receive IT ERT at 2 and 4 weeks post AAV9.CB7.hCLN2 and will have been off IT ERT for up to 4 weeks prior to the Week 8 visit. The ISC will review the safety data obtained during the first 8 weeks (including data obtained during the Week 8 visit) for this subject, and if there are no safety concerns, the next subject may be enrolled. The second subject would undergo the same process in determining when to discontinue IT ERT. If no Safety Review Triggers (SRTs) are observed (Table 35), all safety data obtained up to and including the Week 8 visit for the 2nd subject will be evaluated by the IDMC. If any event meets the criteria of a Stopping Rule, dosing of any new subjects will be suspended until a complete review of all safety data has been performed. At any given IDMC meeting, whether planned at the conclusion of a dose cohort or called for by an SRT, the IDMC may recommend to stop the trial, dose additional subjects at the current dose, proceed to the next dose cohort, or proceed at a lower dose. In real time, the safety and tolerability of each dosed subject will be assessed as follows:

TABLE 35

Safety Review Triggers and Actions

| Safety Review Trigger Event | Safety Review Action |
|---|---|
| A Stopping Rule is met (defined below) | An external IDMC will review all available safety data and provide a recommendation on whether to enroll additional subjects. |
| Any Grade 4 or 5 adverse event (AE), regardless of relationship to treatment | An Internal Safety Committee will review all available safety data. If safety concerns arise while a cohort is enrolling, they may ask the IDMC to review and make a recommendation on whether to keep enrolling subjects in that cohort. |
| Any Grade 3 AE considered treatment related (by the principal investigator) | |
| Any Grade 3 AE considered unrelated to treatment (by the principal investigator) | |
| Any report by the principal investigator of technical issues with the AAV9.CB7.hCLN2 administration procedure that may warrant modifications to the procedure or instruments | |
| 2   Recognizably abnormal. | |
| 1   Hardly understandable. | |
| 0   Unintelligible or no language. | |

If the decision is to proceed to the second dosing cohort, the subsequent 2 eligible subjects on IT ERT in Part I will follow the same dosing scheme as the initial dose cohort with dosing of each subsequent patient occurring after all safety data obtained during the first 8 weeks (including data obtained during the Week 8 visit) for the previous subject have been reviewed. If no SRTs are observed, all safety data obtained up to and including the Week 8 visit for the 2nd subject will be evaluated by the IDMC.

If the IDMC determines that it is safe to proceed into Part II of the trial, then approximately 13 additional subjects who either are receiving IT ERT or are naïve to IT ERT, will be enrolled in a competitive and parallel manner. There would be a planned biannual IDMC meeting but the ISC could decide to call for an IDMC meeting at any time, which could also involve halting enrollment.

Those subjects currently on IT ERT will be asked to discontinue ERT approximately 4-6 weeks after AAV9.CB7.hCLN2 therapy when appropriate pre-specified criteria have been met (eg, stable CRS, evidence of CSF TPP1 activity from the gene therapy, and other criteria are being considered). The CRS (Motor and Language domains) will be measured every 8 weeks or more frequently if changes are observed. Specific guidelines for restarting IT ERT will be prospectively defined at protocol development and will likely be based on changes in the CRS scores and the investigators' own clinical evaluation and judgement. In reference to the latter, different clinical situations (eg, illness, seizure frequency) in proximity to the CRS measurement could impact the score and not be reflective of disease progression; thus, therapeutic interventions (eg, change in seizure medication) and additional testing may be performed to assess the reversibility in CRS scores.

Since application of vector into the IC space has not been previously conducted in humans, risks for this procedure have not yet been determined. The procedure was originally described in 1919 when it was performed without any imaging. A case series of 43 procedures in subjects reported no serious complications and concluded that the technique should prove safe in the hands of a careful operator (Ayer et al., 1920). There are potentially serious complications from a suboccipital puncture which represents more than minimal risk. However, the protocol proposes a thorough mitigation strategy to minimize these risks. Patients who may be at higher risk for complications based on their medical and surgical history or anatomic abnormalities present on MRI are excluded from the study. Furthermore, the MRI images obtained during the screening period are reviewed by a group of neuroradiologists/neurosurgeons at the participating centers and a consensus will be required to proceed with the procedure which is done under CT guidance to further minimize the risks. A training program is also required for physicians that will be performing this procedure in the planned clinical trial. Overall, the expectation is that the risks we may see will be much like those seen with lumbar puncture, including headache and injection site reactions.

The clinical safety and efficacy of AAV serotypes loaded with a therapeutic transgene has been demonstrated in the EMEA-approved gene therapy GLYBERA® (alipogene tiparvovec; GLYBERA SmPC, 2016) indicated for lipoprotein lipase deficiency. Clinical trial experience with AAV vectors for inherited forms of blindness (MacLaren et al., 2014; Maguire et al., 2008), hemophilia B (Nathwani et al., 2014), and many other disease indications (Luo et al., 2015) provides additional support for the safety and potential efficacy of AAV gene therapy. There are several ongoing gene therapy studies utilizing AAV, including AAV9. However, direct clinical data addressing long-term risks of AAV-mediated gene transfer are limited, and the long-term risks remain unknown.

IS therapy will be implemented in the present study and will include corticosteroids (methylprednisolone 10 mg/kg intravenously [IV] once on Day 1 predose and oral prednisone starting at 0.5 mg/kg/day on Day 2 with gradual tapering and discontinuation by Week 12), tacrolimus (0.5 mg/kg twice daily [BID] by mouth [PO] Day 2 to Week 24 with target blood level of 2-4 ng/mL and tapering over 8 weeks between Week 24 and 32), and sirolimus (a loading dose of 1 mg/m2 every 4 hours×3 doses on Day −2 and then from Day −1: sirolimus 0.5 mg/m2/day divided in BID dosing with target blood level of 1-3 ng/ml until Week 48).

Immunosuppression has been included in other CNS-directed AAV gene therapy studies to minimize the impact of an immune response against AAV and/or the transgene on both safety and efficacy and appears to be safe and well-tolerated. Two companies, Lysogene (developing an AAVrh.10 vector-based product) and uniQure (developing an AAV5 vector-based product), conducted clinical trials in patients with Sanfilippo syndrome (MPS III), utilizing an IS regimen of prednisolone, MMF, and the calcineurin inhibitor, tacrolimus. Lysogene reported that safety data over 3 years following gene therapy showed good tolerability, absence of adverse events (AEs) related to the injected product, and no biological sign of toxicity related to immunosuppressive drugs (Tardieu et al., 2017). Similarly, uniQure reported no local inflammation or other safety concerns related to the investigational therapy or the procedure over 1 year following gene therapy (UniQure, 2015).

In an ongoing AAV9-mediated IT gene transfer study, GAN patients with at least 1 missense mutation in the GAN gene received IS with corticosteroids only, while 1 patient with a null mutation received IS with corticosteroids, tacrolimus, and sirolimus to minimize a potential higher risk for an adaptive anti-transgene response (Bharucha-Goebel et al., 2017). So far, the therapy has been reported to be clinically well-tolerated and the observed rises in both CSF and peripheral AAV9 NAB titer and CSF pleocytosis do not appear to impact clinical safety.

In the proposed study, an IS regimen is considered relevant to use and is being planned for the following reasons:

To prevent or minimize a potential exaggerated immune response against TPP1, especially in patients with gene mutations that may result in complete absence of the gene product. Such an immune response may increase the risk of a hypersensitivity reaction or an immune mediated reaction against tissues expressing the transgene.

To prevent the formation of NAbs against TPP1 or an increase in NAbs against TPP1 (in patients on ERT who likely have pre-existing NAbs), which may potentially reduce the bioactivity of AAV9.CB7.hCLN2 and/or IT ERT.

Corticosteroids are prudent to reduce the immediate degree of inflammation that may be seen early after AAV treatment and thus minimize the ability of an inflammatory response that can cause tissue damage as well as to prime a T- and B-cell-mediated adaptive immune response. Tacrolimus is a calcineurin inhibitor, which blocks very early steps in T-cell activation, leading to impaired cytokine production and blockade of T-cell expansion and differentiation into effector cells. It is routinely used as part of a post-transplant regimen with steroids and MMF primarily in liver and kidney transplantations (Scalea et al., 2016). Tacrolimus is an effective drug available to prevent a T-cell-mediated immune response against exogenous antigens such as the transgene. As T-cell help is also required for B-cell antibody production to the transgene, this agent can be expected to be effective at blocking both cell-mediated and humoral immunity.

Sirolimus (RAPAMUNE® USPI, 2017), also known as rapamycin, acts via a mechanism distinct from that of calcineurin inhibitors; it inhibits the ability of cytokines to promote T-cell expansion and maturation by blocking intracellular signaling and metabolic pathways. However, its net effect is to target many of the same cellular processes. It is also commonly used in post-transplant IS (Zhao et al., 2016). In addition, nonclinical and clinical studies suggest that sirolimus may provide relative sparing of the regulatory T lymphocytes (Treg), which could allow withdrawal of the drug without rebound immune reactions (Hendrix et al., 2009; Ma et al., 2009; Mingozzi et al., 2007; Singh et al., 2014). There is precedent in both the gene therapy literature and the solid organ transplantation clinical trials for patients to be initially treated with tacrolimus and then have successful "conversion" to rapamycin, with excellent sustainment of immunosuppressive efficacy (El-Agroudy et al., 2017).

The duration of therapy for the various immunosuppressive agents is based partially on their successful use in human transplantations and on the designs utilized for MPS III or GAN gene therapy studies. Subjects will be monitored closely by laboratory and clinical examinations for any AEs during the study especially at times when IS reduced or discontinued.

The following endpoints are proposed:

Safety Assessments:
  Safety post-AAV9.CB7.hCLN2 dosing: AEs, SAEs, laboratory evaluations, vital signs, ECGs, EEG, physical examinations, vision, developmental milestones, and neurologic assessments
  Immunogenicity measurements
  Neutralizing antibodies to AAV9 and binding antibodies to TPP1 in CSF and plasma
  Enzyme-linked immunospot (ELISPOT) assay: T-cell response to AAV9 and TPP1
  Viral shedding: Vector concentration in CSF, serum, and urine Efficacy Assessments:
  TPP1 activity in plasma and CSF
  Proportion of subjects without an unreversed (sustained) 2 category decline (ie, 1 in each of Language and Motor domains or 2 in Motor domain alone) in the 6-point combined Language and Motor domains of the CRS and without a rescue medication through 72 weeks for IT ERT naïve subjects and 80 weeks for IT ERT-treated subjects post AAV9.CB7.hCLN2 as compared to a natural history cohort
  Proportion of subjects without an unreversed (sustained) 2 category decline (ie, 1 in each of Language and Motor domains or 2 in Motor domain alone) in the 6-point combined Language and Motor domains of the CRS and without a rescue medication through 96 (IT ERT naïve)/104 (IT ERT-treated) weeks post AAV9.CB7.hCLN2 as compared to a natural history cohort
  Mean rate of decline in the 6-point combined Language and Motor domains of the CRS through 72 (IT ERT naïve)/80 (IT ERT-treated), and 96 (IT ERT naïve)/104 (IT ERT-treated) weeks post AAV9.CB7.hCLN2 as compared to a natural history cohort and change from baseline
  Mean rate of decline in combined and individual component (Motor, Language, Vision, Seizure domains) scores of CRS through 72 (IT ERT naïve)/80 (IT ERT-treated), and 96 (IT ERT naïve)/104 (IT ERT-treated) weeks post AAV9.CB7.hCLN2 dosing as compared to a natural history cohort and change from baseline
  Time to unreversed 2-category decline in the 6-point combined Motor and or Language domain of the CRS
  Validated instrument for intelligence quotient (IQ) (Wechsler Abbreviated Scale of Intelligence [WASI-II])
  Parent reporting from Vineland Adaptive Behavior Scales, Second Edition (VABS-II)
  Volumetric analysis of gray and white matter and CSF ventricles by MRI.
  Retinal thickness by SD-OCT
  QOL measurements: Pediatric Quality of Life Inventory (PedsQL) Generic Core Scales and CLN-2 Specific supplement; Infant Toddler Quality of Life Questionnaire™ (ITQOL)

In the proposed clinical trial, multiple measures of efficacy will be evaluated including TPP1 enzymatic activity in the CSF and the proportion of subjects who are categorized as responders which is defined as subjects: i) without an unreversed (sustained) 2 category decline (ie, 1 in each of Language and Motor Domains or 2 in Motor Domain alone)

in the 6-point combined Language and Motor Domains of the CLN2 Disease CRS (Steinfeld et al., 2002); and ii) without a "rescue" IT ERT infusion. Two sets of patient populations (ie, IT ERT naïve and IT ERT-treated) are planned in the Part II expansion cohort, where IT ERT naïve subjects will be followed for 72 weeks and IT ERT-treated subjects will be followed for 80 weeks, and the combined two patient populations will be compared to a natural history cohort. The primary reason to combine these two populations is to facilitate trial enrollment due to the rarity of CLN2 disease in general and the further reduction of IT ERT naïve patients following the recent approval of Brineura®. Due to the potential impact of any residual ERT in IT ERT-treated patients and potentially confounding effects on assessment of AAV9.CB7.hCLN2, a "wash-out" period is incorporated into the study design. PK data for Brineura® in CSF and plasma suggest no apparent accumulation or PK time-dependence with a half-life of approximately 7 hours and 11.5 days in CSF and lysosomes, respectively (Brineura® EPAR), thus the proposed "wash-out" period of up to 4 weeks following discontinuation of IT ERT is appropriate. An analysis will be conducted using a responder analysis by comparing combined IT ERT naïve and IT ERT-treated subjects in AAV9.CB7.hCLN2 high dose group to the closest 1-1 matched subjects in the external natural history control group. The McNemar's Exact test will be performed to analyze the matched population. The 1-1 matched subjects from the natural history control group are selected based on baseline CLN2 score, age ±6 months, and common genotype. When more than one match occurs, the selection will be narrowed further by matching on additional criteria in the following order (1) detailed genotype and (2) sex. This analysis will be performed at 72 weeks for IT ERT naïve subjects and 80 weeks for IT ERT-treated subjects. The baseline CRS (combined motor and language domains) score will be pre AAV9.CB7.hCLN2 injection for AAV9.CB7.hCLN2 group. The data through Week 72 for the matched subjects in the natural history control group will be used for the analysis.

The approval of Brineura® in the US was based on the primary efficacy endpoint of the proportion of subjects with an absence of an unreversed (sustained) 2-category (raw) decline or an unreversed score of 0 in the Motor domain of the CLN2 Disease CRS over a 96-week period. The originally proposed primary efficacy endpoint by BioMarin Pharmaceuticals was the proportion of patients with an absence of an unreversed (sustained) 2-point rate (slope) of decline or a score of 0 in the Motor-Language total score over 48 weeks. The agency disagreed with using the Motor-Language total score and recommended the use of the Motor domain only. The time point for the primary efficacy analysis was also modified from Week 48 to Week 96 after no substantial evidence of efficacy was found at Weeks 48 and 72. In contrast, Brineura® was approved by the EMA based on proportion of subjects who did not have a 2-point decline on the combined Motor and Language Domains of the CLN2 Disease CRS during a 48-week study period, as compared to historical natural history data. Several sensitivity and supportive analyses also confirmed these results.

The agency raised some concerns over the comparability of the CLN2 Disease CRS used across the different studies in the Brineura® marketing application (Brineura®, FDA Summary Basis of Approval). The first key issues identified in the Clinical Outcome Assessment Review was the concern that the potential difference in descriptors used may not lend itself to a clear understanding of what a particular score means clinically, especially in the cited examples of the qualitative descriptors around a score of '2'. The second issue identified by the Agency was around both: i) the different methods of rating, where subjects in the natural history study were rated by clinicians both retrospectively and prospectively through live assessment and secondary sources (eg, medical charts, parental interviews, etc.), while subjects in the Brineura® pivotal study were rated by clinicians prospectively through live assessment only; and ii) the different schedules of assessments, where the CLN2 CRS scale was assessed approximately every 12 weeks and 8 weeks in the natural history study and the Brineura® pivotal study, respectively. We understand from the Agency's review that the findings from the Video Comparability study also did not support the use of the language item in the CLN2 Motor-Language total score as there was disagreement of ratings on the CLN2 scales used in the natural history study and the Brineura® pivotal study. It was observed that there was greater discordance with the language item.

The assessment of language skills and development is critical in the CLN2 disease patient population and thus is incorporated into the CRS in the planned clinical trial of AAV9.CB7.hCLN2. To address potential concerns regarding the utility of including the Language Domain (which were identified by FDA/CDER during review of Brineura® marketing application [Brineura®, FDA Summary Basis of Approval]), a mitigation plan will be implemented to remove potential biases using this tool, specifically:

The original descriptive text of the Language Domain ratings, as used in the natural history study, will be used so that consistent Language Domain ratings can facilitate the interpretation and direct comparison of the Motor-Language total score within each study and between studies.

Evaluations will incorporate multiple random reviews of video assessments by multiple independent blinded examiners, where only one of multiple reviews for each subject is completed in the correct/real chronological order (the other reviews would be performed on a randomly permuted ordering of the video assessments (and discarded)). In this way, longitudinal and intra-individual scoring are performed by the same examiner without introducing any potential biases.

Sample size calculations have been performed using McNemar's exact test for the proportion of subjects without an unreversed (sustained) 2 category decline (ie, 1 in each of Language and Motor domains or 2 in Motor domain alone) in the 6-point combined Language and Motor domains of the CRS and without a rescue medication through 72 weeks for IT ERT naïve subjects and 80 weeks for IT ERT-treated subjects post AAV9.CB7.hCLN2 as compared to a natural history cohort. In addition to 2 eligible subjects in the first cohort, a total of 15 subjects in the high dose of AAV9.CB7.hCLN2 group would be required to detect around 60% difference in the proportion of responders at Week 72 for IT ERT naïve subjects and Week 80 for IT ERT-treated subjects, assuming the response rate of around 35% and 95% in the natural history control group and IT ERT naïve and IT ERT-treated AAV9.CB7.hCLN2 group, respectively, a two-sided significance level of 0.05, and 80% power. The response rate of 35% at Week 72 in the natural history control group was estimated based on the Brineura® study results, where the response rate of 45% was reported at Week 48.

Establishment of Clinical Efficacy Based on Totality of Data

FDA provides multiple opportunities to expedite drug development for rare diseases and specifically addresses the targeting of a deficient gene in the FDA Draft Guidance for Industry: Expedited Programs for Serious Conditions—Drugs and Biologics—2014. This guidance also provides some insights relevant to endpoints that may be sufficient to support registration of a product for rare genetic diseases, stating that "for some well understood enzyme deficiencies, replacement of a deficient enzyme reliably predicts clinical benefit." This suggests that a gene therapy that reliably demonstrates transgene expression activity could meet the standard for accelerated approval under 21 CFR 314, subpart H. Moreover, based on this assertion, the case for early approval endpoints could be made for diseases in which deficient enzyme levels are linked to known etiology and their correction or normalization is associated with clinically meaningful effect.

In the setting of a previously-approved ERT, the correlation between enzyme levels (typically a secondary endpoint) and clinically meaningful outcomes (the precedent primary endpoint) is already established. In these instances, such as in many LSDs including CLN2 disease, successful delivery of a functioning gene copy and subsequent expression of the transgene product is evident at early timepoints (eg, such as though measurement of reductions in CSF lysosomal storage material or enzymatic activity) well in advance of observed improvements in clinical outcomes. This suggests that enzymatic activity after gene therapy can be used as a proxy for clinical benefit. The use of enzyme activity as a basis for approval proposed is also consistent with FDA precedent, as recently stated in the FDA Directors memo in the approval of Brineura® which speaks to the approvability of duration of response: "Since CLN2 is specifically attributed to deficiency of TPP1, reversal or prevention of its manifestations are theoretically possible if the replacement of TPP1 is durable or treatment is begun early in the course of the disease." Therefore, the potential for using TTP1 activity as an endpoint is consistent with FDA guidance.

Based on the established role of TPP1 enzymatic activity in preventing pathological accumulation of lysosomal storage material and known etiology of CLN2 disease, significant and sustained increases in TPP1 activity are likely to be predictive of long-term stabilization in neurobehavioral function. Based on data from a study that evaluated mouse CLN2 mutants that express different amounts of TPP1, TPP1 enzymatic activity levels of 3-6% of normal appear to be sufficient to dramatically delay disease onset and increase survival (Sleat et al., 2008). Additional clinical data from patients with CLN2 disease suggest that certain mutations in CLN2 lead to an incomplete loss of TPP1 enzymatic activity (at least in peripheral tissues) and a subsequently protracted phenotype (Sleat et al., 1999; Bessa et al., 2008; Schulz et al., 2013). Furthermore, ERT with recombinant TPP1 (Brineura®, cerliponase alfa, BioMarin Pharmaceuticals), administered as a biweekly infusion into CSF via a permanently implanted device, was determined to stabilize declines in i) motor function over a 96-week study period by the FDA; and ii) both motor and language function over a 48-week study period by EMA. AAV9.CB7.hCLN2 is designed for the efficient and sustained expression of TPP1 in the CNS, and the one-time delivery of AAV9.CB7.hCLN2 into the CSF has the potential to provide a long-term source of the TPP1 enzyme and halt (or significantly delay) disease progression and neurocognitive decline in this rare genetic disease with high unmet need. Thus, if clinical data indicate significant and sustained increases in TPP1 enzymatic activity in the CSF at early timepoints that are suggestive of longer-term improvements in clinically meaningful stabilization in CRS, the adequacy of these data to provide primary support for the efficacy of AAV9.CB7.hCLN2 in a future marketing application will be discussed with the FDA.

Example 16: Assessment of Intracerebroventricular AAV9.hCLN2co Efficacy in Batten Mice Using a Digital Vivarium CLN2 disease, a form of Batten disease, is a neurodegenerative lysosomal storage disorder caused by mutations in the gene encoding the soluble enzyme, tripeptidyl-peptidase-1 (TPP1). The disease is characterized by early onset at 2-4 years of age with seizures and ataxia before death by mid-childhood. Enzyme replacement therapy (ERT) with recombinant TPP1 (Brineura®, BioMarin Pharmaceuticals) was recently approved and is administered as a biweekly infusion into the lateral ventricles via a permanently implanted device. Repeat infusions are necessary due to the short half-lives of recombinant enzymes. Thus, there remains a significant unmet need for therapies that can provide sustained TPP1 activity in patients without the high burden associated with repeat administration.

To address this, we conducted a study to assess the efficacy of intracerebroventricular (ICV) AAV9 encoding human TPP1 in a mouse model of CLN2 disease, the TPP1$^{m1J}$ mutant. The TPP1$^{m1J}$ mice recapitulate most features of the human disease, such as shortened lifespan, seizures, or abnormal gait. Objective monitoring of the neurobehavioral function in this model is, however, challenging as they are prone to stress-induced fatal seizures after 3 months of age and do not present any measurable deficit before this age. To circumvent this, we used an unbiased non-invasive full-time monitoring system in a digital vivarium (Vium, Inc.). This technology allows continuous recording in the home cage of single-housed mice without any operator manipulation, thus limiting stress and external bias. Seven-week-old C57Bl/6 TPP1$^{m1J}$ KO mice received a single dose of $3 \times 10^{11}$ GC of AAV9-hCLNco in the right cerebral ventricle; vehicle-injected WT littermates and TPP1$^{m1J}$ mice were used as controls. Recordings started 2 weeks after treatment and continued until sacrifice or unscheduled death. At study termination, 16 weeks post-ICV injection, necropsies were performed and brain and liver were sampled.

All mice were single-housed in Vium smart houses with continuous recording of the following parameters:
Nightly motion
Daily motion
Breathing rate
Circadian rhythms In addition, weekly clinical observations and body weights were documented. Recordings started 2 weeks after AAV9-hCLNco ICV injection (age 9 weeks) and continued until the scheduled sacrifice (16 weeks post injection, age 23 weeks) or before in case of unscheduled death. Deaths and euthanasia of moribund animals were recorded throughout the study. At scheduled study termination, 16 weeks post-ICV injection, necropsies were performed in the animals that remained, brain and liver weights were recorded, and assessment of histopathology in the brain and liver was conducted.

Figure 22A:
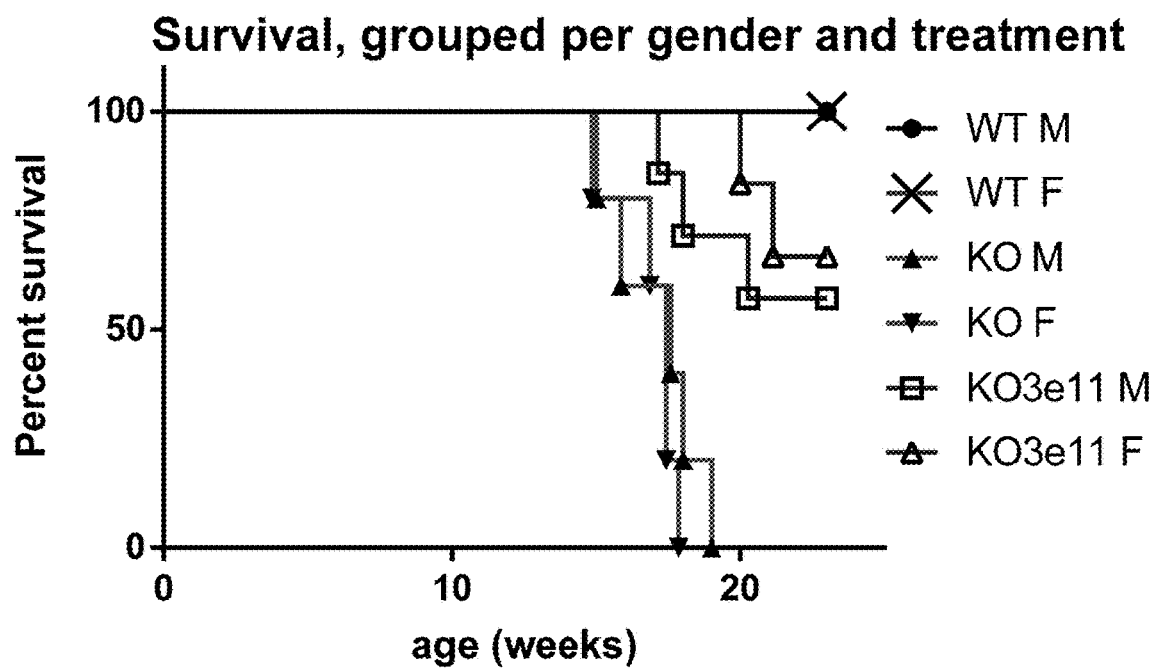
FIGS. 22A and 22B demonstrate increased survival of KO mice treated with intracerebroventricular injection of 3×1011 GC AAV9.CB7.hTPP1co. All vehicle treated KO animals were found dead or humanely euthanized before the age of 19 weeks whereas 67% of vector treated females (KO 3e11 F) and 57% of vector treated males (KO 3e11 M) were alive at the scheduled 23 weeks endpoint. **** Log-rank Mantel-Kox test, p<0.0001.
Figure 22B:
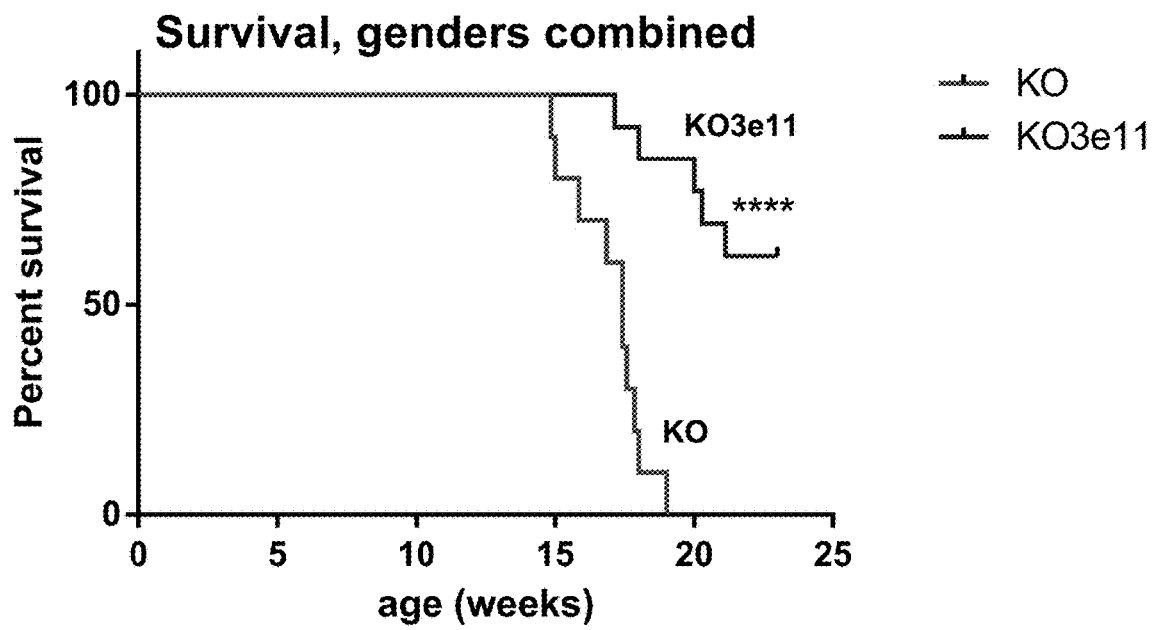
Figure 25A:
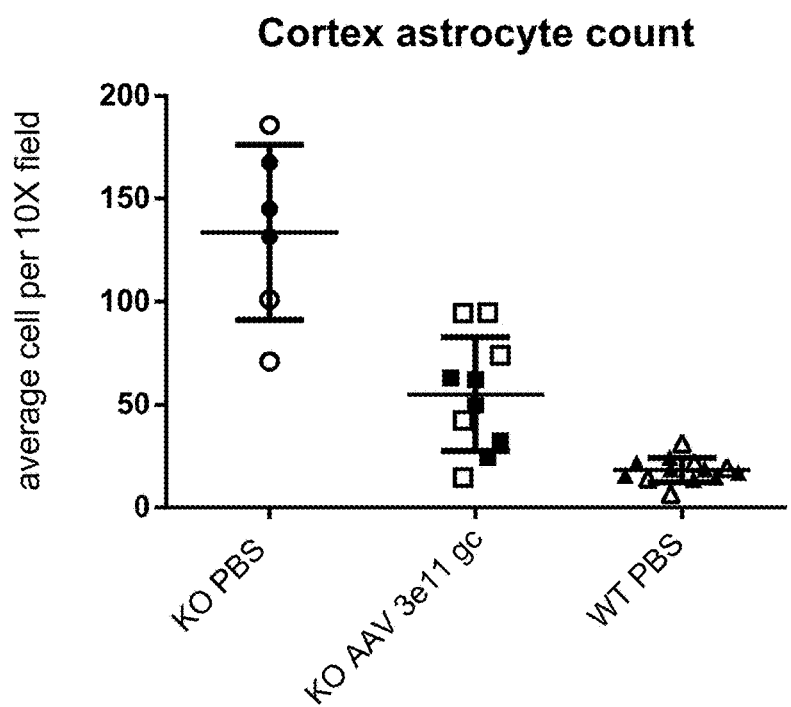
FIGS. 25A and 25B demonstrate that neuroinflammation is reduced in treated KO mice. (A) Cortical astrocyte average count per 10× field. Black symbols females, open symbols males. Animals found dead were excluded due to autolysis. (B) Representative immunostaining of astrocytes using an anti-GFAP antibody.
Figure 25B:
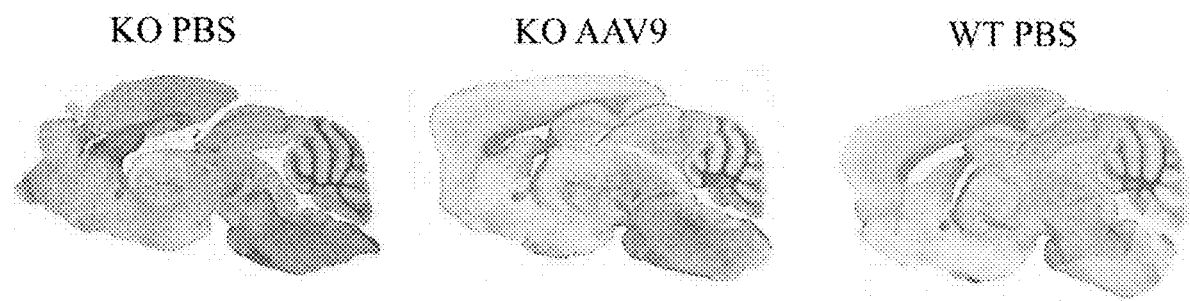

All untreated KO animals had tremors, hunched posture, abnormal gait, or seizures, or were found moribund or found dead, whereas 54% of vector treated KO animals were unremarkable throughout the study. All vehicle-treated KO had reported clinical signs starting as early as 14.9 weeks whereas 54% of vector treated KO (7 out of 13) were clinically unremarkable throughout the study. The average age at first clinical event was 16.1 weeks in KO vehicle treated animals and 18.6 weeks in the 6 vector-treated KO that had clinical events recorded; 7 vector-treated KO had no clinical event. Treatment was well tolerated in all animals, produced supraphysiologic TPP1 activity in liver, and increased the lifespan of KO mice. At the terminal endpoint (age 23 weeks), 62% of treated KO versus 0% of untreated KO mice were alive (FIG. 22B). The vector delayed and decreased the incidence of clinical events (Table 2). The lifespan of vector-treated mice was significantly increased (FIGS. 25A and 25B). The median survival of vehicle treated animals was 17.6 weeks in KO males and 17.4 weeks in KO females (absence of gender effect on survival of single-housed untreated TPP1m1J mice) (FIG. 22A). Death occurred on average 1.5 weeks after the onset of clinically visible signs. At the terminal sacrifice endpoint (16 weeks post injection, age 23 weeks), 57% of treated males (4 out of 7) and 67% of treated females (4 out of 6) were alive whereas all untreated KO mice were dead by the age of 19 weeks (FIGS. 22A and 22B). The comparison of survival curves of treated KO mice and vehicle treated KO mice shows a statistically significant increased survival in treated animals (Log-rank Mantel-Kox test, p<0.0001).

TABLE 2

Clinical events (incidence) of TPP1m1J and WT littermates treated with intracebroventricular injection of vehicle or of 3x1011 GC AAV9.CB7.hTPP1co

| Clinical event | KO PBS n = 10 | KO AAV9 n = 13 | WT PBS n = 13 |
|---|---|---|---|
| BARH throughout study | 0% | 61.5% | 100% |
| Tremors | 60% | 38.5% | 0% |
| Seizure | 40% | 7.7% | 0% |
| Moribund | 60% | 15.4% | 0% |
| Found dead | 40% | 23.1% | 0% |
| 1$^{st}$ clinical event | 14.9 to 17.6 weeks | 17 to >23 weeks | / |

Figure 23A:
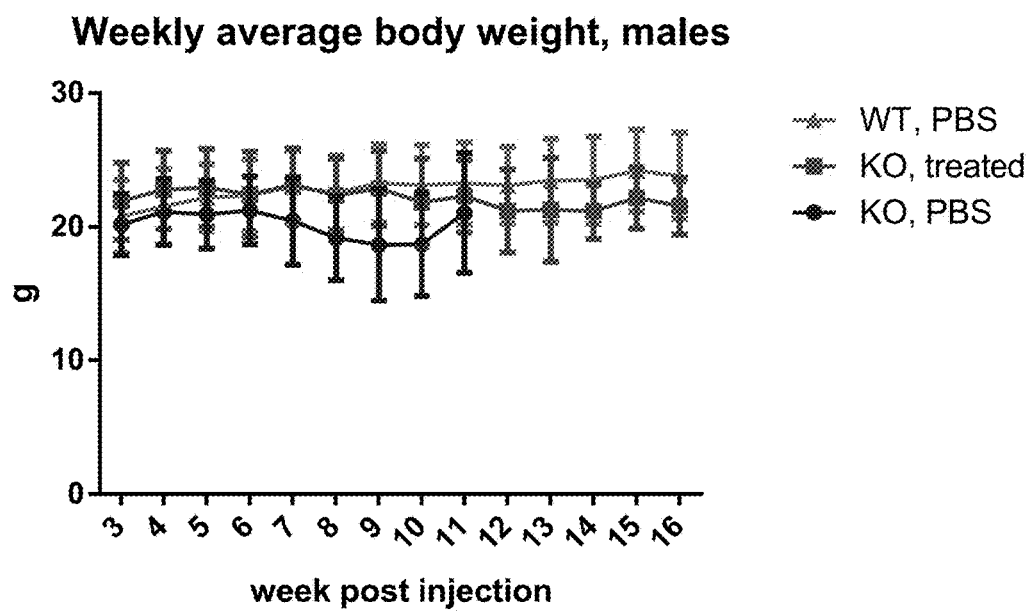
FIGS. 23A and 23B shows weekly average body weight in mice treated as in FIGS. 22A and B. Vehicle-treated KO mice started losing weight 6 weeks post injection. Vector-treated animals maintained their body weight until sacrifice.
Figure 23B:
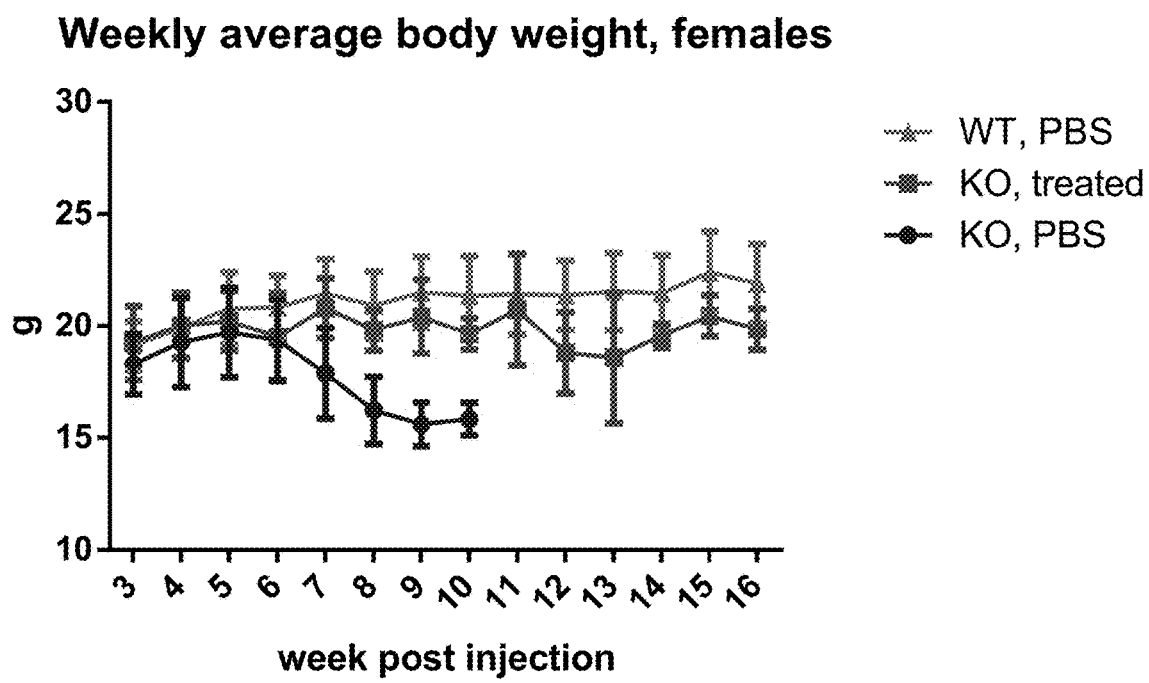
Figure 24:
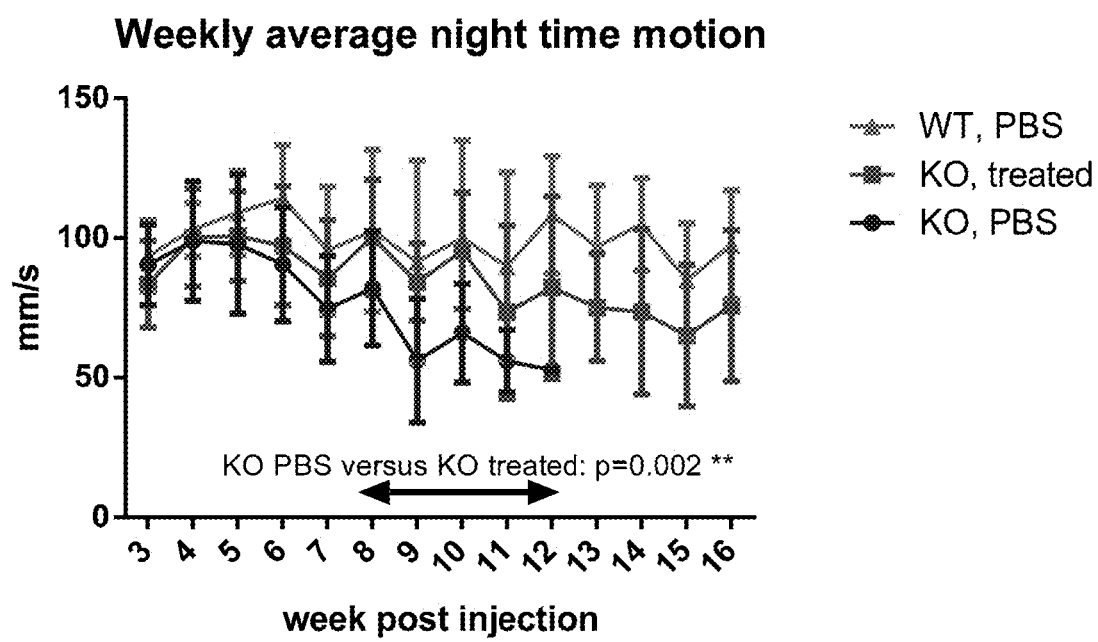
FIG. 24 shows weekly average night time motion in mice treated as in FIGS. 22A and 22B. Weekly average night time motion speed monitoring shows therapeutic efficacy before the onset of clinical symptoms. Comparisons were carried out using linear mixed effect modeling within the R program. The analysis was not stratified by gender. Statistical Significance was assessed at the 0.05 level. Treatment effect in KO animals was significant from Vium Day 40 (7.7 weeks post-injection; age 14.7 weeks).

PBS: Phosphate buffered saline (vehicle control)
BARH: bright, alert, responsive, and hydrated Further, AAV9.CB7.hTPP1co vector prevented disease-related weight loss (FIGS. 23A and 23B). Treatment preserved the biphasic circadian motion profile (data not shown), and weekly average night time motion (FIG. 24). Both WT and treated KO animals showed a clear biphasic circadian motion profile whereas vehicle treated mice started to lose the biphasic profile around 16 weeks of age. Continuous recording of motion using the smart cages allowed detection of neurobehavioral impairment in vehicle treated TPP1m1J mice from 14.7 weeks of age onward, in otherwise asymptomatic mice (FIG. 24). Breathing rate was comparable in all groups (not shown).

Taking advantage of the repeated measurements allowed by the digital vivarium, the statistical analysis of nightly motion speed using linear mixed effect modeling showed a significant therapeutic benefit in vector-treated KO mice starting at 14.7 weeks of age, while the average age at first clinical event was 16.1 weeks. This demonstrates that KO mice have neurobehavioral impairment that precedes the onset of grossly visible clinical signs and that treatment rescued this impairment. Corresponding to the rescue of neurobehavioral parameters, astrocytosis (FIGS. 25A and 25B), a marker of neuroinflammation, was decreased in vector-treated animals.

Altogether, these results demonstrate the therapeutic efficacy of AAV9-mediated gene therapy to prevent neurobehavioral manifestations, increase survival, maintain quality of life, and rescue the neuroinflammation related to CLN2 disease. Using a state-of-the art digital vivarium, we also demonstrated the presence of circadian rhythm abnormality in presymptomatic mice providing objective early efficacy readout in this model. This pilot study suggests that a single administration of AAV9 in the cerebrospinal fluid could be an alternative to repeat ERT for the treatment of CLN2 disease.

All published documents cited in this specification are incorporated herein by reference, as are PCT/US2018/032278, filed May 11, 2018, U.S. Provisional Patent Application No. 62/652,006, filed Apr. 3, 2018, U.S. Provisional Patent Application No. 62/599,816, filed Dec. 18, 2017, and U.S. Provisional Patent Application No. 62/504,817, filed May 11, 2017. Similarly, the SEQ ID NOs which are referenced herein and which appear in the appended Sequence Listing are incorporated by reference. While the invention has been described with reference to particular embodiments, it will be appreciated that modifications can be made without departing from the spirit of the invention. Such modifications are intended to fall within the scope of the appended claims.

What is claimed is:

1. A recombinant adeno-associated virus (rAAV), comprising an AAV serotype 9 (AAV9) capsid, wherein the rAAV comprises a vector genome packaged within the capsid, wherein the vector genome comprises:
   (a) an AAV2 5' inverted terminal repeat (ITR) sequence;
   (b) a promoter;
   (c) a CLN2 coding sequence encoding a human tripeptidyl peptidase 1 (TPP1); and
   (d) an AAV2 3' ITR sequence,
   wherein the CLN2 coding sequence shares 95% or greater identity with the nucleotide sequence set forth in SEQ ID NO: 3.

2. The rAAV according to claim 1, wherein the coding sequence of (c) comprises nucleotides 1 to 1689 of SEQ ID NO: 3.

3. The rAAV according to claim 1, wherein the promoter is a chicken beta-actin (CBA) promoter.

4. The rAAV according to claim 1, wherein the promoter is a hybrid promoter comprising a CBA promoter sequence and a cytomegalovirus enhancer element.

5. The rAAV according to claim 1, wherein the vector genome further comprises a polyA.

6. The rAAV according to claim 5, wherein the poly A is a synthetic polyA or from bovine growth hormone (bGH), human growth hormone (hGH), SV40, rabbit β-globin (RGB), or modified RGB (mRGB).

7. The rAAV according to claim 1, wherein the vector genome further comprises an intron.

8. The rAAV according to claim 7, wherein the intron is from CBA, human beta globin, IVS2, SV40, bGH, alpha-globulin, beta-globulin, collagen, ovalbumin, or p53.

9. The rAAV according to claim 1, wherein the vector genome further comprises an enhancer.

10. The rAAV according to claim 9, wherein the enhancer is a CMV enhancer, an RSV enhancer, an APB enhancer, ABPS enhancer, an alpha mic/bik enhancer, TTR enhancer, en34, or ApoE.

11. The rAAV according to claim 1, wherein the vector genome is about 3 kilobases to about 5.5 kilobases in size.

12. The rAAV according to claim 11, wherein the vector genome is about 4 kilobases in length.

13. A composition comprising the rAAV according to claim 1 and a pharmaceutically acceptable carrier or an excipient suitable for delivery to a central nervous system.

14. A composition comprising the rAAV according to claim 1 and a pharmaceutically acceptable carrier or an excipient suitable for intrathecal, intracisternal, or intracerebroventricular (ICV) delivery.

15. A recombinant adeno-associated virus (rAAV), comprising an AAV serotype 9 (AAV9) capsid or a variant thereof, wherein the rAAV comprises a vector genome packaged within the AAV9 capsid or variant thereof, wherein the vector genome comprises:
   (a) an AAV2 5' inverted terminal repeat (ITR) sequence;
   (b) a CBA promoter;
   (c) a CLN2 coding sequence comprising nucleotides 1 to 1689 of SEQ ID NO: 3 encoding a human TPP1;
   (d) a polyA; and
   (e) an AAV2 3' ITR sequence.

16. The rAAV according to claim 15, wherein the CBA promoter is a hybrid promoter comprising a CBA promoter sequence and a cytomegalovirus enhancer element.

17. The rAAV according to claim 15, wherein the poly A is a synthetic polyA or from bovine growth hormone (bGH), human growth hormone (hGH), SV40, rabbit β-globin (RGB), or modified RGB (mRGB).

18. A composition comprising the rAAV according to claim 15 and a pharmaceutically acceptable carrier or an excipient suitable for delivery to the central nervous system.

19. A composition comprising the rAAV according to claim 15 and a pharmaceutically acceptable carrier or an excipient suitable for intracerebroventricular (ICV) delivery.

20. A recombinant adeno-associated virus (rAAV), comprising an AAV9 capsid or variant thereof, wherein the rAAV comprises a vector genome packaged within the AAV9 capsid or variant thereof, wherein the vector genome comprises:
(a) an AAV2 5' inverted terminal repeat (ITR) sequence;
(b) a promoter;
(c) a CLN2 coding sequence encoding a human TPP1; and
(d) an AAV2 3' ITR sequence,
wherein the CLN2 coding sequence shares 95% or greater identity with the nucleotide sequence set forth in SEQ ID NO: 3, and
wherein the AAV9 capsid or variant thereof comprises capsid proteins having an amino acid sequence that shares 95% or greater identity with the amino acid sequence set forth in SEQ ID NO: 6.

21. The rAAV according to claim 20, wherein the coding sequence of (c) comprises nucleotides 1 to 1689 of SEQ ID NO: 3.

22. The rAAV according to claim 20, wherein the promoter is a chicken beta-actin (CBA) promoter.

23. The rAAV according to claim 20, wherein the promoter is a hybrid promoter comprising a CBA promoter sequence and cytomegalovirus enhancer elements.

24. The rAAV according to claim 20, wherein the vector genome further comprises a polyA.

25. The rAAV according to claim 24, wherein the polyA is a synthetic polyA or from bovine growth hormone (bGH), human growth hormone (hGH), SV40, rabbit β-globin (RGB), or modified RGB (mRGB).

26. The rAAV according to claim 20, wherein the vector genome further comprises an intron.

27. The rAAV according to claim 26, wherein the intron is from CBA, human-beta globin, IVS2, SV40, bGH, alpha-globulin, beta-globulin, collagen, ovalbumin, or p53.

28. The rAAV according to claim 20, wherein the vector genome further comprises an enhancer.

29. The rAAV according to claim 28, wherein the enhancer is a CMV enhancer, an RSV enhancer, an APB enhancer, ABPS enhancer, an alpha mic/bik enhancer, TTR enhancer, en34, or ApoE.

30. The rAAV according to claim 20, wherein the vector genome is about 3 kilobases to about 5.5 kilobases in size.

31. The rAAV according to claim 30, wherein the vector genome is about 4 kilobases in size.

32. A composition comprising the rAAV according to claim 20 and a pharmaceutically acceptable carrier or an excipient suitable for delivery to a central nervous system.

33. A composition comprising the rAAV according to claim 20 and a pharmaceutically acceptable carrier or an excipient suitable for intracerebroventricular (ICV) delivery.

34. A recombinant nucleic acid molecule comprising an expression cassette comprising a CLN2 coding sequence, wherein the CLN2 coding sequence comprises nucleotides 1 to 1689 of SEQ ID NO: 3.

35. A plasmid comprising the recombinant nucleic acid molecule according to claim 34.

36. An isolated host cell comprising the plasmid according to claim 35.

37. The isolated host cell according to claim 36, wherein the cell is a prokaryotic cell or a eukaryotic cell.

38. A packaging host cell comprising (a) the recombinant nucleic acid molecule according to claim 34; (b) a recombinant nucleic acid molecule encoding an AAV rep protein; (c) a recombinant nucleic acid molecule encoding an AAV capsid protein; and (d) sufficient helper sequences to package the expression cassette into an AAV capsid.

39. The packaging host cell according to claim 38, wherein the recombinant nucleic acid molecule encoding an AAV capsid protein comprises the nucleic acid sequence set forth in SEQ ID NO: 7, or a nucleic acid sequence at least 95% identical to SEQ ID NO: 7.

40. The packaging host cell according to claim 38, wherein the packaging host cell is a mammalian cell.

41. The packaging host cell according to claim 40, wherein the mammalian cell is a HEK293 cell.

42. An aqueous suspension comprising an aqueous suspending liquid and about $1\times10^9$ to about $1\times10^{15}$ genome copies or viral particles of the recombinant adeno-associated virus (rAAV), said rAAV having an AAV9 capsid, and having packaged therein a vector genome comprising:
(a) an AAV2 5' inverted terminal repeat (ITR) sequence;
(b) a promoter;
(c) a CLN2 coding sequence encoding a human tripeptidyl peptidase 1 (TPP1); and
(d) an AAV2 3' ITR sequence,
wherein the CLN2 coding sequence shares 95% or greater identity with the nucleotide sequence set forth in SEQ ID NO: 3.

43. The aqueous suspension according to claim 42, wherein the aqueous suspension is suitable for intrathecal delivery or intracerebroventricular delivery.

44. The aqueous suspension according to claim 42, wherein the aqueous suspension further comprises a surfactant, preservative, and/or buffer dissolved in the aqueous suspending liquid.

45. A method of treating a subject having Batten disease with a therapeutically effective amount of the rAAV according to claim 1.

46. The method according to claim 45, wherein the therapeutically effective amount is about $1\times10^9$ to about $1\times10^{16}$ vector genomes of the rAAV in an aqueous suspension.

47. The aqueous suspension according to claim 42, wherein the CLN2 coding sequence comprises nucleotides 1 to 1689 of SEQ ID NO: 3.

* * * * *

SEQUENCE LISTING

```
Sequence total quantity: 8
SEQ ID NO: 1             moltype = AA  length = 563
FEATURE                  Location/Qualifiers
source                   1..563
                         mol_type = protein
                         organism = Homo sapiens
SEQUENCE: 1
MGLQACLLGL FALILSGKCS YSPEPDQRRT LPPGWVSLGR ADPEEELSLT FALRQQNVER   60
LSELVQAVSD PSSPQYGKYL TLENVADLVR PSPLTLHTVQ KWLLAAGAQK CHSVITQDFL  120
TCWLSIRQAE LLLPGAEFHH YVGGPTETHV VRSPHPYQLP QALAPHVDFV GGLHRFPPTS  180
SLRQRPEPQV TGTVGLHLGV TPSVIRKRYN LTSQDVGSGT SNNSQACAQF LEQYFHDSDL  240
AQFMRLFGGN FAHQASVARV VGQQGRGRAG IEASLDVQYL MSAGANISTW VYSSPGRHEG  300
QEPFLQWLML LSNESALPHV HTVSYGDDED SLSSAYIQRV NTELMKAAAR GLTLLFASGD  360
SGAGCWSVSG RHQFRPTFPA SSPYVTTVGG TSFQEPPLIT NEIVDYISGG GFSNVFPRPS  420
YQEEAVTKFL SSSPHLPPSS YFNASGRAYP DVAALSDGYW VVSNRVPIPW VSGTSASTPV  480
FGGILSLINE HRILSGRPPL GFLNPRLYQQ HGAGLFDVTR GCHESCLDEE VEGQGFCSGP  540
GWDPVTGWGT PNFPALLKTL LNP                                         563

SEQ ID NO: 2             moltype = DNA  length = 1693
FEATURE                  Location/Qualifiers
```

```
source                 1..1693
                       mol_type = unassigned DNA
                       organism = Homo sapiens
SEQUENCE: 2
atgggactcc aagcctgcct cctagggctc tttgccctca tcctctctgg caaatgcagt    60
tacagcccgg agcccgacca gcggaggacg ctgcccccag gctgggtgtc cctgggccgt   120
gcggaccctg aggaagagct gagtctcacc tttgccctga cagcagaa tgtggaaaga    180
ctctcggagc tggtgcaggc tgtgtcggat cccagctctc ctcaatacgg aaaatacctg   240
accctagaga atgtggctga tctggtgagg ccatcccac tgaccctcca cacggtgcaa    300
aaatggctct tggcagccgg agcccagaag tgccattctg tgatcacaca ggactttctg   360
acttgctggc tgagcatccg acaagcagag ctgctgctcc ctgggctga gtttcatcac    420
tatgtgggag gacctacgga aacccatgtt gtaaggtccc cacatcccta ccagcttcca   480
caggccttgg cccccccatgt ggactttgtg ggggactgc accgtttcc cccaacatca    540
tccctgagcc aactgtcctga gccgcaggtg cagggactg taggcctgca tctggggta    600
accccctctg tgatccgtaa gcgatacaac ttgacctcac aagacgtggg ctctggcacc   660
agcaataaca gccaagcctg tgcccagttc tggagcagt atttccatga ctcagacctg    720
gctcagttca tgcgcctctt cggtggcaac tttgcacatc aggcatcagt agcccgtgtg   780
gttggacaac aggggcgggg ccgggccggg attgaggcca gtctagatgt gcagtacctg    840
atgagtgctg gtgccaacat ctccacctgg gtctacagta gccctggccg catgaggga    900
caggagccct cctgcagtg gctcatgctg ctcagtaatg agtcagccct gccacatgtg    960
catactgtga gctatggaga tgatgaggac tccctcagca gcgcctacat ccagcgggtc   1020
aacactgagc tcatgaaggc tgccgctcgg ggtctcaatc tgctcttcgc ctcaggtgac   1080
agtggggccg ggtgttggtc tgtctctgga agacaccagt tccgccctac cttccctgcc   1140
tccagcccct atgtcaccac agtggggagg acatccttcc aggaaccttt cctcatcaca   1200
aatgaaattg ttgactatat cagtggtggt ggcttcagca atgtgttccc acggccttca   1260
taccaggagg aagctgtaac gaagttcctg agctctgacc cccacctgcc accatccagt   1320
tacttcaatg ccagtggccg tgcctaccca gatgtggctg cacttctctga tggctactgg  1380
gtggtcagca acagagtgcc cattccatgg gtgtccggaa cctcggcctc tactccagtg   1440
tttgggggga tcctatcctt gatcaatgag cacaggatcc ttagtggccg ccccctcttg   1500
ggctttctca acccaaggct ctaccagcag catgggggcag gactctttga tgtaaccgt   1560
ggctgccatg agtcctgtct ggatgaagag gtagaggcc agggtttctg ctctggtcct   1620
ggctgggatc ctgtaacagg ctggggaaca cccaacttcc cagctttgct gaagactcta   1680
ctcaaccccct gac                                                     1693

SEQ ID NO: 3          moltype = DNA   length = 1693
FEATURE               Location/Qualifiers
misc_feature          1..1693
                      note = constructed sequence
source                1..1693
                      mol_type = other DNA
                      organism = synthetic construct
SEQUENCE: 3
atgggactgc aggcctgtct gctgggactg ttcgccctga tcctgagcgg caagtgcagc    60
tacagccccg agcccgacca gagaagaaca ctgcctccag gctgggtgtc cctgggcaga   120
gctgaccctg aagaggaact gagcctgacc ttcgccctgc ggcagcagaa cgtgaaaga    180
ctgagcgagc tggtgcaggc cgtgtccgat cctagcagcc ctcagtacgg caagtacctg   240
accctgaaaa acgtggccga cctcgtgcgg cctagcccc tgcactgca caccgtgcag    300
aagtggctgc tggctgccgg cgctcagaaa tgccactccg tgatcaccca ggactttctg   360
acctgttggc tgagcatccg gcaggccgaa ctgctgctgc ctgggccga gtttcaccac    420
tatgtgggcg gaccccacga gacacatgtc gtgcgcagcc cacaccctta ccagctgcca   480
caggctctgg cccctcacgt ggactttgtg ggaggcctgc acagattccc cccaaccgc    540
agcctgagac agaggcctga gccacaagtg accggcacag tgggcctgca tctgggcgtg   600
acacctagcg tgatccggaa gcggtacaac ctgaccagcc aggatgtggg cagcggcacc    660
agcaacaata gccaggcctg cgcccagttc tggaacagt acttccacga cagcgatctg    720
gcccagttca tgcggctgtt cggcggcaac ttcgcacatc agctgctg gccagagtc     780
gtgggccagc agggaagagg cagagccgga attgaggcct ccctggacgt gcagtacctg    840
atgagcgctg cgccaacat cagcacctgg gtgtacagca gccccggcag acacgagggc   900
caggaacctt ttctgcagtg gctgatgctg ctgagcaacg agagcgccct gcctcatgtg   960
cacacagtgt cctacggcga cgacgaggac agcctgagcc tacat ccagagagtg       1020
aacaccgagc tgatgaaggc cgctgccagg ggactgaacc tgctgtttgc ctctggcgat   1080
agcggagccg gctgttggag tgtgtcaggc cggcaccagt tcagacccac cttcctgcc    1140
agctcccctt acgtgacaac cgtgggcggc acctcctttc aggaaccctt cctgatcacc   1200
aacgagatcg tggactacat cagcggcgga ggcttcagca acgtgttccc cagacccagc   1260
taccaggaag aggccgtgac caagttcctg tcctccagcc ctcatctgcc ccccagctcc   1320
tacttcaacg ccagcggcag agcctaccca gatgtggcctg ctctgtccga cggctactgg   1380
gtggtgtcca acagagtgcc catcccttgg gtgtccggca agcgccag caccctgtg     1440
tttggcggca tcctgtccct gatcaacgag cacagaatcc tgtccggcag acccccctg    1500
ggcttcctga accctagact gtaccagcag cacggcgctg gcctgttcga tgtgaccaga   1560
ggctgccacg agagctgcct ggacgaggaa gttgaaggcc agggcttctg ttctggccct   1620
ggctgggatc ctgtgaccgg atggggcacc cctaacttcc ccgcctgct gaaaacactg    1680
ctgaaccccct gat                                                     1693

SEQ ID NO: 4          moltype = AA   length = 320
FEATURE               Location/Qualifiers
source                1..320
                      mol_type = protein
                      organism = Homo sapiens
SEQUENCE: 4
MRLFGGNFAH QASVARVVGQ QGRGRAGIEA SLDVQYLMSA GANISTWVYS SPGRHEGQEP    60
```

```
FLQWMLLLSN   ESALPHVHTV   SYGDDEDSLS   SAYIQRVNTE   LMKAAARGLT   LLFASGDSGA   120
GCWSVSGRHQ   FRPTFPASSP   YVTTVGGTSF   QEPFLITNEI   VDYISGGGFS   NVFPRPSYQE   180
EAVTKFLSSS   PHLPPSSYFN   ASGRAYPDVA   ALSDGYWVVS   NRVPIPWVSG   TSASTPVFGG   240
ILSLINEHRI   LSGRPPLGFL   NPRLYQQHGA   GLFDVTRGCH   ESCLDEEVEG   QGFCSGPGWD   300
PVTGWGTPNF   PALLKTLLNP                                                      320

SEQ ID NO: 5              moltype = DNA   length = 6841
FEATURE                   Location/Qualifiers
misc_feature              1..6841
                          note = constructed sequence
source                    1..6841
                          mol_type = other DNA
                          organism = synthetic construct
SEQUENCE: 5
tcgaggacgg ggtgaactac gcctgaggat ccgatctttt tccctctgcc aaaaattatg   60
gggacatcat gaagcccctt gagcatctga cttctggcta ataaaggaaa tttattttca  120
ttgcaatagt gtgttggaat ttttgtgtc tctcactcgg aagcaattcg ttgatctgaa   180
tttcgaccac ccataatacc cattaccctg gtagataagt agcatggcgg gttaatcatt  240
aactacaagg aaccctagt gatggagttg gccactccct ctctgcgcgc tcgctcgctc   300
actgaggccg ggcgaccaaa ggtcgcccga cgccgggctt tgcccgggc ggcctcagtg   360
agcgagcgag cgcgcagcct taattaacct aattcactgg ccgtcgtttt acaacgtcgt   420
gactgggaaa accctggcgt tacccaactt aatcgccttg cagcacatcc cctttcgcc    480
agctggcgta atagcgaaga ggcccgcacc gatcgccctt cccaacagtt gcgcagcctg   540
aatggcgaat gggacgcgcc ctgtagcggc gcattaagcg cggcgggtgt ggtggttacg   600
cgcagcgtga ccgctacact tgccagcgcc ctagcgcccg ctcctttcgc tttcttccct   660
tcctttctcg ccacgttcgc cggctttccc cgtcaagctc taaatcgggg gctccctta   720
gggttccgat ttagtgcttt acggcacctc gaccccaaaa aacttgatta gggtgatggt   780
tcacgtagtg ggccatcgcc ctgatagacg gtttttcgcc ctttgacgtt ggagtccacg   840
ttctttaata gtggactctt gttccaaact ggaacaacac tcaacccta ctcggtctat    900
tcttttgatt tataagggat tttgccgatt tcggcctatt ggttaaaaaa tgagctgatt   960
taacaaaaat ttaacgcgaa ttttaacaaa atattaacgc ttacaattta ggtggcactt  1020
ttcggggaaa tgtgcgcgga acccctattt gtttattttt ctaaatacat tcaaatatgt  1080
atccgctcat gagacaataa ccctgataaa tgcttcaata atattgaaaa aggaagagta  1140
tgagtattca acatttccgt gtcgccctta ttccctttt tgcggcattt tgccttcctg   1200
ttttgctca cccagaaacg ctggtgaaag taaaagatgc tgaagatcag ttgggtgcac   1260
gagtgggtta catcgaactg gatctcaaca gcggtaagat ccttgagagt tttcgccccg  1320
aagaacgttt tccaatgatg agcactttta aagttctgct atgtggcgcg gtattatccc  1380
gtattgacgc cgggcaagag caactcggtc gccgcataca ctattctcag aatgacttgg  1440
ttgagtactc accagtcaca gaaaagcatc ttacggatgg catgacagta agagaattat  1500
gcagtgctgc cataaccatg agtgataaca ctgcggccaa cttacttctg acaacgatcg  1560
gaggaccgaa ggagctaacc gcttttttgc acaacatggg ggatcatgta actcgccttg  1620
atcgttggga accggagctg aatgaagcca taccaaacga cgagcgtgac accacgatgc  1680
ctgtagcaat ggcaacaacg ttgcgcaaac tattaactgg cgaactactt actctagctt  1740
cccggcaaca attaatagac tggatggagg cggataaagt tgcaggacca cttctgcgct  1800
cggcccttcc ggctggctgg tttattgctg ataaatctgg agccggtgag cgtgggtctc  1860
gcggtatcat tgcagcactg gggccagatg gtaagccctc ccgtatcgta gttatctaca  1920
cgacgggag tcaggcaact atggatgaac gaaatagaca gatcgctgag ataggtgcct   1980
cactgattaa gcattggtaa ctgtcagacc aagtttactc atatatactt tagattgatt  2040
taaaacttca tttttaattt aaaaggatct aggtgaagat cctttttgat aatctcatga  2100
ccaaaatccc ttaacgtgag ttttcgttcc actgagcgtc agaccccgta gaaaagatca  2160
aaggatcttc ttgagatcct ttttttctgc gcgtaatctg ctgcttgcaa acaaaaaaac  2220
caccgctacc agcggtggtt tgtttgccgg atcaagagct accaactctt tttccgaagg  2280
taactggctt cagcagagcg cagataccaa atactgttct tctagtgtag ccgtagttag  2340
gccaccactt caagaactct gtagcaccgc ctacatacct cgctctgcta atcctgttac  2400
cagtggctgc tgccagtggc gataagtcgt gtcttaccgg gttggactca agacgatagt  2460
taccggataa ggcgcagcgg tcgggctgaa cggggggttc gtgcacacag cccagcttgg  2520
agcgaacgac ctacaccgaa ctgagatacc tacagcgtga gctatgagaa agcgccacgc  2580
ttcccgaagg gagaaaggcg gacaggtatc cggtaagcgg cagggtcgga acaggagagc  2640
gcacgaggga gcttccaggg ggaaacgcct ggtatcttta tagtcctgtc gggtttcgcc  2700
acctctgact tgagcgtcga tttttgtgat gctcgtcagg gggcggagc ctatggaaaa   2760
acgccagcaa cgcggccttt ttacggttcc tggccttttg ctggcctttt gctcacatgt  2820
tctttcctgc gttatcccct gattctgtgg ataaccgtat taccgccttt gagtgagctg  2880
ataccgctcg ccgcagccga acgaccgagc gcagcgagtc agtgagcgag gaagcggaag  2940
agcgcccaat acgcaaaccg cctctccccg cgcgttggcc gattcattaa tgcagctggc  3000
acgacaggtt tcccgactgg aaagcgggca gtgagcgcaa cgcaattaat gtgagttagc  3060
tcactcatta ggcaccccag gctttacact ttatgcttcc ggctcgtatg ttgtgtggaa  3120
ttgtgagcgg ataacaattt cacacaggaa acagctatga ccatgattac gccagattta  3180
attaaggcct taattaggct gcgcgctcgc tcgctcactg aggccgcccg ggcaaagccc  3240
gggcgtcggg cgaccttggg tcgcccggcc tcagtgagcg agcgagcgcg cagagaggga  3300
gtggccaact ccatcactag gggttccttg tagttaatga ttaacccgcc atgctactta  3360
tctaccaggg taatggggat cctctagaac tatagctagt cgacattgat tattgactag  3420
ttattaatag taatcaatta cggggtcatt agttcatagc ccatatatgg agttccgcgt  3480
tacataactt acggtaaatg gcccgcctgg ctgaccgccc aacgacccc gcccattgac    3540
gtcaataatg acgtatgttc ccatagtaac gccaataggg actttccatt gacgtcaata  3600
ggtggactat ttacggtaaa ctgcccactt ggcagtacat caagtgtatc atatgccaag  3660
tacgccccct attgacgtca atgacggtaa atggcccgcc tggcattatg cccagtacat  3720
gaccttatgg gactttccta cttggcagta catctacgta ttagtcatcg ctattaccat  3780
ggtcgaggtg agccccacgt tctgcttcac tctccccatc tcccccccct ccccacccc   3840
aattttgtat ttatttattt tttaattatt ttgtgcagcg atggggggcgg ggggggggg   3900
```

-continued

```
ggggcgcgcg ccaggcgggg cggggcgggg cgaggggcgg ggcggggcga ggcggagagg 3960
tgcggcggca gccaatcaga gcggcgcgct ccgaaagttt cctttttatgg cgaggcggcg 4020
gcggcggcgg ccctataaaa agcgaagcgc gcggcgggcg gggagtcgct gcgacgctgc 4080
cttcgccccg tgcccgctc cgccgccgcc tcgcgccgcc cgcccggct ctgactgacc 4140
gcgttactcc cacaggtgag cgggcgggac ggccttctc ctccgggctg taattagcgc 4200
ttggttaat gacggcttgt ttcttttctg tggctgcgtg aaagccttga ggggctccgg 4260
gagggcccctt tgtgcggggg gagcggctcg ggggtgcgt gcgtgtgtgt gtgcgtgggg 4320
agcgccgcgt gcggctccgc gctgcccggc ggctgtgagc gctgcgggcg cggcgcgggg 4380
ctttgtgcgc tccgcagtgt gcgcgagggg agcgcggccg ggggcggtgc cccgcggtgc 4440
ggggggggct gcgaggggaa caaaggctgc gtgcggggtg tgtgcgtggg ggggtgagca 4500
gggggtgtgg gcgcgtcggt cgggctgcaa cccccctgc acccccctcc ccgagttgct 4560
gagcacggcc cggcttcggg tgcggggctc cgtacgggc gtggcgcggg gctgccgtg 4620
ccgggcgggg ggtggcggca ggtgggggtg ccgggcgggg cggggccgcc tcgggccggg 4680
gagggctcgg gggaggggcg cggcggcccc cggagccgcg ggcgtgtcg aggcgcggt 4740
agccgcagcc attgccttt atggtaatcg tgcgagaggg cgcagggact tcctttgtcc 4800
caaatctgtg cggagccgaa atctggggagg cgccgccgca ccccctctag cgggcgcggg 4860
gcgaagcggt gcggcgccgg caggaaggaa atgggcgggg agggccttcg tgcgtcgccg 4920
cgccgccgtc cccttctccc tctccagcct cggggctgtc gcgggggga cggctgcctt 4980
cggggggggac ggggcagggc ggggttcggc ttctggcgtg tgaccggcgg ctctagagcc 5040
tctgctaacc atgttcatgc cttcttcttt ttcctacagc tcctgggcaa cgtgctggtt 5100
attgtgctgt ctcatcattt tggcaaagaa ttcacgcgtg ccaccatggg actgcaggcc 5160
tgtctgctgg gactgttcgc cctgatcctg agcggcactag ccccgagccc 5220
gaccagagaa gaacactgcc tccaggctgg gtgtccctgg gcagagctga ccctgaagag 5280
gaactgagcg tgaccttcgc cctgcggcag cagaacgtgg aaagactgag cgagctggtg 5340
caggccgtgt ccgatcctag cagccctcag tacggcaagt acctgaccct ggaaaacgtg 5400
gccgacctcg tgcggcctag ccctctgaca ctgcacacca tgcagaagtg gctgctggct 5460
gccggcgctc agaaatgcca ctccgtgatc acccaggact ttctgacctg ttggctgagc 5520
atccggcagg ccgaactgct gctgcctggg gccgagtttc accactatgt gggcggaccc 5580
accgagacac atgtcgtgcg cagccacac ccttaccagc tgccacaggc tctggccct 5640
cacgtggact ttgtgggagg cctgcacaga ttcccccaa ccagcagcct gagacagagg 5700
cctgagccac aagtgaccgg cacagtgggc ctgcatctgg gcgtgacacc tagcgtgatc 5760
cggaagcggt acaacctgac cagccaggat gtgggcagcg gcaccagcaa caatagccag 5820
gcctgcgccc agttcctgga acagtacttc cacgacagcg atctggccca gttcatgcgg 5880
ctgttcggcg gcaacttcgc acatcaggct agcggccca gagtcgtggg ccagcaggga 5940
agaggcagag ccggaattga ggcctccctg gacgtgcagt acctgactga cgctgccgcc 6000
aacatcagca cctgggtgta cagcagccc ggcagacacg agggccagga accttttctg 6060
cagtggctga tgctgctgag caacgagagc gccctgcctc atgtgcacac agtgtcctac 6120
ggcgacgacg aggacagcct gagcagcgcc tacatccaga gagtgaacac cgagctgatg 6180
aaggccgctc caggggact gaccctgctg ttgcctctg gcgataccga agccggctgc 6240
tggagtgtgt caggccggca ccagttcaga cccacctttc ctgccagctc ccctacgtg 6300
acaaccgtgg gcggcacctc cttcaggaa cccttcctga tcaccaacga gatcgtggac 6360
tacatcagcg cggaggctt cagcaacgtg ttccccagac cagctacca ggaagaggcc 6420
gtgaccaagt tcctgtcctc cagccctcat ctgccccca gctcctactt caacgccagc 6480
ggcagagcct acccagatgt ggccgctctg tccgacggct actgggtggt gtccaacaga 6540
gtgcccatcc cttgggtgtc cggcacaagc gccagccc tgtgttggg cggcatcctg 6600
tccctgatca acgagcacag aatcctgtcc ggcagaccc cctgggctt cctgaaccct 6660
agactgtacc agcacacgg cgctggcctg ttcgatgta ccagaggctg ccacgagagc 6720
tgcctggacg aggaagtgga aggcagggc ttcgtgttctg gccctggctg ggatcctgtg 6780
accggatggg gcacccctaa cttccccgcc ctgctgaaaa cactgctgaa cccctgatga 6840
c                                                                6841
SEQ ID NO: 6              moltype = AA   length = 736
FEATURE                   Location/Qualifiers
source                    1..736
                          mol_type = protein
                          organism = adeno-associated virus 9
SEQUENCE: 6
MAADGYLPDW LEDNLSEGIR EWWALKPGAP QPKANQQHQD NARGLVLPGY KYLGPGNGLD 60
KGEPVNAADA AALEHDKAYD QQLKAGDNPY LKYNHADAEF QERLKEDTSF GGNLGRAVFQ 120
AKKRLLEPLG LVEEAAKTAP GKKRPVEQSP QEPDSSAGIG KSGAQPAKKR LNFGQTGDTE 180
SVPDPQPIGE PPAAPSGVGS LTMASGGGAP VADNNEGADG VGSSSGNWHC DSQWLGDRVI 240
TTSTRTWALP TYNNHLYKQI SNSTSGGSSN DNAYFGYSTP WGYFDFNRFH CHFSPRDWQR 300
LINNNWGFRP KRLNFKLFNI QVKEVTDNNG VKTIANNLTS TVQVFTDSDY QLPYVLGSAH 360
EGCLPPFPAD VFMIPQYGYL TLNDGSQAVG RSSFYCLEYF PSQMLRTGNN FQFSYEFENV 420
PFHSSYAHSQ SLDRLMNPLI DQYLYYLSKT INGSGQNQQT LKFSVAGPSN MAVQGRNYIP 480
GPSYRQQRVS TTVTQNNNSE FAWPGASSWA LNGRNSLMNP GPAMASHKEG EDRFFPLSGS 540
LIFGKQGTGR DNVDADKVMI TNEEEIKTTN PVATESYGQV ATNHQSAQAQ AQTGWVQNQG 600
ILPGMVWQDR DVYLQGPIWA KIPHTDGNFH PSPLMGGFGM KHPPPQILIK NTPVPADPPT 660
AFNKDKLNSF ITQYSTGQVS VEIEWELQKE NSKRWNPEIQ YTSNYYKSNN VEFAVNTEGV 720
YSEPRPIGTR YLTRNL                                                736

SEQ ID NO: 7              moltype = DNA   length = 2211
FEATURE                   Location/Qualifiers
source                    1..2211
                          mol_type = unassigned DNA
                          organism = adeno-associated virus 9
SEQUENCE: 7
atggctgccg atggttatct tccagattgg ctcgaggaca accttagtga aggaattcgc 60
gagtggtggg ctttgaaacc tggagcccct caacccaagg caaatcaaca acatcaagac 120
```

```
aacgctcgag gtcttgtgct tccgggttac aaataccttg gacccggcaa cggactcgac   180
aaggggagc  cggtcaacgc agcagacgcg cgcgccctcg agcacgacaa ggcctacgac   240
cagcagctca aggccggaga caacccgtac ctcaagtaca accacgccga cgccgagttc   300
caggagcggc tcaaagaaga tacgtctttt ggggcaacc  tcgggcgagc agtcttccag   360
gccaaaaaga ggcttcttga acctcttggt ctggttgagg aagcggctaa gacggctcct   420
ggaaagaaga ggcctgtaga gcagtctcct caggaaccgg actcctccgc gggtattggc   480
aaatcgggtg cacagcccgc taaaaagaga ctcaatttcg gtcagactgg cgacacagag   540
tcagtcccag accctcaacc aatcggagaa cctcccgcag cccctcagg  tgtgggatct   600
cttacaatgg cttcaggtgg tggcgcacca gtggcagaca ataaccgaagg tgccgatgga  660
gtgggtagtt cctcgggaaa ttggcattgc gattcccaat ggctggggga cagagtcatc   720
accaccagca cccgaacctg ggccctgccc acctacaaca atcacctcta caagcaaatc   780
tccaacagca catctggagg atcttcaaat gacaacgcct acttcggcta cagcaccccc   840
tggggtatt  ttgacttcaa cagattccac tgccacttct caccacgtga ctggcagcga   900
ctcatcaaca acaactgggg attccggcct aagcgactca acttcaagct cttcaacatt   960
caggtcaaag aggttacgga caacaatgga gtcaagacca tcgccaataa ccttaccagc  1020
acgtccagg  tcttcacgga ctcagactat cagctcccgt acgtgctcgg gtcggctcac  1080
gagggctgcc tcccgccgtt cccagcggac gttttcatga ttcctcagta cgggtatctg  1140
acgcttaatg atggaagcca ggccgtgggt cgttcgtcc  tttactgcct ggaatatttc  1200
ccgtcgcaaa tgctaagaac gggtaacaac ttccagttca gctacgagtt tgagaacgta  1260
cctttccata gcagctacgc tcacagccaa agcctggacc gactaatgaa tccactcatc  1320
gaccaatact tgtactatct ctcaaagact attaacggtt ctggacagaa tcaacaaacg  1380
ctaaaattca gtgtggccgg acccagcaac atggctgtcc agggaagaaa ctacataccct 1440
ggacccagct accgacaaca acgtgtctca accactgtga ctcaaaacaa caacagcgaa  1500
tttgcttggc ctggagcttc ttcttgggct ctcaatggac gtaatagctt gatgaatcct  1560
ggacctgcta tggccagcca caagaagga  gaggaccgtt tctttccttt gtctggatct  1620
ttaatttttg gcaaacaagg aactggaaga gacaacgtgg atgcggacaa agtcatgata  1680
accaacgaag aagaaattaa aactactaac ccggtagcaa cggagtccta tggacaagtg  1740
gccacaaacc accagagtgc ccaagcacag gcgcagaccg gctgggttca aaaccaagga  1800
atacttccgg gtatggtttg gcaggacaga gatgtgtacc tgcaaggacc catttgggcc  1860
aaaattcctc acacggacgg caactttcac ccttctccgg tcatgggagg gtttggaatg  1920
aagcacccgc ctcctcagat cctcatcaaa aacacacctg tacctgcgga tcctccaacg  1980
gccttcaaca aggacaagct gaactctttc atcacccagt attctactgg ccaagtcagc  2040
gtggagatcg agtgggagct gcagaaggaa acagcaagc  gctggaaccc ggagatccga  2100
tacacttcca actattacaa gtctaataat gttgaatttg ctgttaatac tgaaggtgta  2160
tatagtgaac ccgcccccat tggcaccaga tacctgactc gtaatctgta a           2211
```

SEQ ID NO: 8     moltype = DNA length = 4020
FEATURE      Location/Qualifiers
misc_feature    1..4020
          note = constructed sequence
source       1..4020
          mol_type = other DNA
          organism = synthetic construct
SEQUENCE: 8

```
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact   120
aggggttcct tgtagttaat gattaacccg ccatgctact tatctaccag tgtaatgggg   180
atcctctaga actatagcta gtcgacattg attattgact agttattaat agtaatcaat   240
tacgggtca  ttagttcata gcccatatat ggagttccgc gttacataac ttacggtaaa   300
tggcccgcct ggctgaccgc ccaacgaccc cgcccattg  acgtcaataa tgacgtatgt   360
tcccatagta acgccaatag ggactttcca ttgacgtcaa tgggtggact atttacggta   420
aactgcccac ttggcagtac atcaagtgta tcatatgcca gtacgcccc  ctattgacgt   480
caatgacggt aaatggcccg cctggcatta tgcccagtac atgaccttat gggactttcc   540
tacttggcag tacatctacg tattagtcat cgctattacc atggtcgagg tgagcccac    600
gttctgcttc actctcccca tctccccccc tccccaccc  caattttgt  atttatttat   660
tttttaatta ttttgtgcag cgatggggg  gggggggggg ggggggcgcg cgccaggcgg   720
ggcggggcgg ggcgaggggc ggggcgggc  gaggcggaga ggtgcggcgg cagccaatca   780
gagcggcgcg ctccgaaagt ttccttttat ggcgaggcgg cggcggcggc ggccctataa   840
aaagcgaagc gcgcggcggg cggggagtcg ctgcgacgct gccttcgccc cgtgccccgc   900
tccgccgccg cctcgcgccg cccgccccgg ctctgactga ccgcgttact cccacaggtg   960
agcgggcggg acgccccttc tcctccgggc tgtaattagc gcttggttta atgacgcgtt  1020
gtttctttc  tgtggctgcg tgaaagcctt gaggggctcc gggagggccc tttgtgcggg  1080
gggagcggct cggggggtgc gtgcgtgtgt gtgtgcgtgg ggacgccgc  gtgcggctcc  1140
gcgctgcccg gcggctgtga gcgctgcggg cgcggcgtgg gcctttgtgc gctccgcagt  1200
gtgcgcgagg ggagcgcggc cgggggcggt gccccgcggt gcgggggggg ctgcgagggg  1260
aacaaaggct gcgtgcgggg tgtgtgcgtg gggggtgagc aggggggtgt gggcgcgtcg  1320
gtcgggctgc aaccccccct gcacccccct ccccgagttg ctgagcacgg cccggcttcg  1380
ggtgcggggc tccgtacggg gcgtggcgcg ggctcgccg  tgccgggcgg ggggtggcgg  1440
caggtggggg tgccggggcg ggcggggccg cctcgggggg cgcgcagggg gggagggg    1500
cgcggcggcc cccggagcgc cggcggctgt cgaggcgcgg cgagccgcag ccattgcctt  1560
ttatggtaat cgtgcgagag ggcgcaggga cttcctttgt cccaaatctg tgcggagccg  1620
aaatctggga ggcgccgccg cacccctct  agcgggcgcg ggcgaagcg  gtgcggcgcc  1680
ggcaggaagg aaatgggcgg gagggccttc gtgcgtcgc  cgcgccgccg tcccctttctc 1740
cctctccagc ctcggggctg tccgcggggg gacggctgcc ttcggggggg acggggcagg  1800
gcggggttcg gcttctggcg tgtgaccggc ggctctagag cctctgctaa ccatgttcat  1860
gccttcttct ttttcctaca gctcctgggc aacgtgctgg ttattgtgct gtctcatcat  1920
tttggcaaag aattcacgcg tgccaccatg ggactgcagg cctgtctgct gggactgttc  1980
gccctgatcc tgagcggcaa gtgcagctac agccccgagc ccgaccagag aagaactgg   2040
cctccaggct gggtgtccct gggcagagct gaccctgaag aggaactgag cctgacctcc  2100
```

-continued

```
gccctgcggc agcagaacgt ggaaagactg agcgagctgg tgcaggccgt gtccgatcct   2160
agcagccctc agtacggcaa gtacctgacc ctggaaaacg tggccgacct cgtgcggcct   2220
agccctctga cactgcacac cgtgcagaag tggctgctgg ctgccggcgc tcagaaatgc   2280
cactccgtga tcacccagga ctttctgacc tgttggctga gcatccggca ggccgaactg   2340
ctgctgcctg gggccgagtt tcaccactat gtgggcggac ccaccgagac acatgtcgtg   2400
cgcagcccac acccttacca gctgccacag gctctggccc ctcacgtgga ctttgtggga   2460
ggcctgcaca gattcccccc aaccagcagc ctgagacaga ggcctgagcc acaagtgacc   2520
ggcacagtgg gcctgcatct gggcgtgaca cctagcgtga tccggaagcg gtacaacctg   2580
accagccagg atgtgggcag cggcaccagc aacaatagcc aggcctgcgc ccagttcctg   2640
gaacagtact tccacgacag cgatctggcc cagttcatgc ggctgttcgg cggcaacttc   2700
gcacatcagg ctagcgtggc cagagtcgtg ggccagcagg gaagaggcag agccggaatt   2760
gaggcctccc tggacgtgca gtacctgatg agcgctggcg ccaacatcag cacctgggtg   2820
tacagcagcc ccggcagaca cgagggccag gaaccttttc tgcagtggct gatgctgctg   2880
agcaacgaga gcgccctgcc tcatgtgcac acagtgtcct acggcgacga cgaggacagc   2940
ctgagcagcg cctacatcca gagagtgaac accgagctga tgaaggccgc tgccagggga   3000
ctgacccctg tgtttgcctc tggcgatagc ggagccggct gttggagtgt gtcaggccgg   3060
caccagttca gacccacctt tcctgccagc tcccctacg tgacaaccgt gggcggcacc   3120
tcctttcagg aacccttcct gatcaccaac gagatcgtgg actacatcag cggcggaggc   3180
ttcagcaacg tgttccccag acccagctac caggaagagg ccgtgaccaa gttcctgtcc   3240
tccagccctc atctgccccc cagctcctac ttcaacgcca gcggcagagc ctacccagat   3300
gtggccgctc tgtccgacgg ctactgggtg gtgtccaaca gagtgcccat cccttgggtg   3360
tccggcacaa gcgccagcac ccctgtgttt ggcggcatcc tgtccctgat caacgagcac   3420
agaatcctgt ccggcagacc ccccctgggc ttcctgaacc ctagactgta ccagcagcac   3480
ggcgctggcc tgttcgatgt gaccagaggc tgccacgaga gctgcctgga cgaggaagtg   3540
gaaggccagg gcttctgttc tggccctggc tgggatcctg tgaccggatg gggcacccct   3600
aacttccccg ccctgctgaa aacactgctg aacccctgat gactcgagga cgggtgaac   3660
tacgcctgag gatccgatct tttccctct gccaaaaatt atgggacat catgaagccc   3720
cttgagcatc tgacttctgg ctaataaagg aaatttattt tcattgcaat agtgtgttgg   3780
aattttttgt gtctctcact cggaagcaat tcgttgatct gaatttcgac cacccataat   3840
acccattacc ctggtagata agtagcatgg cgggttaatc attaactaca aggaacccct   3900
agtgatggag ttggccactc cctctctgcg cgctcgctcg ctcactgagg ccgggcgacc   3960
aaaggtcgcc cgacgcccgg gctttgcccg ggcggcctca gtgagcgagc gagcgcgcag   4020
```